United States Patent
DeRosa et al.

(10) Patent No.: US 11,712,463 B2
(45) Date of Patent: *Aug. 1, 2023

(54) MRNA THERAPY FOR POMPE DISEASE

(71) Applicant: Translate Bio, Inc., Lexington, MA (US)

(72) Inventors: Frank DeRosa, Lexington, MA (US); Michael Heartlein, Lexington, MA (US)

(73) Assignee: Translate Bio, Inc., Lexington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/369,783

(22) Filed: Jul. 7, 2021

(65) Prior Publication Data

US 2021/0401951 A1    Dec. 30, 2021

Related U.S. Application Data

(63) Continuation of application No. 16/191,017, filed on Nov. 14, 2018, now Pat. No. 11,090,368, which is a continuation of application No. 15/073,163, filed on Mar. 17, 2016, now Pat. No. 10,172,924.

(60) Provisional application No. 62/135,338, filed on Mar. 19, 2015.

(51) Int. Cl.
| | |
|---|---|
| *A61K 31/7105* | (2006.01) |
| *A61K 47/22* | (2006.01) |
| *A61K 38/47* | (2006.01) |
| *A61K 9/00* | (2006.01) |
| *A61K 9/127* | (2006.01) |
| *C12N 9/40* | (2006.01) |
| *A61K 48/00* | (2006.01) |

(52) U.S. Cl.
CPC ............ *A61K 38/47* (2013.01); *A61K 9/0019* (2013.01); *A61K 9/127* (2013.01); *A61K 9/1271* (2013.01); *A61K 9/1272* (2013.01); *A61K 31/7105* (2013.01); *A61K 47/22* (2013.01); *A61K 48/0033* (2013.01); *A61K 48/0058* (2013.01); *C12N 9/2465* (2013.01); *C12Y 302/0102* (2013.01)

(58) Field of Classification Search
None
See application file for complete search history.

(56) References Cited

U.S. PATENT DOCUMENTS

| | | | |
|---|---|---|---|
| 5,705,385 A | 1/1998 | Bally et al. | |
| 5,976,567 A | 11/1999 | Wheeler et al. | |
| 5,981,501 A | 11/1999 | Wheeler et al. | |
| 6,534,484 B1 | 3/2003 | Wheeler et al. | |
| 6,815,432 B2 | 11/2004 | Wheeler et al. | |
| 7,422,902 B1 | 9/2008 | Wheeler et al. | |
| 7,745,651 B2 | 6/2010 | Heyes et al. | |
| 7,799,565 B2 | 9/2010 | MacLachlan et al. | |
| 7,803,397 B2 | 9/2010 | Heyes et al. | |
| 7,901,708 B2 | 3/2011 | MacLachlan et al. | |
| 8,101,741 B2 | 1/2012 | MacLachlan et al. | |
| 8,188,263 B2 | 5/2012 | MacLachlan et al. | |
| 8,236,943 B2 | 8/2012 | Lee et al. | |
| 8,329,070 B2 | 12/2012 | MacLachlan et al. | |
| 8,513,403 B2 | 8/2013 | MacLachlan et al. | |
| 8,569,256 B2 | 10/2013 | Heyes et al. | |
| 8,710,200 B2 | 4/2014 | Schrum et al. | |
| 8,822,663 B2 | 8/2014 | Chen et al. | |
| 8,853,377 B2 | 10/2014 | Guild et al. | |
| 8,883,202 B2 | 11/2014 | Manoharan et al. | |
| 8,936,942 B2 | 1/2015 | Heyes et al. | |
| 8,980,864 B2 | 3/2015 | Hoge et al. | |
| 8,999,351 B2 | 4/2015 | Manoharan et al. | |
| 8,999,380 B2 | 4/2015 | Bancel et al. | |
| 8,999,950 B2 | 4/2015 | MacLachlan et al. | |
| 9,018,187 B2 | 4/2015 | Heyes et al. | |
| 9,051,567 B2 | 6/2015 | Fitzgerald et al. | |
| 9,061,059 B2 | 6/2015 | Chakraborty et al. | |
| 9,074,208 B2 | 7/2015 | MacLachlan et al. | |
| 9,089,604 B2 | 7/2015 | Chakraborty et al. | |

(Continued)

FOREIGN PATENT DOCUMENTS

| | | |
|---|---|---|
| CA | 2 807 552 A1 | 9/2012 |
| EP | 1 519 714 B1 | 10/2010 |

(Continued)

OTHER PUBLICATIONS

Dong Yizhou et al., Lipopeptide nanoparticles for potent and selective siRNA delivery in rodents and nonhuman primates, Proceedings of the National Academy of Sciences of the United States of America, vol. 111, No. 11, Mar. 2014 (Mar. 2014), pp. 3955-3960.

(Continued)

*Primary Examiner* — Sean McGarry
(74) *Attorney, Agent, or Firm* — Proskauer Rose LLP; Fangli Chen; Lingyun Jia

(57) ABSTRACT

The present invention provides, among other things, methods of treating Pompe disease, including administering to a subject in need of treatment a composition comprising an mRNA encoding acid alpha-glucosidase (GAA) at an effective dose and an administration interval such that at least one symptom or feature of Pompe disease is reduced in intensity, severity, or frequency or has delayed in onset. In some embodiments, the mRNA is encapsulated in a liposome comprising one or more cationic lipids, one or more non-cationic lipids, one or more cholesterol-based lipids and one or more PEG-modified lipids.

20 Claims, 4 Drawing Sheets
(4 of 4 Drawing Sheet(s) Filed in Color)
Specification includes a Sequence Listing.

(56) References Cited

U.S. PATENT DOCUMENTS

| | | |
|---|---|---|
| 9,095,552 B2 | 8/2015 | Chakraborty et al. |
| 9,107,886 B2 | 8/2015 | Chakraborty et al. |
| 9,114,113 B2 | 8/2015 | Chakraborty et al. |
| 9,181,319 B2 | 11/2015 | Schrum et al. |
| 9,186,325 B2 | 11/2015 | Manoharan et al. |
| 9,186,372 B2 | 11/2015 | de Fougerolles et al. |
| 9,187,748 B2 | 11/2015 | Geisbert et al. |
| 9,192,651 B2 | 11/2015 | Chakraborty et al. |
| 9,220,755 B2 | 12/2015 | Chakraborty et al. |
| 9,220,792 B2 | 12/2015 | Chakraborty et al. |
| 9,233,141 B2 | 1/2016 | Chakraborty et al. |
| 9,254,311 B2 | 2/2016 | Bancel et al. |
| 9,295,689 B2 | 3/2016 | de Fougerolles et al. |
| 9,301,993 B2 | 4/2016 | Chakraborty et al. |
| 9,303,079 B2 | 4/2016 | Chakraborty et al. |
| 9,334,328 B2 | 5/2016 | Schrum et al. |
| 9,345,780 B2 | 5/2016 | Manoharan et al. |
| 9,352,042 B2 | 5/2016 | Heyes et al. |
| 9,352,048 B2 | 5/2016 | Manoharan et al. |
| 9,364,435 B2 | 6/2016 | Yaworski et al. |
| 9,370,581 B2 | 6/2016 | Manoharan et al. |
| 9,370,582 B2 | 6/2016 | Manoharan et al. |
| 2002/0192651 A1 | 12/2002 | Wheeler et al. |
| 2003/0181410 A1 | 9/2003 | Wheeler et al. |
| 2004/0142025 A1 | 7/2004 | MacLachlan et al. |
| 2006/0000891 A1 | 1/2006 | MacLachlan et al. |
| 2006/0083780 A1 | 4/2006 | Heyes et al. |
| 2007/0135372 A1 | 6/2007 | MacLachlan et al. |
| 2009/0270481 A1 | 10/2009 | MacLachlan et al. |
| 2010/0041152 A1 | 2/2010 | Wheeler et al. |
| 2011/0244026 A1 | 10/2011 | Guild et al. |
| 2011/0256175 A1 | 10/2011 | Hope et al. |
| 2011/0311583 A1 | 12/2011 | Manoharan et al. |
| 2012/0065252 A1 | 3/2012 | Schrum et al. |
| 2012/0128760 A1 | 5/2012 | Manoharan et al. |
| 2012/0142756 A1 | 6/2012 | Guild et al. |
| 2012/0202871 A1 | 8/2012 | Heyes et al. |
| 2012/0237975 A1 | 9/2012 | Schrum et al. |
| 2012/0251618 A1 | 10/2012 | Schrum et al. |
| 2012/0328668 A1 | 12/2012 | MacLachlan et al. |
| 2013/0158021 A1 | 6/2013 | Dong et al. |
| 2013/0195967 A1 | 8/2013 | Guild et al. |
| 2013/0237594 A1 | 9/2013 | de Fougerolles et al. |
| 2013/0259923 A1 | 10/2013 | Bancel et al. |
| 2013/0259924 A1 | 10/2013 | Bancel et al. |
| 2013/0266640 A1 | 10/2013 | de Fougerolles et al. |
| 2014/0010861 A1 | 1/2014 | Bancel et al. |
| 2014/0044772 A1 | 2/2014 | MacLachlan et al. |
| 2014/0105964 A1 | 4/2014 | Bancel et al. |
| 2014/0105965 A1 | 4/2014 | Bancel et al. |
| 2014/0147432 A1 | 5/2014 | Bancel et al. |
| 2014/0147454 A1 | 5/2014 | Chakraborty et al. |
| 2014/0148502 A1 | 5/2014 | Bancel et al. |
| 2014/0155472 A1 | 6/2014 | Bancel et al. |
| 2014/0155473 A1 | 6/2014 | Bancel et al. |
| 2014/0155474 A1 | 6/2014 | Bancel et al. |
| 2014/0155475 A1 | 6/2014 | Bancel et al. |
| 2014/0171485 A1 | 6/2014 | Bancel et al. |
| 2014/0179756 A1 | 6/2014 | MacLachlan et al. |
| 2014/0179771 A1 | 6/2014 | Bancel et al. |
| 2014/0186432 A1 | 7/2014 | Bancel et al. |
| 2014/0193482 A1 | 7/2014 | Bancel et al. |
| 2014/0194494 A1 | 7/2014 | Bancel et al. |
| 2014/0199371 A1 | 7/2014 | Bancel et al. |
| 2014/0200261 A1 | 7/2014 | Hoge et al. |
| 2014/0200262 A1 | 7/2014 | Bancel et al. |
| 2014/0200263 A1 | 7/2014 | Bancel et al. |
| 2014/0200264 A1 | 7/2014 | Bancel et al. |
| 2014/0206752 A1 | 7/2014 | Afeyan et al. |
| 2014/0206753 A1 | 7/2014 | Guild et al. |
| 2014/0206755 A1 | 7/2014 | Bancel et al. |
| 2014/0206852 A1 | 7/2014 | Hoge et al. |
| 2014/0221465 A1 | 8/2014 | Bancel et al. |
| 2014/0243399 A1 | 8/2014 | Schrum et al. |
| 2014/0249208 A1 | 9/2014 | Bancel et al. |
| 2014/0255467 A1 | 9/2014 | Bancel et al. |
| 2014/0255468 A1 | 9/2014 | Bancel et al. |
| 2014/0275227 A1 | 9/2014 | Hoge et al. |
| 2014/0275229 A1 | 9/2014 | Bancel et al. |
| 2014/0294937 A1 | 10/2014 | MacLachlan et al. |
| 2014/0343129 A1 | 11/2014 | de Fougerolles et al. |
| 2015/0005372 A1 | 1/2015 | Hoge et al. |
| 2015/0017211 A1 | 1/2015 | de Fougerolles et al. |
| 2015/0044277 A1 | 2/2015 | Bancel et al. |
| 2015/0050354 A1 | 2/2015 | Bouchon et al. |
| 2015/0051268 A1 | 2/2015 | Bancel et al. |
| 2015/0056253 A1 | 2/2015 | Bancel et al. |
| 2015/0064235 A1 | 3/2015 | Bancel et al. |
| 2015/0064236 A1 | 3/2015 | Bancel et al. |
| 2015/0064242 A1 | 3/2015 | Heyes et al. |
| 2015/0064725 A1 | 3/2015 | Schrum et al. |
| 2015/0086614 A1 | 3/2015 | Bancel et al. |
| 2015/0111248 A1 | 4/2015 | Bancel et al. |
| 2015/0111945 A1 | 4/2015 | Geisbert et al. |
| 2015/0166465 A1 | 6/2015 | Chen et al. |
| 2015/0190515 A1 | 7/2015 | Manoharan et al. |
| 2015/0265708 A1 | 9/2015 | Manoharan et al. |
| 2015/0315541 A1 | 11/2015 | Bancel et al. |
| 2015/0315584 A1 | 11/2015 | MacDonald et al. |
| 2015/0342940 A1 | 12/2015 | Benjamin et al. |
| 2015/0366997 A1 | 12/2015 | Guild et al. |
| 2016/0095924 A1 | 4/2016 | Hope et al. |
| 2016/0108133 A1 | 4/2016 | Armstrong et al. |
| 2016/0114011 A1 | 4/2016 | Bancel et al. |
| 2016/0115477 A1 | 4/2016 | MacLachlan et al. |
| 2016/0115483 A1 | 4/2016 | MacLachlan et al. |
| 2016/0121291 A1 | 5/2016 | Moonen |
| 2016/0136236 A1 | 5/2016 | Hoge et al. |
| 2016/0151284 A1 | 6/2016 | Heyes et al. |
| 2016/0158385 A1 | 6/2016 | Bancel et al. |
| 2016/0193299 A1 | 7/2016 | de Fougerolles et al. |
| 2016/0194368 A1 | 7/2016 | Hoge et al. |
| 2016/0194625 A1 | 7/2016 | Hoge et al. |
| 2016/0346363 A1 | 12/2016 | Tchou-Wong et al. |
| 2017/0189497 A1 | 7/2017 | Do et al. |
| 2017/0247704 A1 | 8/2017 | Bergsma et al. |
| 2018/0051299 A9 | 2/2018 | Byrne et al. |
| 2018/0251571 A1 | 9/2018 | Armstrong et al. |
| 2019/0071495 A1 | 3/2019 | Heartlein et al. |
| 2019/0169618 A1 | 6/2019 | Garcia et al. |
| 2019/0211314 A1 | 7/2019 | DeRosa et al. |
| 2019/0241897 A1 | 8/2019 | Bergsma et al. |
| 2020/0046752 A1 | 2/2020 | Heartlein et al. |
| 2020/0231989 A1 | 7/2020 | Rebar |

FOREIGN PATENT DOCUMENTS

| | | |
|---|---|---|
| EP | 2 449 106 | 5/2012 |
| EP | 2 338 478 A1 | 6/2013 |
| EP | 2 823 809 A1 | 1/2015 |
| WO | WO2003/092598 A2 | 11/2003 |
| WO | WO2004/011647 A1 | 2/2004 |
| WO | WO2004/064750 A2 | 8/2004 |
| WO | WO2005/026372 A1 | 3/2005 |
| WO | WO2005/077333 A2 | 8/2005 |
| WO | WO2005/115481 A1 | 12/2005 |
| WO | WO2005/121348 A1 | 12/2005 |
| WO | WO2009/127060 A1 | 10/2006 |
| WO | WO2010/042877 A1 | 4/2010 |
| WO | WO2011/141705 A1 | 11/2011 |
| WO | WO2012/019168 A1 | 2/2012 |
| WO | WO2012/135805 A2 | 10/2012 |
| WO | WO2012/170930 A1 | 12/2012 |
| WO | WO2013/039857 A1 | 3/2013 |
| WO | WO2013/039861 A2 | 3/2013 |
| WO | WO2013/090186 A1 | 6/2013 |
| WO | WO2013/101690 A1 | 7/2013 |
| WO | WO2013/126803 A1 | 8/2013 |
| WO | WO2013/130161 A1 | 9/2013 |
| WO | WO2013/134530 A1 | 9/2013 |
| WO | WO2013/151663 A1 | 10/2013 |
| WO | WO2013/151664 A1 | 10/2013 |
| WO | WO2013/151666 A2 | 10/2013 |
| WO | WO2013/151667 A1 | 10/2013 |

(56) References Cited

FOREIGN PATENT DOCUMENTS

| WO | WO2013/151668 A2 | 10/2013 |
| WO | WO2013/151670 A2 | 10/2013 |
| WO | WO2013/151671 A1 | 10/2013 |
| WO | WO2013/151672 A2 | 10/2013 |
| WO | WO2013/151736 A2 | 10/2013 |
| WO | WO2014/089486 A1 | 6/2014 |
| WO | WO2014/113089 A2 | 7/2014 |
| WO | WO2014/144039 A1 | 9/2014 |
| WO | WO2014/144711 A1 | 9/2014 |
| WO | WO2014/144767 A1 | 9/2014 |
| WO | WO2014/152027 A1 | 9/2014 |
| WO | WO2014/152030 A1 | 9/2014 |
| WO | WO2014/152031 A1 | 9/2014 |
| WO | WO2014/152211 A1 | 9/2014 |
| WO | WO2014/152540 A1 | 9/2014 |
| WO | WO2014/153052 A2 | 9/2014 |
| WO | WO2014/158795 A1 | 10/2014 |
| WO | WO2014/159813 A1 | 10/2014 |
| WO | WO2015/006747 A2 | 1/2015 |
| WO | WO2015/011633 A1 | 4/2015 |
| WO | WO2015/048744 A2 | 4/2015 |
| WO | WO2015/051169 A2 | 4/2015 |
| WO | WO2015/051173 A2 | 4/2015 |
| WO | WO2015/058069 A1 | 4/2016 |
| WO | WO2016/054421 A1 | 4/2016 |
| WO | WO2016/071857 A1 | 5/2016 |
| WO | WO2016/077123 A1 | 5/2016 |
| WO | WO2016/077125 A1 | 5/2016 |
| WO | WO2016/100812 A1 | 6/2016 |

OTHER PUBLICATIONS

McIvor R Scott, Therapeutic Delivery of mRNA: The Medium Is the Message, Molecular Therapy, vol. 19, No. 5, May 2011 (May 2011), pp. 822-823.

Safdar et al., "Exosome-mRNA (EXERNA) therapy for Pompe disease", Molecular Genetics and Metabolism, v.117:abstract 264 (2016).

Toscano et al., "Enzyme replacement therapy in late-onset Pompe disease: a systematic literature review", J. Neurol, v.260:951-9. (2013).

10x

10x

MRNA THERAPY FOR POMPE DISEASE

RELATED APPLICATIONS

This application is a continuation of U.S. application Ser. No. 16/191,017, filed Nov. 14, 2018, which is issued as U.S. Pat. No. 11,090,368 on Aug. 17, 2021, which is a continuation of U.S. application Ser. No. 15/073,163, filed Mar. 17, 2016, which is issued as U.S. Pat. No. 10,172,924 on Jan. 8, 2019, which claims priority to U.S. Provisional Application Ser. No. 62/135,338, filed Mar. 19, 2015, the disclosure of which are hereby incorporated by reference in their entireties.

SEQUENCE LISTING

The present specification makes reference to a Sequence Listing (submitted electronically as a .txt file named "SHR_1185US3_SequenceListing" on Jul. 7, 2021). The .txt file was generated Jul. 7, 2021 and is 28,284 bytes in size. The entire contents of the Sequence Listing are herein incorporated by reference.

BACKGROUND

Pompe disease (also known as glycogen storage disease type II; acid alpha-glucosidase deficiency; acid maltase deficiency; GAA deficiency; GSD II; glycogenosis type II; glycogenosis, generalized, cardiac form; cardiomegalia glycogenica diffusa; acid maltase deficiency; AMD; or alpha-1,4-glucosidase deficiency) is an autosomal recessive metabolic genetic disorder characterized by mutations in the gene for the lysomsomal enzyme acid alpha-glucosidase (GAA) (also known as acid maltase). Mutations in the GAA gene eliminate or reduce the ability of the GAA enzyme to hydrolyze the α-1,4 and α-1,6 linkages in glycogen, maltose and isomaltose. As a result, glycogen accumulates in the lysosomes and cytoplasm of cells throughout the body leading to cell and tissue destruction. Tissues that are particularly affected include skeletal muscle and cardiac muscle. The accumulated glycogen causes progressive muscle weakness leading to cardiomegaly, ambulatory difficulties and respiratory insufficiency.

Three forms of Pompe disease have been identified, including the classic infantile-onset disease, non-classic infantile-onset disease and late onset disease. The classic infantile-onset form is characterized by muscle weakness, poor muscle tone, hepatomegaly and cardiac defects. The incidence of the disease is approximately 1 in 140,000 individuals. Patients with this form of the disease often die of heart failure in the first year of life. The non-classic infantile-onset form of the disease is characterized by delayed motor skills, progressive muscle weakness and in some instances cardiomegaly. Patients with this form of the disease often live only into early childhood due to respiratory failure. The late-onset form of the disease may present in late childhood, adolescence or adulthood and is characterized by progressive muscle weakness of the legs and trunk.

Currently, there is no cure for Pompe disease and the standard of care is enzyme replacement therapy (ERT) with supportive care for cardiomyopathy and physical therapy for muscle weakness and respiratory symptoms.

SUMMARY OF THE INVENTION

The present invention provides, among other things, improved methods and compositions for the treatment of Pompe disease based on mRNA therapy. The invention encompasses the observation that administration of an mRNA encoding a human GAA protein, encapsulated within a liposome, resulted in highly efficient and sustained protein production in vivo and successful reduction of, for example, glycogen levels in the liver and muscle, a clinically-relevant disease marker.

In one aspect, the present invention provides a method of treating Pompe disease, including administering to a subject in need of treatment a composition comprising an mRNA encoding acid alpha-glucosidase (GAA) at an effective dose and an administration interval such that at least one symptom or feature of Pompe disease is reduced in intensity, severity, or frequency or has delayed onset. In some embodiments, the mRNA is encapsulated within a liposome.

In another aspect, the present invention provides a method of treating Pompe disease, including administering to a subject in need of treatment a therapeutically effective amount of a composition comprising an mRNA encoding acid alpha-glucosidase (GAA) such that hypertrophic cardiomyopathy in the subject is treated. In some embodiments, the mRNA is encapsulated within a liposome.

In another aspect, the present invention provides compositions for treating Pompe disease comprising an mRNA encoding GAA at an effective dose amount encapsulated within a liposome.

In some embodiments, a suitable liposome comprises one or more cationic lipids, one or more non-cationic lipids, one or more cholesterol-based lipids and one or more PEG-modified lipids.

In some embodiments, the one or more cationic lipids are selected from the group consisting of C12-200, MC3, DLinDMA, DLinkC2DMA, cKK-E12, ICE (Imidazol-based), HGT5000, HGT5001, DODAC, DDAB, DMRIE, DOSPA, DOGS, DODAP, DODMA and DMDMA, DODAC, DLenDMA, DMRIE, CLinDMA, CpLinDMA, DMOBA, DOcarbDAP, DLinDAP, DLincarbDAP, DLinCDAP, KLin-K-DMA, DLin-K-XTC2-DMA, HGT4003, and combinations thereof.

In some embodiments, the one or more cationic lipids comprise a compound of formula I-c1-a:

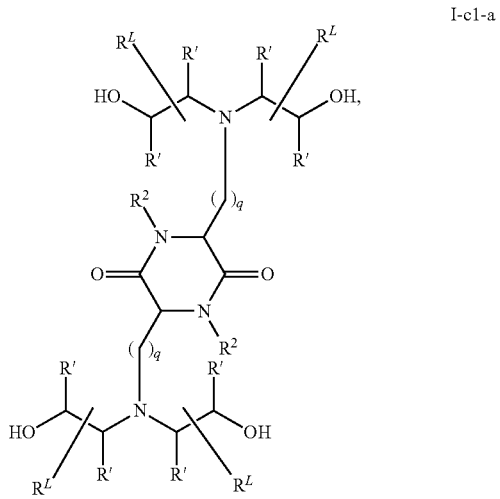

or a pharmaceutically acceptable salt thereof, wherein:
each $R^2$ independently is hydrogen or $C_{1-3}$ alkyl;
each q independently is 2 to 6;

each R' independently is hydrogen or $C_{1-3}$ alkyl;
and each $R^L$ independently is $C_{8-12}$ alkyl.

In some embodiments, the one or more cationic lipids comprise cKK-E12:

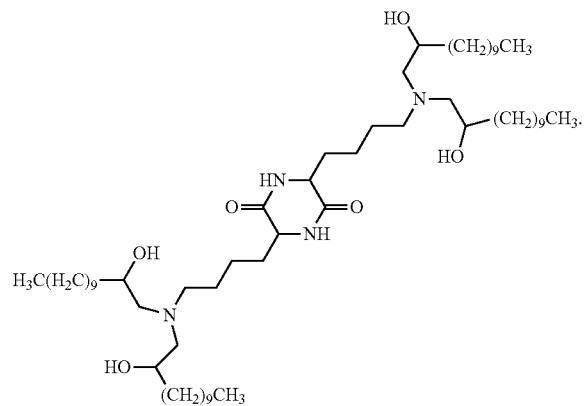

In some embodiments, the one or more non-cationic lipids suitable for the invention are selected from DSPC (1,2-distearoyl-sn-glycero-3-phosphocholine), DPPC (1,2-dipalmitoyl-sn-glycero-3-phosphocholine), DOPE (1,2-dioleyl-sn-glycero-3-phosphoethanolamine), DOPC (1,2-dioleyl-sn-glycero-3-phosphotidylcholine) DPPE (1,2-dipalmitoyl-sn-glycero-3-phosphoethanolamine), DMPE (1,2-dimyristoyl-sn-glycero-3-phosphoethanolamine), DOPG (,2-dioleoyl-sn-glycero-3-phospho-(1'-rac-glycerol)), and combinations thereof.

In some embodiments, the one or more cholesterol-based lipids are selected from cholesterol, PEGylated cholesterol and DC-Chol (N,N-dimethyl-N-ethylcarboxamidocholesterol), 1,4-bis(3-N-oleylamino-propyl)piperazine and combinations thereof.

In some embodiments, the liposome further comprises one or more PEG-modified lipids. In some embodiments, the one or more PEG-modified lipids comprise a poly(ethylene) glycol chain of up to 5 kDa in length covalently attached to a lipid with alkyl chain(s) of $C_6$-$C_{20}$ length. In some embodiments, a PEG-modified lipid is a derivatized ceramide such as N-Octanoyl-Sphingosine-1-[Succinyl(Methoxy Polyethylene Glycol)-2000]. In some embodiments, a PEG-modified or PEGylated lipid is PEGylated cholesterol or Dimyristoylglycerol (DMG)-PEG-2K.

In some embodiments, a suitable liposome comprises a combination selected from cKK-E12, DOPE, cholesterol and DMG-PEG2K; C12-200, DOPE, cholesterol and DMG-PEG2K; HGT4003, DOPE, cholesterol and DMG-PEG2K; or ICE, DOPE, cholesterol and DMG-PEG2K.

In some embodiments, cationic lipids (e.g., cKK-E12, C12-200, ICE, and/or HGT4003) constitute about 30-60% (e.g., about 30-55%, about 30-50%, about 30-45%, about 30-40%, about 35-50%, about 35-45%, or about 35-40%) of the liposome by molar ratio. In some embodiments, cationic lipids (e.g., cKK-E12, C12-200, ICE, and/or HGT4003) constitute about 30%, about 35%, about 40%, about 45%, about 50%, about 55%, or about 60% of the liposome by molar ratio.

In some embodiments, the ratio of cationic lipid(s) (e.g., cKK-E12, C12-200, ICE, and/or HGT4003) to non-cationic lipid(s) (e.g., DOPE) to cholesterol-based lipid(s) (e.g., cholesterol) to PEGylated lipid(s) (e.g., DMG-PEG2K) may be between about 30-60:25-35:20-30:1-15, respectively. In some embodiments, the ratio of cationic lipid(s) (e.g., cKK-E12, C12-200, ICE, and/or HGT4003) to non-cationic lipid(s) (e.g., DOPE) to cholesterol-based lipid(s) (e.g., cholesterol) to PEGylated lipid(s) (e.g., DMG-PEG2K) is approximately 40:30:20:10, respectively. In some embodiments, the ratio of cationic lipid(s) (e.g., cKK-E12, C12-200, ICE, and/or HGT4003) to non-cationic lipid(s) (e.g., DOPE) to cholesterol-based lipid(s) (e.g., cholesterol) to PEGylated lipid(s) (e.g., DMG-PEG2K) is approximately 40:30:25:5, respectively. In some embodiments, the ratio of cationic lipid(s) (e.g., cKK-E12, C12-200, ICE, and/or HGT4003) to non-cationic lipid(s) (e.g., DOPE) to cholesterol-based lipid(s) (e.g., cholesterol) to PEGylated lipid(s) (e.g., DMG-PEG2K) is approximately 40:32:25:3, respectively. In some embodiments, the ratio of cationic lipid(s) (e.g., cKK-E12, C12-200, ICE, and/or HGT4003) to non-cationic lipid(s) (e.g., DOPE) to cholesterol-based lipid(s) (e.g., cholesterol) to PEGylated lipid(s) (e.g., DMG-PEG2K) is approximately 50:25:20:5.

In some embodiments, the size of a liposome is determined by the length of the largest diameter of the liposome particle. In some embodiments, a suitable liposome has a size less than about 500 nm, 400 nm, 300 nm, 250 nm, 200 nm, 150 nm, 100 nm, 75 nm, or 50 nm. In some embodiments, a suitable liposome has a size less than about 100 nm, 90 nm, 80 nm, 70 nm, or 60 nm. In a particular embodiment, the liposome has a size less than about 100 nm.

In some embodiments, the mRNA is administered at a dose ranging from about 0.1-5.0 mg/kg body weight, for example about 0.1-4.5, 0.1-4.0, 0.1-3.5, 0.1-3.0, 0.1-2.5, 0.1-2.0, 0.1-1.5, 0.1-1.0, 0.1-0.5, 0.1-0.3, 0.3-5.0, 0.3-4.5, 0.3-4.0, 0.3-3.5, 0.3-3.0, 0.3-2.5, 0.3-2.0, 0.3-1.5, 0.3-1.0, 0.3-0.5, 0.5-5.0, 0.5-4.5, 0.5-4.0, 0.5-3.5, 0.5-3.0, 0.5-2.5, 0.5-2.0, 0.5-1.5, or 0.5-1.0 mg/kg body weight. In some embodiments, the mRNA is administered at a dose of or less than about 5.0, 4.5, 4.0, 3.5, 3.0, 2.5, 2.0, 1.5, 1.0, 0.8, 0.6, 0.5, 0.4, 0.3, 0.2, or 0.1 mg/kg body weight. In a particular embodiment, the mRNA is administered at a dose of about 1.0 mg/kg.

In some embodiments, the provided composition is administered intravenously. In some embodiments, the provided composition is administered intramuscularly. In particular embodiments, the intramuscular administration is to a muscle selected from the group consisting of skeletal muscle, smooth muscle and cardiac muscle. In some embodiments, the provided composition is administered via pulmonary delivery. In certain embodiments, pulmonary delivery is performed by aerosolization, inhalation, nebulization or instillation. In some embodiments, the provided composition is formulated as respirable particles, nebulizable lipid, or inhalable dry powder.

In some embodiments, the provided composition is administered once daily, once a week, twice a week, twice a month, once a month. In some embodiments, provided the composition is administered once every 7 days, once every 10 days, once every 14 days, once every 28 days or once every 30 days.

In some embodiments, a therapeutically effective dose, when administered regularly, results in GAA protein expression in the liver. In some embodiments, a therapeutically effective dose, when administered regularly, results in GAA protein expression in a muscle tissue or a muscle cell. The muscle tissue may be, for example, skeletal muscle, smooth muscle, cardiac muscle and combinations thereof. The muscle cell may be, for example, a myocyte, a myotube, a myoblast, a cardiomyocyte, a cardiomyoblast and combinations thereof. In some embodiments, a therapeutically effective dose, when administered regularly, results in GAA protein detection in serum.

In some embodiments, a therapeutically effective dose of the provided composition, when administered regularly, results in an increased hepatic GAA protein level in a subject as compared to a baseline hepatic GAA protein level before treatment. In some embodiments, a therapeutically effective dose of the provided composition, when administered regularly, results in an increased muscle GAA protein level in a subject as compared to a baseline muscle GAA protein level before treatment. In some embodiments, the muscle is skeletal muscle (e.g., striated muscle, voluntary muscle), smooth muscle (e.g., visceral muscle, involuntary muscle) or cardiac muscle. In some embodiments, a therapeutically effective dose of the provided composition, when administered regularly, results in a reduced muscle glycogen level in a subject as compared to a baseline muscle glycogen level before treatment. In some embodiments, a therapeutically effective dose of the provided composition, when administered regularly, results in a reduced liver glycogen level in a subject as compared to a baseline liver glycogen level before treatment. In some embodiments, a therapeutically effective dose of the provided composition, when administered regularly, results in a reduced serum creatine kinase level in a subject as compared to a baseline serum creatine kinase level before treatment. In some embodiments, a therapeutically effective dose of the provided composition, when administered regularly, results in a reduced urinary glucose tetrasaccharide, (Glcα1-6Glcα1-4Glcα1-4Glc ($Glc_4$) level in a subject as compared to a baseline $Glc_4$ level before treatment. In some embodiments, a therapeutically effective dose of the provided composition, when administered regularly, results in a reduced serum aspartate transaminase (e.g., AST, aspartate aminotransferase, serum, glutamic oxaloacetic transaminase) level in a subject as compared to a baseline AST level before treatment. In some embodiments, a therapeutically effective dose of the provided composition, when administered regularly, results in a reduced serum alanine transaminase (e.g., ALT, alanine aminotransferase, serum glutamic-pyruvic transaminase) level in a subject as compared to a baseline ALT level before treatment. In some embodiments, a therapeutically effective dose of the provided composition, when administered regularly, results in a reduced serum lactate dehydrogenase (e.g., LDH, lactic dehydrogenase) level in a subject as compared to a baseline LDH level before treatment. In some embodiments, a therapeutically effective dose of the provided composition, when administered regularly, results in an increased GAA enzyme activity level in biological sample as compared to a baseline GAA enzyme activity level before treatment.

In some embodiments, administering the provided composition results in an increased GAA protein level in the liver of a subject as compared to a baseline level before treatment. Typically, the baseline level is measured immediately before treatment. In some embodiments, administering the provided composition results in an increased GAA protein level in the liver by at least about 10%, 20%, 30%, 40%, 50%, 60%, 70%, 80%, 90%, or 95% as compared to a baseline level before treatment. In some embodiments, administering the provided composition results in an increased GAA protein level in the liver as compared to a GAA protein level in the liver of subjects who are not treated.

In some embodiments, administering the provided composition results in an increased GAA protein level in skeletal muscle of a subject as compared to a baseline level before treatment. Typically, the baseline level is measured immediately before treatment. In some embodiments, administering the provided composition results in an increased GAA protein level in skeletal muscle by at least about 10%, 20%, 30%, 40%, 50%, 60%, 70%, 80%, 90%, or 95% as compared to a baseline level before treatment. In some embodiments, administering the provided composition results in an increased GAA protein level in skeletal muscle as compared to a GAA protein level in skeletal muscle of subjects who are not treated.

In some embodiments, administering the provided composition results in an increased GAA protein level in cardiac muscle of a subject as compared to a baseline level before treatment. Typically, the baseline level is measured immediately before treatment. In some embodiments, administering the provided composition results in an increased GAA protein level in cardiac muscle by at least about 10%, 20%, 30%, 40%, 50%, 60%, 70%, 80%, 90%, or 95% as compared to a baseline level before treatment. In some embodiments, administering the provided composition results in an increased GAA protein level in cardiac muscle as compared to a GAA protein level in cardiac muscle of subjects who are not treated.

In some embodiments, administering the provided composition results in an increased level of GAA protein in smooth muscle of a subject as compared to a baseline level before treatment. Typically, the baseline level is measured immediately before treatment. In some embodiments, administering the provided composition results in an increased GAA protein level in smooth muscle by at least about 10%, 20%, 30%, 40%, 50%, 60%, 70%, 80%, 90%, or 95% as compared to a baseline level before treatment. In some embodiments, administering the provided composition results in an increased GAA protein level in smooth muscle as compared to a GAA protein level in smooth muscle of subjects who are not treated.

In some embodiments, administering the provided composition results in an increased level of GAA protein in a muscle cell of a subject as compared to a baseline level before treatment. Typically, the baseline level is measured immediately before treatment. In some embodiments the muscle cell is a myocyte, a myotube, a myoblast, a cardiomyocyte or a cardiomyoblast. In some embodiments, administering the provided composition results in an increased GAA protein level in the muscle cell by at least about 10%, 20%, 30%, 40%, 50%, 60%, 70%, 80%, 90%, or 95% as compared to a baseline level before treatment. In some embodiments, administering the provided composition results in an increased GAA protein level in a muscle cell as compared to a GAA protein level in a muscle cell of subjects who are not treated.

In some embodiments, administering the provided composition results in an increased level of GAA protein in a liver cell (e.g., a hepatocyte, a sinusoid lining cell) of a subject as compared to a baseline level before treatment. Typically, the baseline level is measured immediately before treatment. In some embodiments, administering the provided composition results in an increased GAA protein level in the liver cell by at least about 10%, 20%, 30%, 40%, 50%, 60%, 70%, 80%, 90%, or 95% as compared to a baseline level before treatment. In some embodiments, administering the provided composition results in an increased GAA protein level in a liver cell as compared to a GAA protein level in a liver cell of subjects who are not treated.

In some embodiments, administering the provided composition results in an increased GAA protein level in plasma or serum of a subject as compared to a baseline level before treatment. Typically, the baseline level is measured immediately before treatment. In some embodiments, administering the provided composition results in an increased GAA protein level in plasma or serum by at least about 10%, 20%, 30%, 40%, 50%, 60%, 70%, 80%, 90%, or 95% as compared to a baseline level before treatment. In some embodiments, administering the provided composition results in an increased GAA protein level in plasma or serum as compared to a GAA protein level in plasma or serum of subjects who are not treated In some embodiments, administering the provided composition results in a reduced serum creatine kinase level in a subject as compared to a baseline level before treatment. Typically, the baseline level is measured immediately before treatment. In some embodiments, administering the provided composition results in a reduced serum creatine kinase level by at least about 10%, 20%, 30%, 40%, 50%, 60%, 70%, 80%, 90%, or 95% as compared to the baseline serum creatine kinase level immediately before treatment. In some embodiments, administering the provided composition results in a reduced serum creatine kinase level to less than about 2000 IU/L, 1500 IU/L, 1000 IU/L, 750 IU/L, 500 IU/L, 250 IU/L, 100 IU/L, 90 IU/L, 80 IU/L, 70 IU/L or 60 IU/L. In some embodiments, administering the provided composition results in a reduced serum creatine kinase level as compared to a serum creatine kinase level in subjects who are not treated.

In some embodiments, administering the provided composition results in a reduced urinary $Glc_4$ level in a subject as compared to a baseline level before treatment. Typically, the baseline level is measured immediately before treatment. In some embodiments, administering the provided composition results in a reduced urinary $Glc_4$ level by at least about 10%, 20%, 30%, 40%, 50%, 60%, 70%, 80%, 90%, or 95% as compared to a baseline level immediately before treatment. In some embodiments, administering the provided composition results in a reduced urinary $Glc_4$ level to less than about 100 mmol $Glc_4$/mol creatinine, 90 mmol $Glc_4$/mol creatinine, 80 mmol $Glc_4$/mol creatinine, 70 mmol $Glc_4$/mol creatinine, 60 mmol $Glc_4$/mol creatinine, 50 mmol $Glc_4$/mol creatinine, 40 mmol $Glc_4$/mol creatinine, 30 mmol $Glc_4$/mol creatinine or 20 mmol $Glc_4$/mol creatinine. In some embodiments, administering the provided composition results in a reduced urinary $Glc_4$ level as compared to a urinary $Glc_4$ level in subjects who are not treated.

In some embodiments, administering the provided composition results in a reduced muscle glycogen level in a subject as compared to a baseline level before treatment. Typically, the baseline level is measured immediately before treatment. In some embodiments, administering the provided composition results in a reduced muscle glycogen level by at least about 10%, 20%, 30%, 40%, 50%, 60%, 70%, 80%, 90%, or 95% as compared to a baseline level immediately before treatment. In some embodiments, administering the provided composition results in a reduced muscle glycogen level as compared to a muscle glycogen level in subjects who are not treated. In particular embodiments, the muscle is skeletal muscle, smooth muscle or cardiac muscle.

In some embodiments, administering the provided composition results in a reduced liver glycogen level in a subject as compared to a baseline level before treatment. Typically, the baseline level is measured immediately before treatment. In some embodiments, administering the provided composition results in a reduced liver glycogen level by at least about 10%, 20%, 30%, 40%, 50%, 60%, 70%, 80%, 90%, or 95% as compared to a baseline level immediately before treatment. In some embodiments, administering the provided composition results in a reduced liver glycogen level as compared to a liver glycogen level in subjects who are not treated.

In some embodiments, administering the provided composition results in a reduced serum aspartate transaminase (AST) level in a subject as compared to a baseline level before treatment. Typically, the baseline level is measured immediately before treatment. In some embodiments, administering the provided composition results in a reduced serum AST level by at least about 10%, 20%, 30%, 40%, 50%, 60%, 70%, 80%, 90%, or 95% as compared to a baseline level immediately before treatment. In some embodiments, administering the provided composition results in a reduced serum AST level to less than about 600 IU/L, 500 IU/L, 400 IU/L, 300 IU/L, 200 IU/L, 100 IU/L, 50 IU/L, 25 IU/L, 20 IU/L or 10 IU/L. In some embodiments, administering the provided composition results in a reduced serum AST level as compared to a serum AST level in subjects who are not treated.

In some embodiments, administering the provided composition results in a reduced serum alanine transaminase (ALT) level in a subject as compared to a baseline level before treatment. Typically, the baseline level is measured immediately before treatment. In some embodiments, administering the provided composition results in a reduced serum ALT level by at least about 10%, 20%, 30%, 40%, 50%, 60%, 70%, 80%, 90%, or 95% as compared to a baseline level immediately before treatment. In some embodiments, administering the provided composition results in a reduced serum ALT level to less than about 1000 IU/L, 900 IU/L, 800 IU/L, 700 IU/L, 600 IU/L, 500 IU/L, 400 IU/L, 300 IU/L, 200 IU/L, 100 IU/L, 50 IU/L, 25 IU/L, 20 IU/L or 10 IU/L. In some embodiments, administering the provided composition results in a reduced serum ALT level as compared to a serum ALT level in subjects who are not treated.

In some embodiments, administering the provided composition results in a reduced serum lactate dehydrogenase (LDH) level in a subject as compared to a baseline level before treatment. Typically, the baseline level is measured immediately before treatment. In some embodiments, administering the provided composition results in a reduced serum lactate dehydrogenase LDH level by at least about 10%, 20%, 30%, 40%, 50%, 60%, 70%, 80%, 90%, or 95% as compared to a baseline level immediately before treatment. In some embodiments, administering the provided composition results in a reduced serum LDH level to less than about 2000 IU/L, 1500 IU/L, 1000 IU/L, 900 IU/L, 800 IU/L, 700 IU/L, 600 IU/L, 500 IU/L, 400 IU/L, 300 IU/L, 200 IU/L or 100 IU/L. In some embodiments, administering the provided composition results in a reduced serum LDH level as compared to a serum LDH levels in subjects who are not treated.

In some embodiments, administering the provided composition results in an increased GAA enzyme activity in a biological sample from a subject as compared to a baseline level before treatment. Typically, the baseline level is measured immediately before treatment. Biological samples include, for example, whole blood, serum, plasma, urine and tissue samples (e.g., muscle, liver, skin fibroblasts). In some embodiments, administering the provided composition results in an increased GAA enzyme activity by at least about 10%, 20%, 30%, 40%, 50%, 60%, 70%, 80%, 90%, or 95% as compared to a baseline level immediately before treatment. In some embodiments, administering the provided composition results in an increased GAA enzyme activity as compared to a GAA enzyme activity in subjects who are not treated.

In some embodiments, administering the provided composition results in an increased GAA mRNA expression level in a biological sample from a subject as compared to a baseline expression level before treatment. Typically, the baseline level is measured immediately before treatment. Biological samples include, for example, whole blood, serum, plasma, urine and tissue samples (e.g., muscle, liver, skin fibroblasts). In some embodiments, administering the provided composition results in an increased GAA mRNA expression level by at least about 10%, 20%, 30%, 40%, 50%, 60%, 70%, 80%, 90%, or 95% as compared to the baseline level immediately before treatment. In some embodiments, administering the provided composition results in an increased GAA mRNA expression level as compared to a GAA mRNA expression level in subjects who are not treated.

In some embodiments, the mRNA is codon optimized. In some embodiments, the codon-optimized mRNA comprises SEQ ID NO: 3 (corresponding to codon-optimized human GAA mRNA sequences). In some embodiments, the mRNA comprises the 5' UTR sequence of SEQ ID NO: 8 (corresponding to 5' UTR sequence X). In some embodiments, the mRNA comprises the 3' UTR sequence of SEQ ID NO: 9 (corresponding to a 3' UTR sequence Y). In some embodiments, the mRNA comprises the 3' UTR sequence of SEQ ID NO: 10 (corresponding to a 3' UTR sequence Y). In some embodiments, the codon-optimized mRNA comprises SEQ ID NO: 11 or SEQ ID NO: 12 (corresponding to codon-optimized human GAA mRNA sequence with 5' UTR and 3' UTR sequences).

In some embodiments, the mRNA comprises one or more modified nucleotides. In some embodiments, the one or more modified nucleotides comprise pseudouridine, N-1-methyl-pseudouridine, 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, 0(6)-methylguanine, and/or 2-thiocytidine. In some embodiments, the mRNA is unmodified.

In one aspect, the present invention provides a composition for treating Pompe disease, comprising an mRNA encoding acid alpha-glucosidase (GAA) at an effective dose amount encapsulated within a liposome, wherein the liposome comprises a cationic lipid cKK-E12:

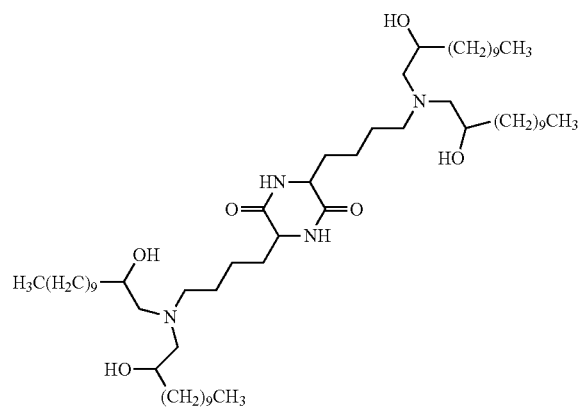

In a one embodiment, the liposome further comprises one or more non-cationic lipids, one or more cholesterol-based lipids, and one or more PEG-modified lipids. In some embodiments, the one or more non-cationic lipids are selected from DSPC (1,2-distearoyl-sn-glycero-3-phosphocholine), DPPC (1,2-dipalmitoyl-sn-glycero-3-phosphocholine), DOPE (1,2-dioleyl-sn-glycero-3-phosphoethanolamine), DOPC (1,2-dioleyl-sn-glycero-3-phosphotidylcholine) DPPE (1,2-dipalmitoyl-sn-glycero-3-phosphoethanolamine), DMPE (1,2-dimyristoyl-sn-glycero-3-phosphoethanolamine), DOPG (,2-dioleoyl-sn-glycero-3-phospho-(1'-rac-glycerol)).

In another embodiment, the one or more cholesterol-based lipids are selected from cholesterol and/or PEGylated cholesterol. In a further embodiment, the one or more PEG-modified lipids comprise a poly(ethylene) glycol chain of up to 5 kDa in length covalently attached to a lipid with alkyl chain(s) of $C_6$-$C_{20}$ length.

In another embodiment, the liposome comprises cKK-E12, DOPE, cholesterol and DMG-PEG2K. In a particular embodiment, the cationic lipid constitutes about 30-50% of the liposome by molar ratio. In another embodiment, the cationic lipid constitutes about 40% of the liposome by molar ratio.

In another embodiment, the ratio of cKK-E12:DOPE:cholesterol:DMG-PEG2K is approximately 40:30:20:10 by molar ratio. In a particular embodiment, the ratio of cKK-E12:DOPE:cholesterol:DMG-PEG2K is approximately 40:30:25:5 by molar ratio. In yet another embodiment, the ratio of cKK-E12:DOPE:cholesterol:DMG-PEG2K is approximately 40:32:25:3 by molar ratio. In one embodiment, the liposome has a size less than about 100 nm.

In one embodiment, the composition is formulated for intravenous administration. In another embodiment, the composition is formulated for intramuscular administration. In another embodiment, the mRNA comprises SEQ ID NO: 3. In a further embodiment, the mRNA further comprises the 5' UTR sequence of SEQ ID NO: 8. In yet another embodiment, the mRNA further comprises the 3' UTR sequence of SEQ ID NO: 9 or SEQ ID NO: 10. In a particular embodiment, the mRNA comprises SEQ ID NO: 11 or SEQ ID NO: 12.

In one aspect, the present invention provides a composition for treating Pompe disease comprising an mRNA encoding acid alpha-glucosidase (GAA) at an effective dose amount encapsulated within a liposome, wherein the mRNA comprises SEQ ID NO: 3, and further wherein the liposome comprises cationic or non-cationic lipid, cholesterol-based lipid and PEG-modified lipid.

In in one aspect, the present invention provides a composition for treating Pompe disease comprising an mRNA encoding acid alpha-glucosidase (GAA) at an effective dose amount encapsulated within a liposome, wherein the mRNA comprises SEQ ID NO: 11 or SEQ ID NO: 12, and further wherein the liposome comprises cationic or non-cationic lipid, cholesterol-based lipid and PEG-modified lipid.

Other features, objects, and advantages of the present invention are apparent in the detailed description, drawings and claims that follow. It should be understood, however, that the detailed description, the drawings, and the claims, while indicating embodiments of the present invention, are given by way of illustration only, not limitation. Various changes and modifications within the scope of the invention will become apparent to those skilled in the art.

BRIEF DESCRIPTION OF THE DRAWING

The patent or application file contains at least one drawing executed in color. Copies of this patent or patent application publication with color drawing(s) will be provided by the Office upon request and payment of the necessary fee.

The drawings are for illustration purposes only not for limitation.

DEFINITIONS

Figure 1A:
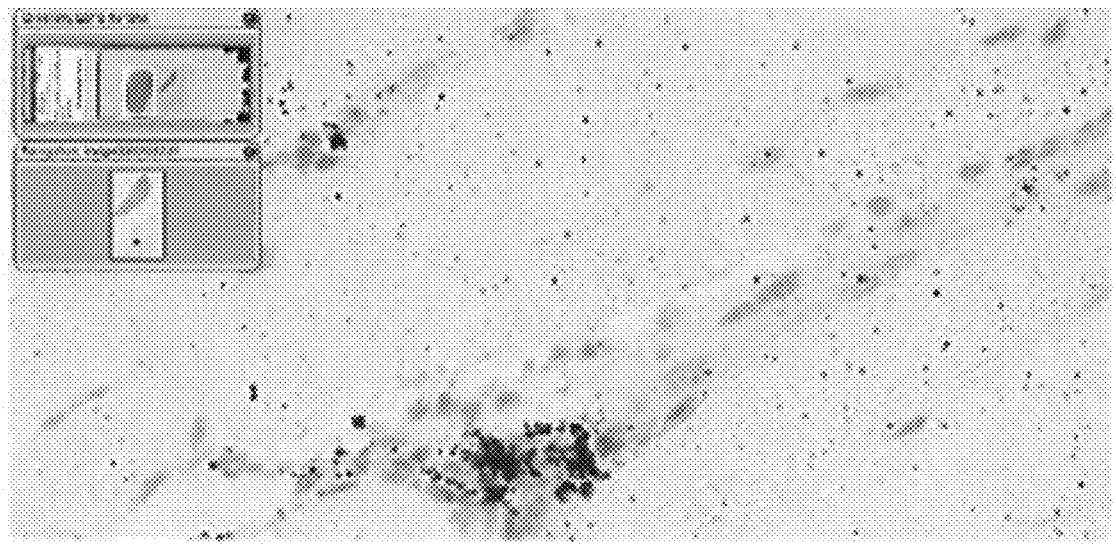
FIGS. 1A-1B depict exemplary GAA mRNA detection by in situ hybridization in muscle tissue from mice 6 hours (FIG. 1A) or 12 hours (FIG. 1B) after treatment with a single 1.0 mg/kg intravenous dose of GAA mRNA encapsulated lipid nanoparticles.

In order for the present invention to be more readily understood, certain terms are first defined below. Additional definitions for the following terms and other terms are set forth throughout the specification. The publications and other reference materials referenced herein to describe the background of the invention and to provide additional detail regarding its practice are hereby incorporated by reference.

Alkyl: As used herein, "alkyl" refers to a radical of a straight-chain or branched saturated hydrocarbon group having from 1 to 15 carbon atoms ("$C_{1-15}$ alkyl"). In some embodiments, an alkyl group has 1 to 3 carbon atoms ("$C_{1-3}$ alkyl"). Examples of $C_{1-3}$ alkyl groups include methyl ($C_1$), ethyl ($C_2$), n-propyl ($C_3$), and isopropyl ($C_3$). In some embodiments, an alkyl group has 8 to 12 carbon atoms ("$C_{8-12}$ alkyl"). Examples of $C_{8-12}$ alkyl groups include, without limitation, n-octyl ($C_8$), n-nonyl ($C_9$), n-decyl ($C_{10}$), n-undecyl ($C_{11}$), n-dodecyl (Cu) and the like. The prefix "n-" (normal) refers to unbranched alkyl groups. For example, n-$C_8$ alkyl refers to —$(CH_2)_7CH_3$, n-$C_{10}$ alkyl refers to —$(CH_2)_9CH_3$, etc.

Amino acid: As used herein, term "amino acid," in its broadest sense, refers to any compound and/or substance that can be incorporated into a polypeptide chain. In some embodiments, an amino acid has the general structure $H_2N$—C(H)(R)—COOH. In some embodiments, an amino acid is a naturally occurring amino acid. In some embodiments, an amino acid is a synthetic amino acid; in some embodiments, an amino acid is a d-amino acid; in some embodiments, an amino acid is an l-amino acid. "Standard amino acid" refers to any of the twenty standard l-amino acids commonly found in naturally occurring peptides. "Nonstandard amino acid" refers to any amino acid, other than the standard amino acids, regardless of whether it is prepared synthetically or obtained from a natural source. As used herein, "synthetic amino acid" encompasses chemically modified amino acids, including but not limited to salts, amino acid derivatives (such as amides), and/or substitutions. Amino acids, including carboxy- and/or amino-terminal amino acids in peptides, can be modified by methylation, amidation, acetylation, protecting groups, and/or substitution with other chemical groups that can change the peptide's circulating half-life without adversely affecting their activity. Amino acids may participate in a disulfide bond. Amino acids may comprise one or posttranslational modifications, such as association with one or more chemical entities (e.g., methyl groups, acetate groups, acetyl groups, phosphate groups, formyl moieties, isoprenoid groups, sulfate groups, polyethylene glycol moieties, lipid moieties, carbohydrate moieties, biotin moieties, etc.). The term "amino acid" is used interchangeably with "amino acid residue," and may refer to a free amino acid and/or to an amino acid residue of a peptide. It will be apparent from the context in which the term is used whether it refers to a free amino acid or a residue of a peptide.

Animal: As used herein, the term "animal" refers to any member of the animal kingdom. In some embodiments, "animal" refers to humans, at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In some embodiments, an animal may be a transgenic animal, genetically-engineered animal, and/or a clone.

Approximately or about: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Biologically active: As used herein, the phrase "biologically active" refers to a characteristic of any agent that has activity in a biological system, and particularly in an organism. For instance, an agent that, when administered to an organism, has a biological effect on that organism, is considered to be biologically active.

Delivery: As used herein, the term "delivery" encompasses both local and systemic delivery. For example, delivery of mRNA encompasses situations in which an mRNA is delivered to a target tissue and the encoded protein is expressed and retained within the target tissue (also referred to as "local distribution" or "local delivery"), and situations in which an mRNA is delivered to a target tissue and the encoded protein is expressed and secreted into patient's circulation system (e.g., serum) and systematically distributed and taken up by other tissues (also referred to as "systemic distribution" or "systemic delivery).

Expression: As used herein, "expression" of a nucleic acid sequence refers to translation of an mRNA into a polypeptide, assemble multiple polypeptides into an intact protein (e.g., enzyme) and/or post-translational modification of a polypeptide or fully assembled protein (e.g., enzyme). In this application, the terms "expression" and "production," and grammatical equivalent, are used inter-changeably.

Functional: As used herein, a "functional" biological molecule is a biological molecule in a form in which it exhibits a property and/or activity by which it is characterized.

Half-life: As used herein, the term "half-life" is the time required for a quantity such as nucleic acid or protein concentration or activity to fall to half of its value as measured at the beginning of a time period.

Improve, increase, or reduce: As used herein, the terms "improve," "increase" or "reduce," or grammatical equivalents, indicate values that are relative to a baseline measurement, such as a measurement in the same individual prior to initiation of the treatment described herein, or a measurement in a control subject (or multiple control subject) in the absence of the treatment described herein. A "control subject" is a subject afflicted with the same form of disease as the subject being treated, who is about the same age as the subject being treated.

In Vitro: As used herein, the term "in vitro" refers to events that occur in an artificial environment, e.g., in a test tube or reaction vessel, in cell culture, etc., rather than within a multi-cellular organism.

In Vivo: As used herein, the term "in vivo" refers to events that occur within a multi-cellular organism, such as a human and a non-human animal. In the context of cell-based systems, the term may be used to refer to events that occur within a living cell (as opposed to, for example, in vitro systems).

Isolated: As used herein, the term "isolated" refers to a substance and/or entity that has been (1) separated from at least some of the components with which it was associated when initially produced (whether in nature and/or in an experimental setting), and/or (2) produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. As used herein, calculation of percent purity of isolated substances and/or entities should not include excipients (e.g., buffer, solvent, water, etc.).

Local distribution or delivery: As used herein, the terms "local distribution," "local delivery," or grammatical equivalent, refer to tissue specific delivery or distribution. Typically, local distribution or delivery requires a protein (e.g., enzyme) encoded by mRNAs be translated and expressed intracellularly or with limited secretion that avoids entering the patient's circulation system.

messenger RNA (mRNA): As used herein, the term "messenger RNA (mRNA)" refers to a polynucleotide that encodes at least one polypeptide. mRNA as used herein encompasses both modified and unmodified RNA. mRNA may contain one or more coding and non-coding regions. mRNA can be purified from natural sources, produced using recombinant expression systems and optionally purified, chemically synthesized, etc. Where appropriate, e.g., in the case of chemically synthesized molecules, mRNA can comprise nucleoside analogs such as analogs having chemically modified bases or sugars, backbone modifications, etc. An mRNA sequence is presented in the 5' to 3' direction unless otherwise indicated. In some embodiments, an mRNA is or comprises natural nucleosides (e.g., adenosine, guanosine, cytidine, uridine); nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, 0(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages).

Muscle cell or muscle tissue: As used herein, the term "muscle cell" or "muscle tissue" in its broadest sense, refers to a cell or group of cells derived from muscle, including, but not limited to cells and tissues derived from skeletal muscle (e.g., striated muscle, voluntary muscle); smooth muscle (e.g., visceral muscle, involuntary muscle) from the digestive tract, urinary bladder and blood vessels; and cardiac muscle. The term refers to muscle cells in vivo and in vitro. The term also includes differentiated and undifferentiated, or nondifferentiated, muscle cells, such as myocytes, myotubes, myoblasts, cardiomyocytes and cardiomyoblasts.

Nucleic acid: As used herein, the term "nucleic acid," in its broadest sense, refers to any compound and/or substance that is or can be incorporated into a polynucleotide chain. In some embodiments, a nucleic acid is a compound and/or substance that is or can be incorporated into a polynucleotide chain via a phosphodiester linkage. In some embodiments, "nucleic acid" refers to individual nucleic acid residues (e.g., nucleotides and/or nucleosides). In some embodiments, "nucleic acid" refers to a polynucleotide chain comprising individual nucleic acid residues. In some embodiments, "nucleic acid" encompasses RNA as well as single and/or double-stranded DNA and/or cDNA.

Patient: As used herein, the term "patient" or "subject" refers to any organism to which a provided composition may be administered, e.g., for experimental, diagnostic, prophylactic, cosmetic, and/or therapeutic purposes. Typical patients include animals (e.g., mammals such as mice, rats, rabbits, non-human primates, and/or humans). In some embodiments, a patient is a human. A human includes pre and post natal forms.

Pharmaceutically acceptable: The term "pharmaceutically acceptable" as used herein, refers to substances that, within the scope of sound medical judgment, are suitable for use in contact with the tissues of human beings and animals without excessive toxicity, irritation, allergic response, or other problem or complication, commensurate with a reasonable benefit/risk ratio.

Pharmaceutically acceptable salt: Pharmaceutically acceptable salts are well known in the art. For example, S. M. Berge et al., describes pharmaceutically acceptable salts in detail in J. Pharmaceutical Sciences (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}$ alkyl$)_4$ salts. Representative alkali or alkaline earth metal salts include sodium, lithium, potassium, calcium, magnesium, and the like. Further pharmaceutically acceptable salts include, when appropriate, non-toxic ammonium. quaternary ammonium, and amine cations formed using counterions such as halide, hydroxide, carboxylate, sulfate, phosphate, nitrate, sulfonate and aryl sulfonate. Further pharmaceutically acceptable salts include salts formed from the quarternization of an amine using an appropriate electrophile, e.g., an alkyl halide, to form a quarternized alkylated amino salt.

Systemic distribution or delivery: As used herein, the terms "systemic distribution," "systemic delivery," or grammatical equivalent, refer to a delivery or distribution mechanism or approach that affect the entire body or an entire organism. Typically, systemic distribution or delivery is accomplished via body's circulation system, e.g., blood stream. Compared to the definition of "local distribution or delivery."

Subject: As used herein, the term "subject" refers to a human or any non-human animal (e.g., mouse, rat, rabbit, dog, cat, cattle, swine, sheep, horse or primate). A human includes pre- and post-natal forms. In many embodiments, a subject is a human being. A subject can be a patient, which refers to a human presenting to a medical provider for diagnosis or treatment of a disease. The term "subject" is used herein interchangeably with "individual" or "patient." A subject can be afflicted with or is susceptible to a disease or disorder but may or may not display symptoms of the disease or disorder.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Target tissues: As used herein, the term "target tissues" refers to any tissue that is affected by a disease to be treated. In some embodiments, target tissues include those tissues that display disease-associated pathology, symptom, or feature.

Therapeutically effective amount: As used herein, the term "therapeutically effective amount" of a therapeutic agent means an amount that is sufficient, when administered to a subject suffering from or susceptible to a disease, disorder, and/or condition, to treat, diagnose, prevent, and/or delay the onset of the symptom(s) of the disease, disorder, and/or condition. It will be appreciated by those of ordinary skill in the art that a therapeutically effective amount is typically administered via a dosing regimen comprising at least one unit dose.

Treating: As used herein, the term "treat," "treatment," or "treating" refers to any method used to partially or completely alleviate, ameliorate, relieve, inhibit, prevent, delay onset of, reduce severity of and/or reduce incidence of one or more symptoms or features of a particular disease, disorder, and/or condition. Treatment may be administered to a subject who does not exhibit signs of a disease and/or exhibits only early signs of the disease for the purpose of decreasing the risk of developing pathology associated with the disease.

DETAILED DESCRIPTION

The present invention provides, among other things, methods and compositions for treating Pompe disease based on mRNA therapy. In particular, the present invention provides methods for treating Pompe disease by administering to a subject in need of treatment a composition comprising an mRNA encoding acid alpha-glucosidase (GAA) at an effective dose and an administration interval such that at least one symptom or feature of Pome disease is reduced in intensity, severity, or frequency or has a delayed onset. The present invention further provides, methods of treating Pompe disease, comprising administering to a subject in need of treatment a therapeutically effective amount of a composition comprising an mRNA encoding acid alpha-glucosidase (GAA) such that hypertrophic cardiomyopathy in the subject is treated. In some embodiments, the mRNA is encapsulated within one or more liposomes. As used herein, the term "liposome" refers to any lamellar, multilamellar, or solid nanoparticle vesicle. Typically, a liposome as used herein can be formed by mixing one or more lipids or by mixing one or more lipids and polymer(s). Thus, the term "liposome" as used herein encompasses both lipid and polymer based nanoparticles. In some embodiments, a liposome suitable for the present invention contains cationic or non-cationic lipid(s), cholesterol-based lipid(s) and PEG-modified lipid(s).

Pompe Disease

The present invention may be used to treat a subject who is suffering from or susceptible to Pompe disease. Pompe disease is an autosomal recessive metabolic genetic disorder characterized by mutations in the gene for the enzyme acid alpha-glucosidase (GAA). The GAA enzyme is also known as: acid maltase, maltase, maltase-glucoamylase, gluoinvertase, glucosidosucrase, aglucosidase alfa, alpha-1,4-glucosidase, amyloglucosidase, glucoamylase, LYAG, LYAG_HUMAN, lysosomal alpha-glucosidase and alpha-glucosidase, acid. The GAA gene (glucosidase, alpha; acid) is also known as: acid maltase, alpha-1,4-glucosidase and alpha-gluosidase, acid. More than 200 mutations that cause Pompe disease have been identified in the GAA gene. Most of these mutations involve single amino acid substitutions and small insertions or deletions. Many of the mutations in the GAA gene likely affect the structure of the resulting protein and decrease its activity. A few of the mutations in the GAA gene lead to the production of an abnormally short version of the enzyme that cannot effectively play its role in the hydrolysis of glycogen.

Defects in the acid alpha-glucosidase enzyme reduce the ability of the cell to hydrolyze glycogen resulting in the accumulation of glycogen in cells and tissues, and in particular in the liver and muscle. The accumulation of glycogen results in cell death which manifests as progressive muscle weakness, cardiomyopathy and respiratory insufficiency.

Compositions and methods described herein may be used to treat at least one symptom or feature of Pompe disease. In particular, the compositions and methods described herein may be used to treat hypertrophic cardiomyopathy.

Acid Alpha-Glucosidase (GAA)

In some embodiments, the present invention provides methods and compositions for delivering mRNA encoding GAA to a subject for the treatment of Pompe disease. A suitable GAA mRNA encodes any full length, fragment or portion of an GAA protein which can be substituted for naturally-occurring GAA protein activity and/or reduce the intensity, severity, and/or frequency of one or more symptoms associated with Pompe disease.

In some embodiments, a suitable mRNA sequence is an mRNA sequence encoding a human GAA protein. The naturally-occurring human GAA mRNA coding sequence and the corresponding amino acid sequence are shown in Table 1:

TABLE 1

| Human GAA | |
|---|---|
| Human GAA (mRNA coding sequence) | (SEQ ID NO: 1)<br>AUGGGAGUGAGGCACCCGCCCUGCUCCCACCGGC<br>UCCUGGCCGUCUGCGCCCUCGUGUCCUUGGCAAC<br>CGCUGCACUCCUGGGGCACAACUCCUACUCCAUGAU<br>UUCCUGCUGGUUCCCCGAGAGCUGAGUGGCUCCU<br>CCCCAGUCCUGGAGGAGACUCACCCAGCUCACCA<br>GCAGGGAGCCAGCAGACCAGGGCCCCGGGAUGCC<br>CAGGCACACCCCGGCCGUCCCAGAGCAGUGCCCA<br>CACAGUGCGACGUCCCCCCCAACAGCCGCUUCGA<br>UUGCGCCCCUGACAAGGCCAUCACCCAGGAACAG<br>UGCGAGGCCCGCGGCUGUUGCUACAUCCCUGCAA<br>AGCAGGGGCUGCAGGGAGCCCAGAUGGGGCAGCC<br>CUGGUGCUUCUUCCCACCCAGCUACCCCAGCUAC<br>AAGCUGGAGAACCUGAGCUCCUCUGAAAUGGGCU<br>ACACGGCCACCCUGACCCGUACCACCCCCACCUU<br>CUUCCCCAAGGACAUCCUGACCCUGCGGCUGGAC<br>GUGAUGAUGGAGACUGAGAACCGCCUCCACUUCA<br>CGAUCAAAGAUCCAGCUAACAGGCGCUACGAGGU<br>GCCCUUGGAGACCCCGCAUGUCCACAGCCGGGCA<br>CCGUCCCCACUCUACAGCGUGGAGUUCUCCGAGG<br>AGCCCUUCGGGGUGAUCGUGCGCCGGCAGCUGGA<br>CGGCCGCGUGCUGCUGAACACGACGGUGGCGCCC<br>CUGUUCUUUGCGGACCAGUUCUUCAGCUGUCCA<br>CCUCGCUGCCCCUCGCAGUAUAUCACAGGCCUCGG<br>CGAGCACCUCAGUCCCCUGAUGCUCAGCACCAGC<br>UGGACCAGGAUCACCCUGUGGAACCGGGACCUUG<br>CGCCCACGCCCGGUGCGAACCUCUACGGGUCUCA<br>CCCUUUCUACCUGGCGCUGGAGGACGGCGGGUCG<br>GCACACGGGGUUCCUGCUAAACAGCAAUGCCA<br>UGGAUGUGGUCCUGCAGCCGAGCCCUGCCCUAAG<br>CUGGAGGUCGACAGGUGGGAUCCUGGAUGUCUAC<br>AUCUUCCUGGGCCCAGAGCCCAAGAGCGUGGUGC<br>AGCAGUACCUGGACGUUGUGGGAUACCCGUUCAU<br>GCCGCCAUACUGGGGCCUGGGCUUCCACCUGUGC<br>CGCUGGGGCUACUCCUCCACCGCUAUCACCCGCC<br>AGGUGGUGGAGAACAUGACCAGGGCCCACUUCCC<br>CCUGGACGUCCAGUGGAACGACCUGGACUACAUG<br>GACUCCCGGAGGGACUUCACGUUCAACAAGGAUG<br>GCUUCCGGGACUUCCCGGCCAUGGUGCAGGAGCU<br>GCACCAGGGCGGCCGGCGCUACAUGAUGAUCGUG<br>GAUCCUGCCAUCAGCAGCUCGGGCCCUGCCGGGA<br>GCUACAGGCCCUACGACGAGGGUCUGCGGAGGGG<br>GGUUUUCAUCACCAACGAGACCGGCCAGCCGCUG<br>AUUGGGAAGGUAUGGCCGGGUCCACUGCCUUCC<br>CCGACUUCACCAACCCCACAGCCUCGGGCCCUGGUG<br>GGAGGCAUGGUGGCUGAGUUCCAUGACCAGGUG<br>CCCUUCGACGGCAUGUGGAUUGACAUGAACGAGC<br>CUUCCAACUUCAUCAGGGGCUCUGAGGACGGCUG<br>CCCCAACAAUGAGCUGGAGAACCCCACCCUACGUG<br>CCUGGGGUGGUUGGGGGGACCCUCCAGGCGGCCA |

TABLE 1-continued

| Human GAA | |
|---|---|
| | CCAUCUGUGCCUCCAGCCACCAGUUUCUCUCCAC<br>ACACUACAACCUGCACAACCUCUACGGCCUGACC<br>GAAGCCAUCGCCUCCCACAGGGCGCUGGUGAAGG<br>CUCGGGGGACACGCCCAUUUGUGAUCUCCCGCUC<br>GACCUUUGCUGGCCACGGCCGAUACGCCGGCCAC<br>UGGACGGGGGACGUGUGGAGCUCCUGGGAGCAGC<br>UCGCCUCCUCCGUGCCAGAAAUCCUGCAGUUUAA<br>CCUGCUGGGGGUGCCUCUGGUCGGGGCCGACGUC<br>UGCGGCUUCCUGGGCAACACCUCAGAGGAGCUGU<br>GUGUGCGCUGGACCCAGCUGGGGGCCUUCUACCC<br>CUUCAUGCGGAACCACAACAGCCUGCUCAGUCUG<br>CCCCAGGAGCCGUACAGCUUCAGCGAGCCGGCCC<br>AGCAGGCCAUGAGGAAGGCCCUCACCCUGCGCUA<br>CGCACUCCUCCCCCACCUCUACACACUGUUCCAC<br>CAGGCCCACGUCGCGGGGAGACCGUGGCCCGGC<br>CCCUCUUCCUGGAGUUCCCCAAGGACUCUAGCAC<br>CUGGACUGUGGACCACCAGCUCCUGUGGGGGAG<br>GCCCUGCUCAUCACCCCAGUGCUCCAGGCCGGGA<br>AGGCCGAAGUGACUGGCUACUUCCCCUUGGGCAC<br>AUGGUACGACCUGCAGACGGUGCCAGUAGAGGCC<br>CUUGGCAGCCUCCCACCCCCACCUGCAGCUCCCC<br>GUGAGCCAGCCAUCCACAGCGAGGGGCAGUGGGU<br>GACGCUGCCGGCCCCCUGGACACCAUCAACGUC<br>CACCUCCGGGCUGGGUACAUCAUCCCCCUGCAGG<br>GCCCUGGCCUCACAACCACAGAGUCCCGCCAGCA<br>GCCCAUGGCCCUGGCUGUGGCCCUGACCAAGGGU<br>GGGGAGGCCCGAGGGGAGCUGUUCUGGGACGAUG<br>GAGAGAGCCUGGAAGUGCUGGAGCGAGGGGCCUA<br>CACACAGGUCAUCUUCCUGGCCAGGAAUAACACG<br>AUCGUGAAUGAGCUGGUACGUGUGACCAGUGAGG<br>GAGCUGGCCUGCAGCUGCAGAAGGUGACUGUCCU<br>GGGCGUGGCCACGGCGCCCCAGCAGGUCCUCUCC<br>AACGGUGUCCCUGUCUCCAACUUCACCUACAGCC<br>CCGACACCAAGGUCCUGGACAUCUGUGUCUCGCU<br>GUUGAUGGGAGAGCAGUUUCUCGUCAGCUGGUGU<br>UAG |
| Human GAA (Amino Acid Sequence) | (SEQ ID NO: 2)<br>MGVRHPPCSHRLLAVCALVSLATAALLGHILLHD<br>FLLVPRELSGSSPVLEETHPAHQQGASRPGPRDA<br>QAHPGRPRAVPTQCDVPPNSRFDCAPDKAITQEQ<br>CEARGCCYIPAKQGLQGAQMGQPWCFFPPSYPSY<br>KLENLSSSEMGYTATLTRTTPTFFPKDILTLRLD<br>VMMETENRLHFTIKDPANRRYEVPLETPHVSRA<br>PSPLYSVEFSEEPFGVIVRRQLDGRVLLNTTVAP<br>LFFADQFLQLSTSLPSQYITGLAEHLSPLMLSTS<br>WTRITLWNRDLAPTPGANLYGSHPFYLALEDGGS<br>AHGVFLLNSNAMDVVLQPSPALSWRSTGGILDVY<br>IFLGPEPKSVVQQYLDVVGYPFMPPYWGLGFHLC<br>RWGYSSTAITRQVVENMTRAHFPLDVQWNDLDYM<br>DSRRDFTFNKDGFRDFPAMVQELHQGGRRYMMIV<br>DPAISSSGPAGSYRPYDEGLRRGVFITNETGQPL<br>IGKVWPGSTAFPDFTNPTALAWWEDMVAEFHDQV<br>PFDGMWIDMNEPSNFIRGSEDGCPNNELENPPYV<br>PGVVGGTLQAATICASSHQFLSTHYNLHNLYGLT<br>EAIASHRALVKARGTRPFVISRSTFAGHGRYAGH<br>WTGDVWSSWEQLASSVPEILQFNLLGVPLVGADV<br>CGFLGNTSEELCVRWTQLGAFYPFMRNHNSLLSL<br>PQEPYSFSEPAQQAMRKALTLRYALLPHLYTLFH<br>QAHVAGETVARPLFLEFPKDSSTWTVDHQLLWGE<br>ALLITPVLQAGKAEVTGYFPLGTWYDLQTVPVEA<br>LGSLPPPPAAPREPAIHSEGQWVTLPAPLDTINV<br>HLRAGYIIPLQGPGLTTTESRQQPMALAVALTKG<br>GEARGELFWDDGESLEVLERGAYTQVIFLARNNT<br>IVNELVRVTSEGAGLQLQKVTVLGVATAPQQVLS<br>NGVPVSNFTYSPDTKVLDICVSLLMGEQFLVSWC |

In some embodiments, a suitable mRNA is a wild-type human GAA mRNA of sequence (SEQ ID NO: 1). In some embodiments, a suitable mRNA may be a codon optimized hGAA sequence, such as the sequence shown below:

```
Codon-Optimized human GAA Coding Sequence (SEQ ID
NO: 3):
AUGGGAGUCAGACACCCGCCGUGCUCGCACAGGCUUCUGGCCGUGUGCG
CACUCGUGAGUCUGGCGACUGCUGCGUUGCUGGGGCACAUUCUUCUCCA
CGACUUUCUCUUGGUGCCCCGAGAAUUGUCGGGCUCGUCGCCGGUACUG
GAAGAAACCCACCCCGCACAUCAGCAGGGCGCGUCGCGGCCUGGUCCGA
GGGAUGCCCAGGCACAUCCCGGAAGGCCACGAGCCGUCCCGACUCAAUG
UGACGUACCUCCCAAUUCCCGGUUCGACUGUGCGCCAGACAAGGCAAUC
ACGCAAGAGCAGUGCGAAGCCCGUGGAUGCUGCUAUAUUCCGGCGAAGC
AGGGACUUCAGGGAGCCCAGAUGGGGCAGCCCUGGUGUUUCUUCCCGCC
UUCCUAUCCCUCAUAUAAGCUGGAGAAUUUGUCGUCCUCGGAAAUGGGG
UAUACCGCUACUCUUACGAGAACCACCCCCACAUUCUUUCCGAAGGACA
UCCUUACUCUGCGGCUCGACGUGAUGAUGGAGACAGAAAAUAGGCUGCA
UUUCACGAUCAAAGACCCGGCGAACCGGAGAUAUGAGGUUCCGCUUGAG
ACUCCCCACGUUCACUCUCGUGCGCCUUCACCCUUGUACUCCGUGGAGU
UCUCGGAAGAACCGUUCGGGGUGAUCGUCAGACGUCAACUUGAUGGUAG
GGUAUUGCUGAACACAACGGUCGCCCCCUUGUUUUUCGCCGACCAGUUU
CUGCAGCUUUCGACAUCGCUGCCGUCCCAGUAUAUCACAGGGCUCGCGG
AGCAUCUUUCACCCCUCAUGCUGAGCACGAGCUGGACACGGAUUACGCU
CUGGAACAGGGAUCUCGCGCCGACGCCCGGAGCGAAUUGUAUGGGUCG
CAUCCCUUCUACCUCGCAUUGGAAGACGGGGGUUCCGCGCACGGAGUAU
UCCUGCUUAAUUCUAAUGCGAUGGACGUUGUCUUGCAGCCCUCCCCUGC
UUUGUCGUGGCGUUCCACGGGGGGCAUUUUGGACGUUUACAUCUUUUUG
GGACCCGAGCCAAAGAGCGUAGUGCAGCAGUAUUGGAUGUAGUGGGCU
ACCCCUUCAUGCCGCCUUAUUGGGGACUGGGGUUCCAUCUCUGCCGCUG
GGGGUACUCUUCGACCGCGAUCACCCGCCAGGUGGUCGAGAACAUGACC
AGAGCACAUUUCCCUUUGGACGUGCAGUGGAAUGAUUUGGAUUACAUGG
AUAGCCGAAGAGACUUCACGUUCAAUAAGGACGGGUUUAGAGAUUUUCC
CGCGAUGGUGCAAGAAUUGCACCAGGGUGGCGCAGAUACAUGAUGAUC
GUCGAUCCCGCCAUCAGCAGCUCGGGACCAGCGGGGAGUUACCGGCCUU
ACGAUGAGGGACUUAGGAGAGGCGUCUUUAUCACGAACGAAACAGGUCA
GCCGCUCAUUGGUAAAGUGUGGCCUGGAUCAACGGCCUUUCCCGACUUC
ACGAAUCCCACAGCCCUCGCCUGGUGGGAAGACAUGGUGGCGGAGUUUC
ACGACCAAGUACCGUUUGAUGGGAUGUGGAUUGAUAUGAACGAACCCUC
AAACUUUAUUCGCGGCUCGGAAGAUGGAUGCCCGAAUAAUGAGCUUGAG
AAUCCCCGUAUGUGCCAGGGGUGGUAGGUGGGACGCUCCAGGCCGCUA
CGAUCUGUGCGUCAUCACAUCAGUUCUUGUCAACGCACUACAACUUGCA
CAAUCUUUACGGUUUGACUGAAGCCAUCGCUUCGCAUCGCGCGCUGGUC
AAAGCGCGUGGUACGCGACCCUUCGUUAUUUCUCGGUCCACAUUUGCCG
```

```
GGCACGGUCGGUAUGCCGGACACUGGACGGGAGAUGUCUGGUCUAGCUG
GGAGCAGCUCGCGUCGAGCGUACCGGAGAUCCUCCAGUUCAAUCUUUUG
GGAGUUCCGCUCGUCGGCGCUGACGUGUGCGGUUUUCUCGGAAACACAU
CAGAAGAGCUUUGCGUACGCUGGACACAGCUCGGUGCGUUUUACCCCUU
UAUGAGAAACCAUAACUCGUUGCUCUCACUCCCUCAAGAGCCGUACAGU
UUUUCGGAGCCUGCGCAACAGGCGAUGCGGAAGGCAUUGACACUUCGCU
AUGCACUGCUCCCGCAUCUCUAUACUCUGUUCCAUCAGGCCCAUGUGGC
UGGAGAAACGGUGGCGAGGCCCCUGUUCUUGGAGUUCCCAAAGAUAGU
UCCACAUGGACCGUGGAUCACCAGUUGCUGUGGGGAGAGGCGCUUCUGA
UCACUCCGGUACUUCAGGCGGGUAAAGCGGAAGUCACUGGGUAUUCCC
GCUUGGGACCUGGUACGACCUUCAGACUGUCCCAGUAGAAGCCCUCGGA
AGCCUGCCACCUCCCCUGCUGCACCCCGCGAGCCUGCAAUCCAUAGCG
AGGGCCAGUGGGUAACGUUGCCAGCCCCACUGGAUACCAUCAAUGUCCA
CCUCAGGGCGGGUUACAUUAUCCCUCUCCAAGGCCCUGGGUUGACCACC
ACAGAGUCGCGCCAGCAGCCAAUGGCACUUGCGGUCGCAUUGACGAAAG
GGGGUGAAGCCCGAGGGGAACUGUUUUGGGAUGACGGGGAAAGCCUUGA
GGUGCUGGAACGGGGAGCGUACACACAAGUCAUUUUCUUGGCCAGGAAC
AACACUAUUGUCAACGAGUUGGUGCGCGUGACCUCUGAGGGUGCCGGAC
UGCAACUGCAGAAGGUCACGGUCCUCGGAGUGGCGACAGCACCCCAACA
GGUCCUUAGUAACGGAGUACCUGUCUCGAACUUUACAUACUCCCCGGAC
ACGAAGGUGCUCGACAUCUGUGUGUCGCUGCUUAUGGGGGAACAGUUUC
UCGUGAGCUGGUGCUAG
```

Additional exemplary mRNA sequences are described in the Examples section below, for example, SEQ ID NO: 11 and SEQ ID NO: 12, both of which include 5' and 3' untranslated regions framing a codon-optimized GAA-encoding mRNA.

In some embodiments, a suitable mRNA sequence may be an mRNA sequence a homolog or an analog of human GAA protein. For example, a homologue or an analogue of human GAA protein may be a modified human GAA protein containing one or more amino acid substitutions, deletions, and/or insertions as compared to a wild-type or naturally-occurring human GAA protein while retaining substantial GAA protein activity. In some embodiments, an mRNA suitable for the present invention encodes an amino acid sequence at least 50%, 55%, 60%, 65%, 70%, 75%, 80%, 85%, 90%, 91%, 92%, 93%, 94%, 95%, 96%, 97%, 98%, 99% or more homologous to SEQ ID NO: 2. In some embodiments, an mRNA suitable for the present invention encodes a protein substantially identical to human GAA protein. In some embodiments, an mRNA suitable for the present invention encodes an amino acid sequence at least 50%, 55%, 60%, 65%, 70%, 75%, 80%, 85%, 90%, 91%, 92%, 93%, 94%, 95%, 96%, 97%, 98%, 99% or more identical to SEQ ID NO: 2. In some embodiments, an mRNA suitable for the present invention encodes a fragment or a portion of human GAA protein. In some embodiments, an mRNA suitable for the present invention encodes a fragment or a portion of human GAA protein, wherein the fragment or portion of the protein still maintains GAA activity similar to that of the wild-type protein. In some embodiments, an mRNA suitable for the present invention has a nucleotide sequence at least 50%, 55%, 60%, 65%, 70%, 75%, 80%, 85%, 90%, 91%, 92%, 93%, 94%, 95%, 96%, 97%, 98%, 99% or more identical to SEQ ID NO: 1, SEQ ID NO: 3, SEQ ID NO: 11 or SEQ ID NO: 12.

In some embodiments, a suitable mRNA encodes a fusion protein comprising a full length, fragment or portion of an GAA protein fused to another protein (e.g., an N or C terminal fusion). In some embodiments, the protein fused to the mRNA encoding a full length, fragment or portion of an GAA protein encodes a signal or a cellular targeting sequence.

Delivery Vehicles

According to the present invention, mRNA encoding an GAA protein (e.g., a full length, fragment or portion of an GAA protein) as described herein may be delivered as naked RNA (unpackaged) or via delivery vehicles. As used herein, the terms "delivery vehicle," "transfer vehicle," "nanoparticle" or grammatical equivalent, are used interchangeably.

In some embodiments, mRNAs encoding an GAA protein may be delivered via a single delivery vehicle. In some embodiments, mRNAs encoding an GAA protein may be delivered via one or more delivery vehicles each of a different composition. According to various embodiments, suitable delivery vehicles include, but are not limited to polymer based carriers, such as polyethyleneimine (PEI), lipid nanoparticles and liposomes, nanoliposomes, ceramide-containing nanoliposomes, proteoliposomes, both natural and synthetically-derived exosomes, natural, synthetic and semi-synthetic lamellar bodies, nanoparticulates, calcium phosphor-silicate nanoparticulates, calcium phosphate nanoparticulates, silicon dioxide nanoparticulates, nanocrystalline particulates, semiconductor nanoparticulates, poly(D-arginine), sol-gels, nanodendrimers, starch-based delivery systems, micelles, emulsions, niosomes, multi-domain-block polymers (vinyl polymers, polypropyl acrylic acid polymers, dynamic polyconjugates), dry powder formulations, plasmids, viruses, calcium phosphate nucleotides, aptamers, peptides and other vectorial tags.

Liposomal Delivery Vehicles

In some embodiments, a suitable delivery vehicle is a liposomal delivery vehicle, e.g., a lipid nanoparticle. As used herein, liposomal delivery vehicles, e.g., lipid nanoparticles, are usually characterized as microscopic vesicles having an interior aqua space sequestered from an outer medium by a membrane of one or more bilayers. Bilayer membranes of liposomes are typically formed by amphiphilic molecules, such as lipids of synthetic or natural origin that comprise spatially separated hydrophilic and hydrophobic domains (Lasic, Trends Biotechnol., 16: 307-321, 1998). Bilayer membranes of the liposomes can also be formed by amphophilic polymers and surfactants (e.g., polymerosomes, niosomes, etc.). In the context of the present invention, a liposomal delivery vehicle typically serves to transport a desired mRNA to a target cell or tissue.

Cationic Lipids

In some embodiments, liposomes may comprise one or more cationic lipids. As used herein, the phrase "cationic lipid" refers to any of a number of lipid species that have a net positive charge at a selected pH, such as physiological pH. Several cationic lipids have been described in the literature, many of which are commercially available. Particularly suitable cationic lipids for use in the compositions and methods of the invention include those described in international patent publications WO 2010/053572 (and particularly, C1 2-200 described at paragraph [00225]) and WO 2012/170930, both of which are incorporated herein by reference. In certain embodiments, the compositions and methods of the invention employ a lipid nanoparticles comprising an ionizable cationic lipid described in U.S. provisional patent application 61/617,468, filed Mar. 29, 2012 (incorporated herein by reference), such as, e.g, (15Z, 18Z)-N,N-dimethyl-6-(9Z, 12Z)-octadeca-9, 12-dien-1-yl) tetracosa-15,18-dien-1-amine (HGT5000), (15Z, 18Z)-N,N-dimethyl-6-((9Z, 12Z)-octadeca-9, 12-dien-1-yl)tetracosa-4, 15,18-trien-1-amine (HGT5001), and (15Z,18Z)-N,N-dimethyl-6-((9Z, 12Z)-octadeca-9, 12-dien-1-yl)tetracosa-5, 15, 18-trien-1-amine (HGT5002).

In some embodiments, provided liposomes include a cationic lipid described in WO 2013/063468 and in U.S. provisional application entitled "Lipid Formulations for Delivery of Messenger RNA" filed concurrently with the present application on even date, both of which are incorporated by reference herein.

In some embodiments, a cationic lipid comprises a compound of formula I-c1-a:

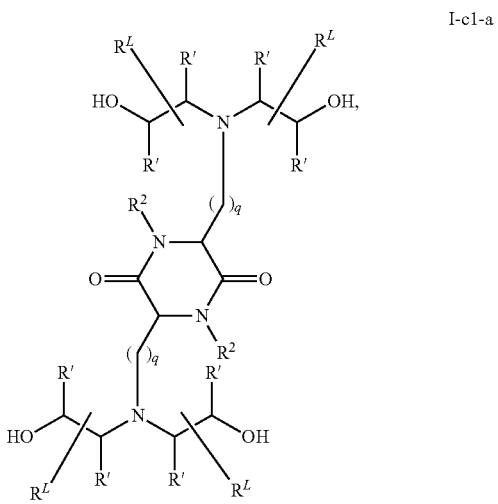

or a pharmaceutically acceptable salt thereof, wherein:
each $R^2$ independently is hydrogen or $C_{1-3}$ alkyl;
each q independently is 2 to 6;
each R' independently is hydrogen or $C_{1-3}$ alkyl;
and each $R^L$ independently is $C_{8-12}$ alkyl.

In some embodiments, each $R^2$ independently is hydrogen, methyl or ethyl. In some embodiments, each $R^2$ independently is hydrogen or methyl. In some embodiments, each $R^2$ is hydrogen.

In some embodiments, each q independently is 3 to 6. In some embodiments, each q independently is 3 to 5. In some embodiments, each q is 4.

In some embodiments, each R' independently is hydrogen, methyl or ethyl. In some embodiments, each R' independently is hydrogen or methyl. In some embodiments, each R' independently is hydrogen.

In some embodiments, each $R^L$ independently is $C_{8-12}$ alkyl. In some embodiments, each $R^L$ independently is n-$C_{8-12}$ alkyl. In some embodiments, each $R^L$ independently is $C_{9-11}$ alkyl. In some embodiments, each $R^L$ independently is n-$C_{9-11}$ alkyl. In some embodiments, each $R^L$ independently is $C_{10}$ alkyl. In some embodiments, each $R^L$ independently is n-$C_{10}$ alkyl.

In some embodiments, each $R^2$ independently is hydrogen or methyl; each q independently is 3 to 5; each R' independently is hydrogen or methyl; and each $R^L$ independently is $C_{8-12}$ alkyl.

In some embodiments, each $R^2$ is hydrogen; each q independently is 3 to 5; each R' is hydrogen; and each $R^L$ independently is $C_{8-12}$ alkyl.

In some embodiments, each $R^2$ is hydrogen; each q is 4; each R' is hydrogen; and each $R^L$ independently is $C_{8-12}$ alkyl.

In some embodiments, a cationic lipid comprises a compound of formula I-g:

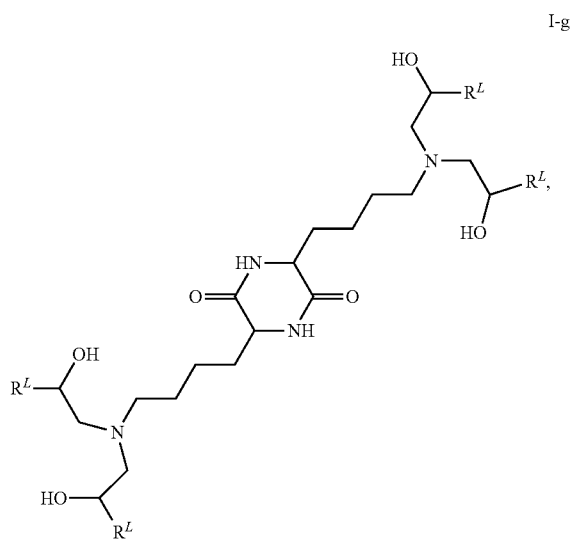

I-g or a pharmaceutically acceptable salt thereof, wherein each $R^L$ independently is $C_{8-12}$ alkyl. In some embodiments, each $R^L$ independently is n-$C_{8-12}$ alkyl. In some embodiments, each $R^L$ independently is $C_{9-11}$ alkyl. In some embodiments, each $R^L$ independently is n-$C_{9-11}$ alkyl. In some embodiments, each $R^L$ independently is $C_{10}$ alkyl. In some embodiments, each $R^L$ is n-$C_{10}$ alkyl.

In particular embodiments, provided liposomes include a cationic lipid cKK-E12, or (3,6-bis(4-(bis(2-hydroxydodecyl)amino)butyl)piperazine-2,5-dione). Structure of cKK-E12 is shown below:

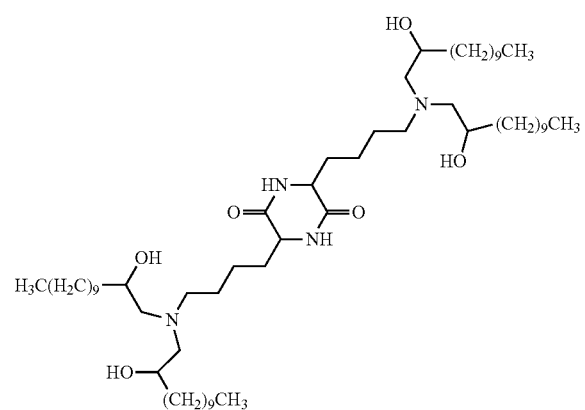

In some embodiments, the one or more cationic lipids may be N-[1-(2,3-dioleyloxy)propyl]-N,N,N-trimethylammonium chloride or "DOTMA" (Feigner et al. (Proc. Nat'l Acad. Sci. 84, 7413 (1987); U.S. Pat. No. 4,897,355). DOTMA can be formulated alone or can be combined with the neutral lipid, dioleoylphosphatidyl-ethanolamine or "DOPE" or other cationic or non-cationic lipids into a liposomal transfer vehicle or a lipid nanoparticle, and such liposomes can be used to enhance the delivery of nucleic acids into target cells. Other suitable cationic lipids include, for example, 5-carboxyspermylglycinedioctadecylamide or "DOGS," 2,3-dioleyloxy-N-[2(spermine-carboxamido) ethyl]-N,N-dimethyl-1-propanaminium or "DOSPA" (Behr et al. Proc. Nat.'l Acad. Sci. 86, 6982 (1989); U.S. Pat. Nos. 5,171,678; 5,334,761), 1,2-Dioleoyl-3-Dimethylammonium-Propane or "DODAP", 1,2-Dioleoyl-3-Trimethylammonium-Propane or "DOTAP".

Additional exemplary cationic lipids also include 1,2-distearyloxy-N,N-dimethyl-3-aminopropane or "DSDMA", 1,2-dioleyloxy-N,N-dimethyl-3-aminopropane or "DODMA", 1,2-dilinoleyloxy-N,N-dimethyl-3-aminopropane or "DLinDMA", 1,2-dilinolenyloxy-N,N-dimethyl-3-aminopropane or "DLenDMA", N-dioleyl-N,N-dimethylammonium chloride or "DODAC", N,N-distearyl-N,N-dimethylarnrnonium bromide or "DDAB", N-(1,2-dimyristyloxyprop-3-yl)-N,N-dimethyl-N-hydroxyethyl ammonium bromide or "DMRIE", 3-dimethylamino-2-(cholest-5-en-3-beta-oxybutan-4-oxy)-1-(cis,cis-9,12-octadecadienoxy)propane or "CLinDMA", 2-[5'-(cholest-5-en-3-beta-oxy)-3'-oxapentoxy)-3-dimethy 1-1-(cis,cis-9',1-2'-octadecadienoxy)propane or "CpLinDMA", N,N-dimethyl-3,4-dioleyloxybenzylamine or "DMOBA", 1,2-N,N'-dioleylcarbamyl-3-dimethylaminopropane or "DOcarbDAP", 2,3-Dilinoleoyloxy-N,N-dimethylpropylamine or "DLinDAP", 1,2-N,N'-Dilinoleylcarbamyl-3-dimethylaminopropane or "DLincarbDAP", 1,2-Dilinoleoylcarbamyl-3-dimethylaminopropane or "DLinCDAP", 2,2-dilinoleyl-4-dimethylaminomethyl-[1,3]-dioxolane or "DLin--DMA", 2,2-dilinoleyl-4-dimethylaminoethyl-[1,3]-dioxolane or "DLin-K-XTC2-DMA", and 2-(2,2-di((9Z, 12Z)-octadeca-9,12-dien-1-yl)-1,3-dioxolan-4-yl)-N,N-dimethylethanamine (DLin-KC2-DMA)) (See, WO 2010/042877; Semple et al., Nature Biotech. 28: 172-176 (2010)), or mixtures thereof. (Heyes, J., et al., J Controlled Release 107: 276-287 (2005); Morrissey, D V., et al., Nat. Biotechnol. 23(8): 1003-1007 (2005); PCT Publication WO2005/121348A1). In some embodiments, one or more of the cationic lipids comprise at least one of an imidazole, dialkylamino, or guanidinium moiety.

In some embodiments, the one or more cationic lipids may be chosen from XTC (2,2-Dilinoleyl-4-dimethylaminoethyl-[1,3]-dioxolane), MC3 ((((6Z,9Z,28Z,31Z)-heptatriaconta-6,9,28,31-tetraen-19-yl 4-(dimethylamino)butanoate), ALNY-100 ((3aR,5s,6aS)-N,N-dimethyl-2,2-di((9Z, 12Z)-octadeca-9,12-dienyl)tetrahydro-3aH-cyclopenta[d] [1,3]dioxol-5-amine)), NC98-5 (4,7,13-tris(3-oxo-3-(undecylamino)propyl)-N1,N16-diundecyl-4,7,10,13-tetraazahexadecane-1,16-diamide), DODAP (1,2-dioleyl-3-dimethylammonium propane), HGT4003 (WO 2012/170889, the teachings of which are incorporated herein by reference in their entirety), ICE (WO 2011/068810, the teachings of which are incorporated herein by reference in their entirety), HGT5000 (U.S. Provisional Patent Application No. 61/617, 468, the teachings of which are incorporated herein by reference in their entirety) or HGT5001 (cis or trans) (Provisional Patent Application No. 61/617,468), aminoalcohol lipidoids such as those disclosed in WO2010/053572, DOTAP (1,2-dioleyl-3-trimethylammonium propane), DOTMA (1,2-di-O-octadecenyl-3-trimethylammonium propane), DLinDMA (Heyes, J.; Palmer, L.; Bremner, K.; MacLachlan, I. "Cationic lipid saturation influences intracellular delivery of encapsulated nucleic acids" J. Contr. Rel. 2005, 107, 276-287), DLin-KC2-DMA (Semple, S.C. et al.

"Rational Design of Cationic Lipids for siRNA Delivery" Nature Biotech. 2010, 28, 172-176), C12-200 (Love, K. T. et al. "Lipid-like materials for low-dose in vivo gene silencing" PNAS 2010, 107, 1864-1869).

In some embodiments, the percentage of cationic lipid in a liposome may be greater than 10%, greater than 20%, greater than 30%, greater than 40%, greater than 50%, greater than 60%, or greater than 70%. In some embodiments, cationic lipid(s) constitute(s) about 30-50% (e.g., about 30-45%, about 30-40%, about 35-50%, about 35-45%, or about 35-40%) of the liposome by weight. In some embodiments, the cationic lipid (e.g., cKK-E12) constitutes about 30%, about 35%, about 40%, about 45%, or about 50% of the liposome by molar ratio.

Non-Cationic/Helper Lipids

In some embodiments, provided liposomes contain one or more non-cationic ("helper") lipids. As used herein, the phrase "non-cationic lipid" refers to any neutral, zwitterionic or anionic lipid. As used herein, the phrase "anionic lipid" refers to any of a number of lipid species that carry a net negative charge at a selected H, such as physiological pH. Non-cationic lipids include, but are not limited to, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoylphosphatidylcholine (POPC), palmitoyloleoyl-phosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, 1-stearoyl-2-oleoyl-phosphatidyethanolamine (SOPE), or a mixture thereof.

In some embodiments, such non-cationic lipids may be used alone, but are preferably used in combination with other excipients, for example, cationic lipids. In some embodiments, the non-cationic lipid may comprise a molar ratio of about 5% to about 90%, or about 10% to about 70% of the total lipid present in a liposome. In some embodiments, a non-cationic lipid is a neutral lipid, i.e., a lipid that does not carry a net charge in the conditions under which the composition is formulated and/or administered. In some embodiments, the percentage of non-cationic lipid in a liposome may be greater than 5%, greater than 10%, greater than 20%, greater than 30%, or greater than 40%.

Cholesterol-Based Lipids

In some embodiments, provided liposomes comprise one or more cholesterol-based lipids. For example, suitable cholesterol-based cationic lipids include, for example, DC-Choi (N,N-dimethyl-N-ethylcarboxamidocholesterol), 1,4-bis(3-N-oleylamino-propyl)piperazine (Gao, et al. Biochem. Biophys. Res. Comm. 179, 280 (1991); Wolf et al. BioTechniques 23, 139 (1997); U.S. Pat. No. 5,744,335), or ICE. In some embodiments, the cholesterol-based lipid may comprise a molar ration of about 2% to about 30%, or about 5% to about 20% of the total lipid present in a liposome. In some embodiments, The percentage of cholesterol-based lipid in the lipid nanoparticle may be greater than 5, %, 10%, greater than 20%, greater than 30%, or greater than 40%.

PEGylated Lipids

In some embodiments, provided liposomes comprise one or more PEGylated lipids. For example, the use of polyethylene glycol (PEG)-modified phospholipids and derivatized lipids such as derivatized ceramides (PEG-CER), including N-Octanoyl-Sphingosine-1-[Succinyl(Methoxy Polyethylene Glycol)-2000] (C8 PEG-2000 ceramide) is also contemplated by the present invention in combination with one or more of the cationic and, in some embodiments, other lipids together which comprise the liposome. Contemplated PEG-modified lipids include, but are not limited to, a polyethylene glycol chain of up to 5 kDa in length covalently attached to a lipid with alkyl chain(s) of $C_6$-$C_{20}$ length. In some embodiments, a PEG-modified or PEGylated lipid is PEGylated cholesterol or PEG-2K. The addition of such components may prevent complex aggregation and may also provide a means for increasing circulation lifetime and increasing the delivery of the lipid-nucleic acid composition to the target cell, (Klibanov et al. (1990) FEBS Letters, 268 (1): 235-237), or they may be selected to rapidly exchange out of the formulation in vivo (see U.S. Pat. No. 5,885,613).

In some embodiments, particularly useful exchangeable lipids are PEG-ceramides having shorter acyl chains (e.g., $C_{14}$ or $C_{18}$). The PEG-modified phospholipid and derivitized lipids of the present invention may comprise a molar ratio from about 0% to about 15%, about 0.5% to about 15%, about 1% to about 15%, about 4% to about 10%, or about 2% of the total lipid present in the liposome.

According to various embodiments, the selection of cationic lipids, non-cationic lipids and/or PEG-modified lipids which comprise the lipid nanoparticle, as well as the relative molar ratio of such lipids to each other, is based upon the characteristics of the selected lipid(s), the nature of the intended target cells, the characteristics of the mRNA to be delivered. Additional considerations include, for example, the saturation of the alkyl chain, as well as the size, charge, pH, pKa, fusogenicity and toxicity of the selected lipid(s). Thus the molar ratios may be adjusted accordingly.

Polymers

In some embodiments, a suitable delivery vehicle is formulated using a polymer as a carrier, alone or in combination with other carriers including various lipids described herein. Thus, in some embodiments, liposomal delivery vehicles, as used herein, also encompass polymer containing nanoparticles. Suitable polymers may include, for example, polyacrylates, polyalkycyanoacrylates, polylactide, polylactide-polyglycolide copolymers, polycaprolactones, dextran, albumin, gelatin, alginate, collagen, chitosan, cyclodextrins, protamine, PEGylated protamine, PLL, PEGylated PLL and polyethylenimine (PEI). When PEI is present, it may be branched PEI of a molecular weight ranging from 10 to 40 kDa, e.g., 25 kDa branched PEI (Sigma #408727).

A suitable liposome for the present invention may include one or more of any of the cationic lipids, non-cationic lipids, cholesterol lipids, PEGylated lipids and/or polymers described herein at various ratios. As non-limiting examples, a suitable liposome formulation may include a combination selected from cKK-E12, DOPE, cholesterol and DMG-PEG2K; C12-200, DOPE, cholesterol and DMG-PEG2K; HGT4003, DOPE, cholesterol and DMG-PEG2K; or ICE, DOPE, cholesterol and DMG-PEG2K.

In various embodiments, cationic lipids (e.g., cKK-E12, C12-200, ICE, and/or HGT4003) constitute about 30-60% (e.g., about 30-55%, about 30-50%, about 30-45%, about 30-40%, about 35-50%, about 35-45%, or about 35-40%) of the liposome by molar ratio. In some embodiments, the percentage of cationic lipids (e.g., cKK-E12, C12-200, ICE, and/or HGT4003) is or greater than about 30%, about 35%, about 40%, about 45%, about 50%, about 55%, or about 60% of the liposome by molar ratio.

In some embodiments, the ratio of cationic lipid(s) to non-cationic lipid(s) to cholesterol-based lipid(s) to PEGylated lipid(s) may be between about 30-60:25-35:20-30:1-

15, respectively. In some embodiments, the ratio of cationic lipid(s) to non-cationic lipid(s) to cholesterol-based lipid(s) to PEGylated lipid(s) is approximately 40:30:20:10, respectively. In some embodiments, the ratio of cationic lipid(s) to non-cationic lipid(s) to cholesterol-based lipid(s) to PEGylated lipid(s) is approximately 40:30:25:5, respectively. In some embodiments, the ratio of cationic lipid(s) to non-cationic lipid(s) to cholesterol-based lipid(s) to PEGylated lipid(s) is approximately 40:32:25:3, respectively. In some embodiments, the ratio of cationic lipid(s) to non-cationic lipid(s) to cholesterol-based lipid(s) to PEGylated lipid(s) is approximately 50:25:20:5.

Synthesis of mRNA mRNAs according to the present invention may be synthesized according to any of a variety of known methods. For example, mRNAs according to the present invention may be synthesized via in vitro transcription (IVT). Briefly, IVT is typically performed with a linear or circular DNA template containing a promoter, a pool of ribonucleotide triphosphates, a buffer system that may include DTT and magnesium ions, and an appropriate RNA polymerase (e.g., T3, T7 or SP6 RNA polymerase), DNAse I, pyrophosphatase, and/or RNAse inhibitor. The exact conditions will vary according to the specific application.

In some embodiments, for the preparation of mRNA according to the invention, a DNA template is transcribed in vitro. A suitable DNA template typically has a promoter, for example a T3, T7 or SP6 promoter, for in vitro transcription, followed by desired nucleotide sequence for desired mRNA and a termination signal.

Desired mRNA sequence(s) according to the invention may be determined and incorporated into a DNA template using standard methods. For example, starting from a desired amino acid sequence (e.g., an enzyme sequence), a virtual reverse translation is carried out based on the degenerated genetic code. Optimization algorithms may then be used for selection of suitable codons. Typically, the G/C content can be optimized to achieve the highest possible G/C content on one hand, taking into the best possible account the frequency of the tRNAs according to codon usage on the other hand. The optimized RNA sequence can be established and displayed, for example, with the aid of an appropriate display device and compared with the original (wild-type) sequence. A secondary structure can also be analyzed to calculate stabilizing and destabilizing properties or, respectively, regions of the RNA.

Modified mRNA

In some embodiments, mRNA according to the present invention may be synthesized as unmodified or modified mRNA. Typically, mRNAs are modified to enhance stability. Modifications of mRNA can include, for example, modifications of the nucleotides of the RNA. An modified mRNA according to the invention can thus include, for example, backbone modifications, sugar modifications or base modifications. In some embodiments, mRNAs may be synthesized from naturally occurring nucleotides and/or nucleotide analogues (modified nucleotides) including, but not limited to, purines (adenine (A), guanine (G)) or pyrimidines (thymine (T), cytosine (C), uracil (U)), and as modified nucleotides analogues or derivatives of purines and pyrimidines, such as e.g. 1-methyl-adenine, 2-methyl-adenine, 2-methylthio-N-6-isopentenyl-adenine, N6-methyl-adenine, N6-isopentenyl-adenine, 2-thio-cytosine, 3-methyl-cytosine, 4-acetyl-cytosine, 5-methyl-cytosine, 2,6-diaminopurine, 1-methyl-guanine, 2-methyl-guanine, 2,2-dimethyl-guanine, 7-methyl-guanine, inosine, 1-methyl-inosine, pseudouracil (5-uracil), dihydro-uracil, 2-thio-uracil, 4-thio-uracil, 5-carboxymethylaminomethyl-2-thio-uracil, 5-(carboxyhydroxymethyl)-uracil, 5-fluoro-uracil, 5-bromo-uracil, 5-carboxymethylaminomethyl-uracil, 5-methyl-2-thio-uracil, 5-methyl-uracil, N-uracil-5-oxyacetic acid methyl ester, 5-methylaminomethyl-uracil, 5-methoxyaminomethyl-2-thio-uracil, 5'-methoxycarbonylmethyl-uracil, 5-methoxy-uracil, uracil-5-oxyacetic acid methyl ester, uracil-5-oxyacetic acid (v), 1-methyl-pseudouracil, queosine, .beta.-D-mannosyl-queosine, wybutoxosine, and phosphoramidates, phosphorothioates, peptide nucleotides, methylphosphonates, 7-deazaguanosine, 5-methylcytosine and inosine. The preparation of such analogues is known to a person skilled in the art e.g., from the U.S. Pat. Nos. 4,373,071, 4,401,796, 4,415,732, 4,458,066, 4,500,707, 4,668,777, 4,973,679, 5,047,524, 5,132,418, 5,153,319, 5,262,530 and 5,700,642, the disclosures of which are incorporated by reference in their entirety.

In some embodiments, mRNAs (e.g., GAA-encoding mRNAs) may contain RNA backbone modifications. Typically, a backbone modification is a modification in which the phosphates of the backbone of the nucleotides contained in the RNA are modified chemically. Exemplary backbone modifications typically include, but are not limited to, modifications from the group consisting of methylphosphonates, methylphosphoramidates, phosphoramidates, phosphorothioates (e.g. cytidine 5'-O-(1-thiophosphate)), boranophosphates, positively charged guanidinium groups etc., which means by replacing the phosphodiester linkage by other anionic, cationic or neutral groups.

In some embodiments, mRNAs (e.g., GAA-encoding mRNAs) may contain sugar modifications. A typical sugar modification is a chemical modification of the sugar of the nucleotides it contains including, but not limited to, sugar modifications chosen from the group consisting of 2'-deoxy-2'-fluoro-oligoribonucleotide (2'-fluoro-2'-deoxycytidine 5'-triphosphate, 2'-fluoro-2'-deoxyuridine 5'-triphosphate), 2'-deoxy-T-deamine-oligoribonucleotide (2'-amino-2'-deoxycytidine 5'-triphosphate, 2'-amino-2'-deoxyuridine 5'-triphosphate), 2'-O-alkyloligoribonucleotide, 2'-deoxy-2'-C-alkyloligoribonucleotide (T-O-methylcytidine 5'-triphosphate, 2'-methyluridine 5'-triphosphate), 2'-C-alkyloligoribonucleotide, and isomers thereof (2'-aracytidine 5'-triphosphate, 2'-arauridine 5'-triphosphate), or azidotriphosphates (2'-azido-T-deoxycytidine 5'-triphosphate, 2'-azido-2'-deoxyuridine 5'-triphosphate).

In some embodiments, mRNAs (e.g., GAA-encoding mRNAs) may contain modifications of the bases of the nucleotides (base modifications). A modified nucleotide which contains a base modification is also called a base-modified nucleotide. Examples of such base-modified nucleotides include, but are not limited to, 2-amino-6-chloropurine riboside 5'-triphosphate, 2-aminoadenosine 5'-triphosphate, 2-thiocytidine 5'-triphosphate, 2-thiouridine 5'-triphosphate, 4-thiouridine 5'-triphosphate, 5-aminoallylcytidine 5'-triphosphate, 5-aminoallyluridine 5'-triphosphate, 5-bromocytidine 5'-triphosphate, 5-bromouridine 5'-triphosphate, 5-iodocytidine 5'-triphosphate, 5-iodouridine 5'-triphosphate, 5-methylcytidine 5'-triphosphate, 5-methyluridine 5'-triphosphate, 6-azacytidine 5'-triphosphate, 6-azauridine 5'-triphosphate, 6-chloropurine riboside 5'-triphosphate, 7-deazaadenosine 5'-triphosphate, 7-deazaguanosine 5'-triphosphate, 8-azaadenosine 5'-triphosphate, 8-azidoadenosine 5'-triphosphate, benzimidazole riboside 5'-triphosphate, N1-methyladenosine 5'-triphosphate, N1-methylguanosine 5'-triphosphate, N6-methyladenosine 5'-triphosphate, 06-methylguanosine 5'-triphosphate, pseudouridine 5'-triphosphate, puromycin 5'-triphosphate or xanthosine 5'-triphosphate.

Typically, mRNA synthesis includes the addition of a "cap" on the N-terminal (5') end, and a "tail" on the C-terminal (3') end. The presence of the cap is important in providing resistance to nucleases found in most eukaryotic cells. The presence of a "tail" serves to protect the mRNA from exonuclease degradation.

Thus, in some embodiments, mRNAs (e.g., GAA-encoding mRNAs) include a 5' cap structure. A 5' cap is typically added as follows: first, an RNA terminal phosphatase removes one of the terminal phosphate groups from the 5' nucleotide, leaving two terminal phosphates; guanosine triphosphate (GTP) is then added to the terminal phosphates via a guanylyl transferase, producing a 5'5'5 triphosphate linkage; and the 7-nitrogen of guanine is then methylated by a methyltransferase. Examples of cap structures include, but are not limited to, m7G(5')ppp (5'(A,G(5')ppp(5')A and G(5')ppp(5')G.

In some embodiments, mRNAs (e.g., GAA-encoding mRNAs) include a 3' poly(A) tail structure. A poly-A tail on the 3' terminus of mRNA typically includes about 10 to 300 adenosine nucleotides (SEQ ID NO: 4) (e.g., about 10 to 200 adenosine nucleotides, about 10 to 150 adenosine nucleotides, about 10 to 100 adenosine nucleotides, about 20 to 70 adenosine nucleotides, or about 20 to 60 adenosine nucleotides). In some embodiments, mRNAs include a 3' poly(C) tail structure. A suitable poly-C tail on the 3' terminus of mRNA typically include about 10 to 200 cytosine nucleotides (SEQ ID NO: 5) (e.g., about 10 to 150 cytosine nucleotides, about 10 to 100 cytosine nucleotides, about 20 to 70 cytosine nucleotides, about 20 to 60 cytosine nucleotides, or about 10 to 40 cytosine nucleotides). The poly-C tail may be added to the poly-A tail or may substitute the poly-A tail.

In some embodiments, mRNAs include a 5' and/or 3' untranslated region. In some embodiments, a 5' untranslated region includes one or more elements that affect an mRNA's stability or translation, for example, an iron responsive element. In some embodiments, a 5' untranslated region may be between about 50 and 500 nucleotides in length.

In some embodiments, a 3' untranslated region includes one or more of a polyadenylation signal, a binding site for proteins that affect an mRNA's stability of location in a cell, or one or more binding sites for miRNAs. In some embodiments, a 3' untranslated region may be between 50 and 500 nucleotides in length or longer.

Cap Structure

In some embodiments, mRNAs include a 5' cap structure. A 5' cap is typically added as follows: first, an RNA terminal phosphatase removes one of the terminal phosphate groups from the 5' nucleotide, leaving two terminal phosphates; guanosine triphosphate (GTP) is then added to the terminal phosphates via a guanylyl transferase, producing a 5'5'5 triphosphate linkage; and the 7-nitrogen of guanine is then methylated by a methyltransferase. Examples of cap structures include, but are not limited to, m7G(5')ppp (5'(A,G (5')ppp(5')A and G(5')ppp(5')G.

Naturally occurring cap structures comprise a 7-methyl guanosine that is linked via a triphosphate bridge to the 5'-end of the first transcribed nucleotide, resulting in a dinucleotide cap of m$^7$G(5')ppp(5')N, where N is any nucleoside. In vivo, the cap is added enzymatically. The cap is added in the nucleus and is catalyzed by the enzyme guanylyl transferase. The addition of the cap to the 5' terminal end of RNA occurs immediately after initiation of transcription. The terminal nucleoside is typically a guanosine, and is in the reverse orientation to all the other nucleotides, i.e., G(5')ppp(5')GpNpNp.

A common cap for mRNA produced by in vitro transcription is m$^7$G(5')ppp(5')G, which has been used as the dinucleotide cap in transcription with T7 or SP6 RNA polymerase in vitro to obtain RNAs having a cap structure in their 5'-termini. The prevailing method for the in vitro synthesis of capped mRNA employs a pre-formed dinucleotide of the form m$^7$G(5')ppp(5')G ("m$^7$GpppG") as an initiator of transcription.

To date, a usual form of a synthetic dinucleotide cap used in in vitro translation experiments is the Anti-Reverse Cap Analog ("ARCA") or modified ARCA, which is generally a modified cap analog in which the 2' or 3' OH group is replaced with —OCH$_3$.

Additional cap analogs include, but are not limited to, a chemical structures selected from the group consisting of m$^7$GpppG, m$^7$GpppA, m$^7$GpppC; unmethylated cap analogs (e.g., GpppG); dimethylated cap analog (e.g., m$^{2,7}$GpppG), trimethylated cap analog (e.g., m$^{2,2,7}$Gppp), dimethylated symmetrical cap analogs (e.g., m$^7$Gpppm$^7$G), or anti reverse cap analogs (e.g., ARCA; m$^{7,\,2'Ome}$GpppG, m$^{7 2'd}$GpppG, m$^{7,3'Ome}$GpppG, m$^{7,3'd}$GpppG and their tetraphosphate derivatives) (see, e.g., Jemiely, J. et al., "Novel 'anti-reverse' cap analogs with superior translational properties", RNA, 9: 1108-1122 (2003)).

In some embodiments, a suitable cap is a 7-methyl guanylate ("m$^7$G") linked via a triphosphate bridge to the 5'-end of the first transcribed nucleotide, resulting in m$^7$G (5')ppp(5')N, where N is any nucleoside. A preferred embodiment of a m$^7$G cap utilized in embodiments of the invention is m$^7$G(5')ppp(5')G.

In some embodiments, the cap is a Cap0 structure. Cap0 structures lack a 2'-O-methyl residue of the ribose attached to bases 1 and 2. In some embodiments, the cap is a Cap1 structure. Cap1 structures have a 2'-O-methyl residue at base 2. In some embodiments, the cap is a Cap2 structure. Cap2 structures have a 2'-O-methyl residue attached to both bases 2 and 3.

A variety of m$^7$G cap analogs are known in the art, many of which are commercially available. These include the m$^7$GpppG described above, as well as the ARCA 3'-OCH$_3$ and 2'—OCH$_3$ cap analogs (Jemiely, J. et al., RNA, 9: 1108-1122 (2003)). Additional cap analogs for use in embodiments of the invention include N7-benzylated dinucleoside tetraphosphate analogs (described in Grudzien, E. et al., RNA, 10: 1479-1487 (2004)), phosphorothioate cap analogs (described in Grudzien-Nogalska, E., et al., RNA, 13: 1745-1755 (2007)), and cap analogs (including biotinylated cap analogs) described in U.S. Pat. Nos. 8,093,367 and 8,304,529, incorporated by reference herein.

Tail Structure

Typically, the presence of a "tail" serves to protect the mRNA from exonuclease degradation. The poly A tail is thought to stabilize natural messengers and synthetic sense RNA. Therefore, in certain embodiments a long poly A tail can be added to an mRNA molecule thus rendering the RNA more stable. Poly A tails can be added using a variety of art-recognized techniques. For example, long poly A tails can be added to synthetic or in vitro transcribed RNA using poly A polymerase (Yokoe, et al. Nature Biotechnology. 1996; 14: 1252-1256). A transcription vector can also encode long poly A tails. In addition, poly A tails can be added by transcription directly from PCR products. Poly A may also be ligated to the 3' end of a sense RNA with RNA ligase (see, e.g., Molecular Cloning A Laboratory Manual, 2nd Ed., ed. by Sambrook, Fritsch and Maniatis (Cold Spring Harbor Laboratory Press: 1991 edition)).

In some embodiments, mRNAs include a 3' poly(A) tail structure. Typically, the length of the poly A tail can be at least about 10, 50, 100, 200, 300, 400 at least 500 nucleotides (SEQ ID NO: 6). In some embodiments, a poly-A tail on the 3' terminus of mRNA typically includes about 10 to 300 adenosine nucleotides (SEQ ID NO: 4) (e.g., about 10 to 200 adenosine nucleotides, about 10 to 150 adenosine nucleotides, about 10 to 100 adenosine nucleotides, about 20 to 70 adenosine nucleotides, or about 20 to 60 adenosine nucleotides). In some embodiments, mRNAs include a 3' poly(C) tail structure. A suitable poly-C tail on the 3' terminus of mRNA typically include about 10 to 200 cytosine nucleotides (SEQ ID NO: 5) (e.g., about 10 to 150 cytosine nucleotides, about 10 to 100 cytosine nucleotides, about 20 to 70 cytosine nucleotides, about 20 to 60 cytosine nucleotides, or about 10 to 40 cytosine nucleotides). The poly-C tail may be added to the poly-A tail or may substitute the poly-A tail.

In some embodiments, the length of the poly A or poly C tail is adjusted to control the stability of a modified sense mRNA molecule of the invention and, thus, the transcription of protein. For example, since the length of the poly A tail can influence the half-life of a sense mRNA molecule, the length of the poly A tail can be adjusted to modify the level of resistance of the mRNA to nucleases and thereby control the time course of polynucleotide expression and/or polypeptide production in a target cell.

5' and 3' Untranslated Region

In some embodiments, mRNAs include a 5' and/or 3' untranslated region. In some embodiments, a 5' untranslated region includes one or more elements that affect an mRNA's stability or translation, for example, an iron responsive element. In some embodiments, a 5' untranslated region may be between about 50 and 500 nucleotides in length.

In some embodiments, a 3' untranslated region includes one or more of a polyadenylation signal, a binding site for proteins that affect an mRNA's stability of location in a cell, or one or more binding sites for miRNAs. In some embodiments, a 3' untranslated region may be between 50 and 500 nucleotides in length or longer.

Exemplary 3' and/or 5' UTR sequences can be derived from mRNA molecules which are stable (e.g., globin, actin, GAPDH, tubulin, histone, or citric acid cycle enzymes) to increase the stability of the sense mRNA molecule. For example, a 5' UTR sequence may include a partial sequence of a CMV immediate-early 1 (IE1) gene, or a fragment thereof to improve the nuclease resistance and/or improve the half-life of the polynucleotide. Also contemplated is the inclusion of a sequence encoding human growth hormone (hGH), or a fragment thereof to the 3' end or untranslated region of the polynucleotide (e.g., mRNA) to further stabilize the polynucleotide. Generally, these modifications improve the stability and/or pharmacokinetic properties (e.g., half-life) of the polynucleotide relative to their unmodified counterparts, and include, for example modifications made to improve such polynucleotides' resistance to in vivo nuclease digestion.

Formation of Liposomes

The liposomal transfer vehicles for use in the compositions of the invention can be prepared by various techniques which are presently known in the art. The liposomes for use in provided compositions can be prepared by various techniques which are presently known in the art. For example, multilamellar vesicles (MLV) may be prepared according to conventional techniques, such as by depositing a selected lipid on the inside wall of a suitable container or vessel by dissolving the lipid in an appropriate solvent, and then evaporating the solvent to leave a thin film on the inside of the vessel or by spray drying. An aqueous phase may then be added to the vessel with a vortexing motion which results in the formation of MLVs. Unilamellar vesicles (ULV) can then be formed by homogenization, sonication or extrusion of the multilamellar vesicles. In addition, unilamellar vesicles can be formed by detergent removal techniques.

In certain embodiments, provided compositions comprise a liposome wherein the mRNA is associated on both the surface of the liposome and encapsulated within the same liposome. For example, during preparation of the compositions of the present invention, cationic liposomes may associate with the mRNA through electrostatic interactions. For example, during preparation of the compositions of the present invention, cationic liposomes may associate with the mRNA through electrostatic interactions.

In some embodiments, the compositions and methods of the invention comprise mRNA encapsulated in a liposome. In some embodiments, the one or more mRNA species may be encapsulated in the same liposome. In some embodiments, the one or more mRNA species may be encapsulated in different liposomes. In some embodiments, the mRNA is encapsulated in one or more liposomes, which differ in their lipid composition, molar ratio of lipid components, size, charge (Zeta potential), targeting ligands and/or combinations thereof. In some embodiments, the one or more liposome may have a different composition of cationic lipids, neutral lipid, PEG-modified lipid and/or combinations thereof. In some embodiments the one or more liposomes may have a different molar ratio of cationic lipid, neutral lipid, cholesterol and PEG-modified lipid used to create the liposome.

The process of incorporation of a desired mRNA into a liposome is often referred to as "loading". Exemplary methods are described in Lasic, et al., FEBS Lett., 312: 255-258, 1992, which is incorporated herein by reference. The liposome-incorporated nucleic acids may be completely or partially located in the interior space of the liposome, within the bilayer membrane of the liposome, or associated with the exterior surface of the liposome membrane. The incorporation of a nucleic acid into liposomes is also referred to herein as "encapsulation" wherein the nucleic acid is entirely contained within the interior space of the liposome. The purpose of incorporating a mRNA into a transfer vehicle, such as a liposome, is often to protect the nucleic acid from an environment which may contain enzymes or chemicals that degrade nucleic acids and/or systems or receptors that cause the rapid excretion of the nucleic acids. Accordingly, in some embodiments, a suitable delivery vehicle is capable of enhancing the stability of the mRNA contained therein and/or facilitate the delivery of mRNA to the target cell or tissue.

Liposome Size

Suitable liposomes in accordance with the present invention may be made in various sizes. In some embodiments, provided liposomes may be made smaller than previously known mRNA encapsulating liposomes. In some embodiments, decreased size of liposomes is associated with more efficient delivery of mRNA. Selection of an appropriate liposome size may take into consideration the site of the target cell or tissue and to some extent the application for which the liposome is being made.

In some embodiments, an appropriate size of liposome is selected to facilitate systemic distribution of antibody encoded by the mRNA. In some embodiments, it may be desirable to limit transfection of the mRNA to certain cells or tissues. For example, to target hepatocytes a liposome may be sized such that its dimensions are smaller than the fenestrations of the endothelial layer lining hepatic sinusoids in the liver; in such cases the liposome could readily penetrate such endothelial fenestrations to reach the target hepatocytes.

Alternatively or additionally, a liposome may be sized such that the dimensions of the liposome are of a sufficient diameter to limit or expressly avoid distribution into certain cells or tissues. For example, a liposome may be sized such that its dimensions are larger than the fenestrations of the endothelial layer lining hepatic sinusoids to thereby limit distribution of the liposomes to hepatocytes.

In some embodiments, the size of a liposome is determined by the length of the largest diameter of the liposome particle. In some embodiments, a suitable liposome has a size no greater than about 250 nm (e.g., no greater than about 225 nm, 200 nm, 175 nm, 150 nm, 125 nm, 100 nm, 75 nm, or 50 nm). In some embodiments, a suitable liposome has a size ranging from about 10-250 nm (e.g., ranging from about 10-225 nm, 10-200 nm, 10-175 nm, 10-150 nm, 10-125 nm, 10-100 nm, 10-75 nm, or 10-50 nm). In some embodiments, a suitable liposome has a size ranging from about 100-250 nm (e.g., ranging from about 100-225 nm, 100-200 nm, 100-175 nm, 100-150 nm). In some embodiments, a suitable liposome has a size ranging from about 10-100 nm (e.g., ranging from about 10-90 nm, 10-80 nm, 10-70 nm, 10-60 nm, or 10-50 nm). In a particular embodiment, a suitable liposome has a size less than about 100 nm.

A variety of alternative methods known in the art are available for sizing of a population of liposomes. One such sizing method is described in U.S. Pat. No. 4,737,323, incorporated herein by reference. Sonicating a liposome suspension either by bath or probe sonication produces a progressive size reduction down to small ULV less than about 0.05 microns in diameter. Homogenization is another method that relies on shearing energy to fragment large liposomes into smaller ones. In a typical homogenization procedure, MLV are recirculated through a standard emulsion homogenizer until selected liposome sizes, typically between about 0.1 and 0.5 microns, are observed. The size of the liposomes may be determined by quasi-electric light scattering (QELS) as described in Bloomfield, Ann. Rev. Biophys. Bioeng., 10:421-150 (1981), incorporated herein by reference. Average liposome diameter may be reduced by sonication of formed liposomes. Intermittent sonication cycles may be alternated with QELS assessment to guide efficient liposome synthesis.

Pharmaceutical Compositions

To facilitate expression of mRNA in vivo, delivery vehicles such as liposomes can be formulated in combination with one or more additional nucleic acids, carriers, targeting ligands or stabilizing reagents, or in pharmacological compositions where it is mixed with suitable excipients. Techniques for formulation and administration of drugs may be found in "Remington's Pharmaceutical Sciences," Mack Publishing Co., Easton, Pa., latest edition.

Provided liposomally-encapsulated or associated mRNAs, and compositions containing the same, may be administered and dosed in accordance with current medical practice, taking into account the clinical condition of the subject, the site and method of administration, the scheduling of administration, the subject's age, sex, body weight and other factors relevant to clinicians of ordinary skill in the art. The "effective amount" for the purposes herein may be determined by such relevant considerations as are known to those of ordinary skill in experimental clinical research, pharmacological, clinical and medical arts. In some embodiments, the amount administered is effective to achieve at least some stabilization, improvement or elimination of symptoms and other indicators as are selected as appropriate measures of disease progress, regression or improvement by those of skill in the art. For example, a suitable amount and dosing regimen is one that causes at least transient protein (e.g., enzyme) production.

Suitable routes of administration include, for example, oral, rectal, vaginal, transmucosal, pulmonary including intratracheal or inhaled, or intestinal administration; parenteral delivery, including intradermal, transdermal (topical), intramuscular, subcutaneous, intramedullary injections, as well as intrathecal, direct intraventricular, intravenous, intraperitoneal, or intranasal. In particular embodiments, the intramuscular administration is to a muscle selected from the group consisting of skeletal muscle, smooth muscle and cardiac muscle. In some embodiments the administration results in delivery of the mRNA to a muscle cell. In some embodiments the administration results in delivery of the mRNA to a hepatocyte (i.e., liver cell). In a particular embodiment, the intramuscular administration results in delivery of the mRNA to a muscle cell.

Alternatively or additionally, liposomally encapsulated mRNAs and compositions of the invention may be administered in a local rather than systemic manner, for example, via injection of the pharmaceutical composition directly into a targeted tissue, preferably in a sustained release formulation. Local delivery can be affected in various ways, depending on the tissue to be targeted. For example, aerosols containing compositions of the present invention can be inhaled (for nasal, tracheal, or bronchial delivery); compositions of the present invention can be injected into the site of injury, disease manifestation, or pain, for example; compositions can be provided in lozenges for oral, tracheal, or esophageal application; can be supplied in liquid, tablet or capsule form for administration to the stomach or intestines, can be supplied in suppository form for rectal or vaginal application; or can even be delivered to the eye by use of creams, drops, or even injection. Formulations containing provided compositions complexed with therapeutic molecules or ligands can even be surgically administered, for example in association with a polymer or other structure or substance that can allow the compositions to diffuse from the site of implantation to surrounding cells. Alternatively, they can be applied surgically without the use of polymers or supports.

Provided methods of the present invention contemplate single as well as multiple administrations of a therapeutically effective amount of the therapeutic agents (e.g., mRNA encoding a GAA protein) described herein. Therapeutic agents can be administered at regular intervals, depending on the nature, severity and extent of the subject's condition (e.g., Pompe disease). In some embodiments, a therapeutically effective amount of the therapeutic agents (e.g., mRNA encoding a GAA protein) of the present invention may be administered intrathecally periodically at regular intervals (e.g., once every year, once every six months, once every five months, once every three months, bimonthly (once every two months), monthly (once every month), biweekly (once every two weeks), twice a month, once every 30 days, once every 28 days, once every 14 days, once every 10 days, once every 7 days, weekly, twice a week, daily or continuously).

In some embodiments, provided liposomes and/or compositions are formulated such that they are suitable for extended-release of the mRNA contained therein. Such extended-release compositions may be conveniently administered to a subject at extended dosing intervals. For example, in one embodiment, the compositions of the present invention are administered to a subject twice a day, daily or every other day. In a preferred embodiment, the compositions of the present invention are administered to a subject twice a week, once a week, once every 7 days, once every 10 days, once every 14 days, once every 28 days, once every 30 days, once every two weeks, once every three weeks, or more preferably once every four weeks, once a month, twice a month, once every six weeks, once every eight weeks, once every other month, once every three months, once every four months, once every six months, once every eight months, once every nine months or annually. Also contemplated are compositions and liposomes which are formulated for depot administration (e.g., intramuscularly, subcutaneously, intravitreally) to either deliver or release a mRNA over extended periods of time. Preferably, the extended-release means employed are combined with modifications made to the mRNA to enhance stability.

As used herein, the term "therapeutically effective amount" is largely determined based on the total amount of the therapeutic agent contained in the pharmaceutical compositions of the present invention. Generally, a therapeutically effective amount is sufficient to achieve a meaningful benefit to the subject (e.g., treating, modulating, curing, preventing and/or ameliorating Pompe disease). For example, a therapeutically effective amount may be an amount sufficient to achieve a desired therapeutic and/or prophylactic effect. Generally, the amount of a therapeutic agent (e.g., mRNA encoding a GAA protein) administered to a subject in need thereof will depend upon the characteristics of the subject. Such characteristics include the condition, disease severity, general health, age, sex and body weight of the subject. One of ordinary skill in the art will be readily able to determine appropriate dosages depending on these and other related factors. In addition, both objective and subjective assays may optionally be employed to identify optimal dosage ranges.

A therapeutically effective amount is commonly administered in a dosing regimen that may comprise multiple unit doses. For any particular therapeutic protein, a therapeutically effective amount (and/or an appropriate unit dose within an effective dosing regimen) may vary, for example, depending on route of administration, on combination with other pharmaceutical agents. Also, the specific therapeutically effective amount (and/or unit dose) for any particular patient may depend upon a variety of factors including the disorder being treated and the severity of the disorder; the activity of the specific pharmaceutical agent employed; the specific composition employed; the age, body weight, general health, sex and diet of the patient; the time of administration, route of administration, and/or rate of excretion or metabolism of the specific protein employed; the duration of the treatment; and like factors as is well known in the medical arts.

In some embodiments, the therapeutically effective dose ranges from about 0.005 mg/kg body weight to 500 mg/kg body weight, e.g., from about 0.005 mg/kg body weight to 400 mg/kg body weight, from about 0.005 mg/kg body weight to 300 mg/kg body weight, from about 0.005 mg/kg body weight to 200 mg/kg body weight, from about 0.005 mg/kg body weight to 100 mg/kg body weight, from about 0.005 mg/kg body weight to 90 mg/kg body weight, from about 0.005 mg/kg body weight to 80 mg/kg body weight, from about 0.005 mg/kg body weight to 70 mg/kg body weight, from about 0.005 mg/kg body weight to 60 mg/kg body weight, from about 0.005 mg/kg body weight to 50 mg/kg body weight, from about 0.005 mg/kg body weight to 40 mg/kg body weight, from about 0.005 mg/kg body weight to 30 mg/kg body weight, from about 0.005 mg/kg body weight to 25 mg/kg body weight, from about 0.005 mg/kg body weight to 20 mg/kg body weight, from about 0.005 mg/kg body weight to 15 mg/kg body weight, from about 0.005 mg/kg body weight to 10 mg/kg body weight.

In some embodiments, the therapeutically effective dose is greater than about 0.1 mg/kg body weight, greater than about 0.5 mg/kg body weight, greater than about 1.0 mg/kg body weight, greater than about 3 mg/kg body weight, greater than about 5 mg/kg body weight, greater than about 10 mg/kg body weight, greater than about 15 mg/kg body weight, greater than about 20 mg/kg body weight, greater than about 30 mg/kg body weight, greater than about 40 mg/kg body weight, greater than about 50 mg/kg body weight, greater than about 60 mg/kg body weight, greater than about 70 mg/kg body weight, greater than about 80 mg/kg body weight, greater than about 90 mg/kg body weight, greater than about 100 mg/kg body weight, greater than about 150 mg/kg body weight, greater than about 200 mg/kg body weight, greater than about 250 mg/kg body weight, greater than about 300 mg/kg body weight, greater than about 350 mg/kg body weight, greater than about 400 mg/kg body weight, greater than about 450 mg/kg body weight, greater than about 500 mg/kg body weight. In a particular embodiment, the therapeutically effective dose is 1.0 mg/kg. In some embodiments, the therapeutically effective dose of 1.0 mg/kg is administered intramuscularly or intravenously.

Also contemplated herein are lyophilized pharmaceutical compositions comprising one or more of the liposomes disclosed herein and related methods for the use of such compositions as disclosed for example, in U.S. Provisional Application No. 61/494,882, filed Jun. 8, 2011, the teachings of which are incorporated herein by reference in their entirety. For example, lyophilized pharmaceutical compositions according to the invention may be reconstituted prior to administration or can be reconstituted in vivo. For example, a lyophilized pharmaceutical composition can be formulated in an appropriate dosage form (e.g., an intradermal dosage form such as a disk, rod or membrane) and administered such that the dosage form is rehydrated over time in vivo by the individual's bodily fluids.

Provided liposomes and compositions may be administered to any desired tissue. In some embodiments, the GAA mRNA delivered by provided liposomes or compositions is expressed in the tissue in which the liposomes and/or compositions were administered. In some embodiments, the mRNA delivered is expressed in a tissue different from the tissue in which the liposomes and/or compositions were administered. Exemplary tissues in which delivered mRNA may be delivered and/or expressed include, but are not limited to the liver, kidney, heart, spleen, serum, brain, skeletal muscle, lymph nodes, skin, and/or cerebrospinal fluid.

In some embodiments, administering the provided composition results in an increased GAA mRNA expression level in a biological sample from a subject as compared to a baseline expression level before treatment. Typically, the baseline level is measured immediately before treatment. Biological samples include, for example, whole blood, serum, plasma, urine and tissue samples (e.g., muscle, liver, skin fibroblasts). In some embodiments, administering the provided composition results in an increased GAA mRNA expression level by at least about 10%, 20%, 30%, 40%, 50%, 60%, 70%, 80%, 90%, or 95% as compared to the baseline level immediately before treatment. In some embodiments, administering the provided composition results in an increased GAA mRNA expression level as compared to a GAA mRNA expression level in subjects who are not treated According to the present invention, a therapeutically effective dose of the provided composition, when administered regularly, results in an increased hepatic GAA protein level in a subject as compared to a baseline hepatic GAA protein level before treatment. In some embodiments, a therapeutically effective dose of the provided composition, when administered regularly, results in an increased muscle GAA protein level in a subject as compared to a baseline muscle GAA protein level before treatment. In some embodiments, the muscle is skeletal muscle (e.g., striated muscle, voluntary muscle), smooth muscle (e.g., visceral muscle, involuntary muscle) or cardiac muscle. In some embodiments, a therapeutically effective dose of the provided composition, when administered regularly, results in a reduced serum creatine kinase level in a subject as compared to a baseline creatine kinase level before treatment. In some embodiments, a therapeutically effective dose of the provided composition, when administered regularly, results in a reduced urinary glucose tetrasaccharide, (Glcα1-6Glcα1-4Glcα1-4Glc or $Glc_4$) level in a subject as compared to a baseline $Glc_4$ level before treatment. In some embodiments, a therapeutically effective dose of the provided composition, when administered regularly, results in a reduced serum aspartate transaminase (e.g., AST, aspartate aminotransferase, serum, glutamic oxaloacetic transaminase) level in as subject as compared to a baseline AST level before treatment. In some embodiments, a therapeutically effective dose of the provided composition, when administered regularly, results in a reduced serum alanine transaminase (e.g., ALT, alanine aminotransferase, serum glutamic-pyruvic transaminase) level in a subject as compared to a baseline ALT level before treatment. In some embodiments, a therapeutically effective dose of the provided composition, when administered regularly, results in a reduced serum lactate dehydrogenase (e.g., LDH, lactic dehydrogenase) level in a subject as compared to a baseline LDH level before treatment. In some embodiments, a therapeutically effective dose of the provided composition, when administered regularly, results in an increased GAA enzyme activity level in a biological sample from a subject as compared to a baseline GAA enzyme activity level before treatment.

In some embodiments, administering the provided composition results in an increased GAA protein level in the liver of a subject as compared to a baseline level before treatment. Typically, the baseline level is measured immediately before treatment. In some embodiments, administering the provided composition results in an increased GAA protein level in the liver by at least about 10%, 20%, 30%, 40%, 50%, 60%, 70%, 80%, 90%, or 95% as compared to a baseline level before treatment. In some embodiments, administering the provided composition results in an increased GAA protein level in the liver as compared to a GAA protein level in the liver of subjects who are not treated.

In some embodiments, administering the provided composition results in an increased GAA protein level in skeletal muscle of a subject as compared to a baseline level before treatment. Typically, the baseline level is measured immediately before treatment. In some embodiments, administering the provided composition results in an increased GAA protein level in skeletal muscle by at least about 10%, 20%, 30%, 40%, 50%, 60%, 70%, 80%, 90%, or 95% as compared to a baseline level before treatment. In some embodiments, administering the provided composition results in an increased GAA protein level in skeletal muscle as compared to the GAA protein level in skeletal muscle of subjects who are not treated.

In some embodiments, administering the provided composition results in an increased GAA protein level in cardiac muscle of a subject as compared to a baseline level before treatment. Typically, the baseline level is measured immediately before treatment. In some embodiments, administering the provided composition results in an increased GAA protein level in cardiac muscle by at least about 10%, 20%, 30%, 40%, 50%, 60%, 70%, 80%, 90%, or 95% as compared to a baseline level before treatment. In some embodiments, administering the provided composition results in an increased GAA protein level in cardiac muscle as compared to a GAA protein level in cardiac muscle of subjects who are not treated.

In some embodiments, administering the provided composition results in an increased level of GAA protein in smooth muscle of a subject as compared to a baseline level before treatment. Typically, the baseline level is measured immediately before treatment. In some embodiments, administering the provided composition results in an increased GAA protein level in smooth muscle by at least about 10%, 20%, 30%, 40%, 50%, 60%, 70%, 80%, 90%, or 95% as compared to a baseline level before treatment. In some embodiments, administering the provided composition results in an increased GAA protein level in smooth muscle as compared to a GAA protein level in smooth muscle of subjects who are not treated.

In some embodiments, administering the provided composition results in an increased level of GAA protein in a muscle cell of a subject as compared to a baseline level before treatment. Typically, the baseline level is measured immediately before treatment. In some embodiments the muscle cell is a myocyte, a myotube, a myoblast, a cardiomyocyte or a cardiomyoblast. In some embodiments, administering the provided composition results in an increased GAA protein level in the muscle cell by at least about 10%, 20%, 30%, 40%, 50%, 60%, 70%, 80%, 90%, or 95% as compared to a baseline level before treatment. In some embodiments, administering the provided composition results in an increased GAA protein level in a muscle cell as compared to the GAA protein level a muscle cell of subjects who are not treated.

In some embodiments, administering the provided composition results in an increased level of GAA protein in a liver cell (e.g., a hepatocyte) of a subject as compared to a baseline level before treatment. Typically, the baseline level is measured immediately before treatment. In some embodiments, administering the provided composition results in an increased GAA protein level in the liver cell by at least about 10%, 20%, 30%, 40%, 50%, 60%, 70%, 80%, 90%, or 95% as compared to a baseline level before treatment. In some embodiments, administering the provided composition results in an increased GAA protein level in a liver cell as compared to the GAA protein level a liver cell of subjects who are not treated.

In some embodiments, administering the provided composition results in an increased GAA protein level in plasma or serum of subject as compared to a baseline level before treatment. Typically, the baseline level is measured immediately before treatment. In some embodiments, administering the provided composition results in an increased GAA protein level in plasma or serum by at least about 10%, 20%, 30%, 40%, 50%, 60%, 70%, 80%, 90%, or 95% as compared to a baseline level before treatment. In some embodiments, administering the provided composition results in an increased GAA protein level in plasma or serum as compared to a GAA protein level in plasma or serum of subjects who are not treated.

In some embodiments, administering the provided composition results in reduced a serum creatine kinase level in a subject as compared to a baseline level before treatment. Typically, the baseline level is measured immediately before treatment. In some embodiments, administering the provided composition results in a reduced serum creatine kinase level by at least about 10%, 20%, 30%, 40%, 50%, 60%, 70%, 80%, 90%, or 95% as compared to a baseline serum creatine kinase level immediately before treatment. In some embodiments, administering of the provided composition results in a reduced serum creatine kinase level to less than about 2000 IU/L, 1500 IU/L, 1000 IU/L, 750 IU/L, 500 IU/L, 250 IU/L, 100 IU/L, 90 IU/L, 80 IU/L, 70 IU/L or 60 IU/L. In some embodiments, administering the provided composition results in a reduced serum creatine kinase level as compared to a serum creatine kinase level in subjects who are not treated.

In some embodiments, administering the provided composition results in a reduced urinary $Glc_4$ level in a subject as compared to a baseline level before treatment. Typically, the baseline level is measured immediately before treatment. In some embodiments, administering the provided composition results in a reduced urinary $Glc_4$ level by at least about 10%, 20%, 30%, 40%, 50%, 60%, 70%, 80%, 90%, or 95% as compared to a baseline level immediately before treatment. In some embodiments, administering the provided composition results in a reduced urinary $Glc_4$ level to less than about 100 mmol $Glc_4$/mol creatinine, 90 mmol $Glc_4$/mol creatinine, 80 mmol $Glc_4$/mol creatinine, 70 mmol $Glc_4$/mol creatinine, 60 mmol $Glc_4$/mol creatinine, 50 mmol $Glc_4$/mol creatinine, 40 mmol $Glc_4$/mol creatinine, 30 mmol $Glc_4$/mol creatinine or 20 mmol $Glc_4$/mol creatinine. In some embodiments, administering the provided composition results in a reduced urinary $Glc_4$ level as compared to a urinary $Glc_4$ level in subjects who are not treated.

In some embodiments, administering the provided composition results in a reduced muscle glycogen level in a subject as compared to a baseline level before treatment. Typically, a baseline level is measured immediately before treatment. In some embodiments, administering the provided composition results in a reduced muscle glycogen level by at least about 10%, 20%, 30%, 40%, 50%, 60%, 70%, 80%, 90%, or 95% as compared to a baseline level immediately before treatment. In some embodiments, administering the provided composition results in a reduced muscle glycogen level as compared to a muscle glycogen level in subjects who are not treated. In particular embodiments, the muscle is skeletal muscle, smooth muscle or cardiac muscle.

In some embodiments, administering the provided composition results in a reduced liver glycogen level in a subject as compared to a baseline level before treatment. Typically, the baseline level is measured immediately before treatment. In some embodiments, administering the provided composition results in a reduced liver glycogen level by at least about 10%, 20%, 30%, 40%, 50%, 60%, 70%, 80%, 90%, or 95% as compared to a baseline level immediately before treatment. In some embodiments, administering the provided composition results in a reduced liver glycogen level as compared to a liver glycogen level in subjects who are not treated.

In some embodiments, administering the provided composition results in a reduced serum aspartate transaminase (AST) level in a subject as compared to a baseline level before treatment. Typically, the baseline level is measured immediately before treatment. In some embodiments, administering the provided composition results in a reduced serum AST level by at least about 10%, 20%, 30%, 40%, 50%, 60%, 70%, 80%, 90%, or 95% as compared to a baseline level immediately before treatment. In some embodiments, administering the provided composition results in a reduced serum AST level to less than about 600 IU/L, 500 IU/L, 400 IU/L, 300 IU/L, 200 IU/L, 100 IU/L, 50 IU/L, 25 IU/L, 20 IU/L or 10 IU/L. In some embodiments, administering the provided composition results in a reduced serum AST level as compared to a serum AST level in subjects who are not treated.

In some embodiments, administering the provided composition results in a reduced serum alanine transaminase (ALT) level in a subject as compared to a baseline level before treatment. Typically, the baseline level is measured immediately before treatment. In some embodiments, administering the provided composition results in a reduced serum ALT level by at least about 10%, 20%, 30%, 40%, 50%, 60%, 70%, 80%, 90%, or 95% as compared to a baseline level immediately before treatment. In some embodiments, administering the provided composition results in a reduced serum ALT level to less than about 1000 IU/L, 900 IU/L, 800 IU/L, 700 IU/L, 600 IU/L, 500 IU/L, 400 IU/L, 300 IU/L, 200 IU/L, 100 IU/L, 50 IU/L, 25 IU/L, 20 IU/L or 10 IU/L. In some embodiments, administering the provided composition results in a reduced serum ALT level as compared to a serum ALT level in subjects who are not treated.

In some embodiments, administering the provided composition results in a reduced serum lactate dehydrogenase (LDH) level in a subject as compared to a baseline level before treatment. Typically, the baseline level is measured immediately before treatment. In some embodiments, administering the provided composition results in a reduced serum lactate dehydrogenase LDH level by at least about 10%, 20%, 30%, 40%, 50%, 60%, 70%, 80%, 90%, or 95% as compared to a baseline level immediately before treatment. In some embodiments, administering the provided composition results in a reduced serum LDH level to less than about 2000 IU/L, 1500 IU/L, 1000 IU/L, 900 IU/L, 800 IU/L, 700 IU/L, 600 IU/L, 500 IU/L, 400 IU/L, 300 IU/L, 200 IU/L or 100 IU/L. In some embodiments, administering the provided composition results in a reduced serum LDH level as compared to a serum LDH level in subjects who are not treated.

In some embodiments, administering the provided composition results in increased GAA enzyme activity in a biological sample from a subject as compared to the baseline level before treatment. Typically, the baseline level is measured immediately before treatment. Biological samples include, for example, whole blood, serum, plasma, urine and tissue samples (e.g., muscle, liver, skin fibroblasts). In some embodiments, administering the provided composition results in an increased GAA enzyme activity by at least about 10%, 20%, 30%, 40%, 50%, 60%, 70%, 80%, 90%, or 95% as compared to a baseline level immediately before treatment. In some embodiments, administering the provided composition results in an increased GAA enzyme activity as compared to GAA enzyme activity in subjects who are not treated.

According to various embodiments, the timing of expression of delivered mRNAs can be tuned to suit a particular medical need. In some embodiments, the expression of the protein encoded by delivered mRNA is detectable 1, 2, 3, 6, 12, 24, 48, 72, and/or 96 hours after administration of provided liposomes and/or compositions. In some embodiments, the expression of the protein encoded by delivered mRNA is detectable 1 week, two weeks, and/or 1 month after administration.

EXAMPLES

While certain compounds, compositions and methods of the present invention have been described with specificity in accordance with certain embodiments, the following examples serve only to illustrate the compounds of the invention and are not intended to limit the same.

Example 1. Exemplary Liposome Formulations for GAA mRNA Delivery and Expression This example provides exemplary liposome formulations for effective delivery and expression of GAA mRNA in vivo.

Lipid Materials

The formulations described herein include a multi-component lipid mixture of varying ratios employing one or more cationic lipids, helper lipids (e.g., non-cationic lipids and/or cholesterol-based lipids) and PEGylated lipids designed to encapsulate mRNA encoding GAA protein. Cationic lipids can include (but not exclusively) DOTAP (1,2-dioleyl trimethylammonium propane), DODAP (1,2-dioleyl-3-dimethylammonium propane), DOTMA (1,2-di-O-octadecenyl-3-trimethylammonium propane), DLinDMA (Heyes, J.; Palmer, L.; Bremner, K.; MacLachlan, I. "Cationic lipid saturation influences intracellular delivery of encapsulated nucleic acids" *J. Contr. Rel.* 2005, 107, 276-287), DLin-KC2-DMA (Semple, S.C. et al. "Rational Design of Cationic Lipids for siRNA Delivery" *Nature Biotech.* 2010, 28, 172-176), C12-200 (Love, K. T. et al. "Lipid-like materials for low-dose in vivo gene silencing" *PNAS* 2010, 107, 1864-1869), cKK-E12 (3,6-bis(4-(bis(2-hydroxydodecyl)amino)butyl)piperazine-2,5-dione), HGT5000, HGT5001, HGT4003, ICE, dialkylamino-based, imidazole-based, guanidinium-based, etc. Helper lipids can include (but not exclusively) DSPC (1,2-distearoyl-sn-glycero-3-phosphocholine), DPPC (1,2-dipalmitoyl-sn-glycero-3-phosphocholine), DOPE (1,2-dioleyl-sn-glycero-3-phosphoethanolamine), DOPC (1,2-dioleyl-sn-glycero-3-phosphotidylcholine) DPPE (1,2-dipalmitoyl-sn-glycero-3-phosphoethanolamine), DMPE (1,2-dimyristoyl-sn-glycero-3-phosphoethanolamine), DOPG (,2-dioleoyl-sn-glycero-3-phospho-(1'-rac-glycerol)), cholesterol, etc. The PEGylated lipids can include (but not exclusively) a poly(ethylene) glycol chain of up to 5 kDa in length covalently attached to a lipid with alkyl chain(s) of $C_6$-$C_{20}$ length.

Codon-optimized human acid alpha-glucosidase (GAA) messenger RNA was synthesized by in vitro transcription from a plasmid DNA template encoding the gene, which was followed by the addition of a 5' cap structure (Cap 1) (Fechter, P.; Brownlee, G. G. "Recognition of mRNA cap structures by viral and cellular proteins" J. Gen. Virology 2005, 86, 1239-1249) and a 3' poly(A) tail of approximately 250 nucleotides in length (SEQ ID NO: 7) as determined by gel electrophoresis. 5' and 3' untranslated regions present in each mRNA product are represented as X and Y, respectively and defined as stated (vide infra).

Exemplary Codon-Optimized Human Acid Alpha-Glucosidase (GAA) mRNAs

```
Construct design:
X-SEQ ID NO: 3-Y.

5' and 3' UTR Sequences
X (5' UTR Sequence)=
                                  [SEQ ID NO: 8]
GGACAGAUCGCCUGGAGACGCCAUCCACGCUGUUUUGACCUCCAUAGAA

GACACCGGGACCGAUCCAGCCUCCGCGGCCGGGAACGGUGCAUUGGAAC

GCGGAUUCCCCGUGCCAAGAGUGACUCACCGUCCUUGACACG

Y (3' UTR Sequence)=
                                  [SEQ ID NO: 9]
CGGGUGGCAUCCCUGUGACCCCUCCCCAGUGCCUCUCCUGGCCCUGGAA

GUUGCCACUCCAGUGCCCACCAGCCUUGUCCUAAUAAAAUUAAGUUGCA

UCAAGCU
OR
                                  [SEQ ID NO: 10]
GGGUGGCAUCCCUGUGACCCCUCCCCAGUGCCUCUCCUGGCCCUGGAAG

UUGCCACUCCAGUGCCCACCAGCCUUGUCCUAAUAAAAUUAAGUUGCAU

CAAAGCU
```

An exemplary codon-optimized human GAA mRNA sequence includes SEQ ID NO: 3 described in the detailed description section.

An exemplary full-length codon-optimized human acid alpha-glucosidase (GAA) messenger RNA sequence is shown below:

```
                                  [SEQ ID NO: 11]
GGACAGAUCGCCUGGAGACGCCAUCCACGCUGUUUUGACCUCCAUAGAA

GACACCGGGACCGAUCCAGCCUCCGCGGCCGGGAACGGUGCAUUGGAAC

GCGGAUUCCCCGUGCCAAGAGUGACUCACCGUCCUUGACACGAUGGGAG

UCAGACACCCGCCGUGCUCGCACAGGCUUCUGGCCGUGUGCGCACUCGU

GAGUCUGGCGACUGCUGCGUUGCUGGGGCACAUUCUUCUCCACGACUUU

CUCUUGGUGCCCCGAGAAUUGUCGGGCUCGUCGCCGGUACUGGAAGAAA

CCCACCCCGCACAUCAGCAGGGCGCGUCGCGGCCUGGUCCGAGGGAUGC

CCAGGCACAUCCCGGAAGGCCACGAGCCGUCCCGACUCAAUGUGACGUA

CCUCCCAAUUCCCGGUUCGACUGUGCGCCAGACAAGGCAAUCACGCAAG

AGCAGUGCGAAGCCCGUGGAUGCUGCUAUAUUCCGGCGAAGCAGGGACU

UCAGGGAGCCCAGAUGGGGCAGCCCUGGUGUUUCUUCCCGCCUUCCUAU

CCCUCAUAUAAGCUGGAGAAUUUGUCGUCCUCGGAAAUGGGGUAUACCG

CUACUCUUACGAGAACCACCCCCACAUUCUUUCCGAAGGACAUCCUUAC

UCUGCGGCUCGACGUGAUGAUGGAGACAGAAAAUAGGCUGCAUUUCACG

AUCAAAGACCCGGCGAACCGGAGAUAUGAGGUUCCGCUUGAGACUCCCC

ACGUUCACUCUCGUGCGCCUUCACCCUUGUACUCCGUGGAGUUCUCGGA

AGAACCGUUCGGGGUGAUCGUCAGACGUCAACUUGAUGGUAGGGUAUUG

CUGAACACAACGGUCGCCCCCUUGUUUUUCGCCGACCAGUUUCUGCAGC
```

-continued

```
UUUCGACAUCGCUGCCGUCCCAGUAUAUCACAGGGCUCGCGGAGCAUCU
UUCACCCCUCAUGCUGAGCACGAGCUGGACACGGAUUACGCUCUGGAAC
AGGGAUCUCGCGCCGACGCCCGGAGCGAAUUUGUAUGGGUCGCAUCCCU
UCUACCUCGCAUUGGAAGACGGGGGUUCCGCGCACGGAGUAUUCCUGCU
UAAUUCUAAUGCGAUGGACGUUGUCUUGCAGCCCUCCCCUGCUUUGUCG
UGGCGUUCCACGGGGGGCAUUUUGGACGUUUACAUCUUUUUGGGACCCG
AGCCAAAGAGCGUAGUGCAGCAGUAUUUGGAUGUAGUGGGCUACCCCUU
CAUGCCGCCUUAUUGGGGACUGGGGUUCCAUCUCUGCCGCUGGGGGUAC
UCUUCGACCGCGAUCACCCGCCAGGUGGUCGAGAACAUGACCAGAGCAC
AUUUCCCUUUGGACGUGCAGUGGAAUGAUUUGGAUUACAUGGAUAGCCG
AAGAGACUUCACGUUCAAUAAGGACGGGUUUAGAGAUUUUCCCGCGAUG
GUGCAAGAAUUGCACCAGGGUGGGCGCAGAUACAUGAUGAUCGUCGAUC
CCGCCAUCAGCAGCUCGGGACCAGCGGGGAGUUACCGGCCUUACGAUGA
GGGACUUAGGAGAGGCGUCUUUAUCACGAACGAAACAGGUCAGCCGCUC
AUUGGUAAAGUGUGGCCUGGAUCAACGGCCUUUCCCGACUUCACGAAUC
CCACAGCCCUCGCCUGGUGGGAAGACAUGGUGGCGGAGUUUCACGACCA
AGUACCGUUGAUGGGAUGUGGAUUGAUAUGAACGAACCCUCAAACUUU
AUUCGCGGCUCGGAAGAUGGAUGCCCGAAUAAUGAGCUUGAGAAUCCCC
CGUAUGUGCCAGGGGUGGUAGGUGGGACGCUCCAGGCCGCUACGAUCUG
UGCGUCAUCACAUCAGUUCUUGUCAACGCACUACAACUUGCACAAUCUU
UACGGUUUGACUGAAGCCAUCGCUUCGCAUCGCGCGCUGGUCAAAGCGC
GUGGUACGCGACCCUUCGUUAUUUCUCGGUCCACAUUUGCCGGGCACGG
UCGGUAUGCCGACACUGGACGGGAGAUGUCUGGUCUAGCUGGGAGCAG
CUCGCGUCGAGCGUACCGGAGAUCCUCCAGUUCAAUCUUUUGGGAGUUC
CGCUCGUCGGCGCUGACGUGUGCGGUUUUCUCGGAAACACAUCAGAAGA
GCUUUGCGUACGCUGGACACAGCUCGGUGCGUUUUACCCCUUUAUGAGA
AACCAUAACUCGUUGCUCUCACUCCCUCAAGAGCCGUACAGUUUUUCGG
AGCCUGCGCAACAGGCGAUGCGGAAGGCAUUGACACUUCGCUAUGCACU
GCUCCCGCAUCUCUAUACUCUGUUCCAUCAGGCCCAUGUGGCUGGAGAA
ACGGUGGCGAGGCCCCUGUUCUUGGAGUUCCCCAAAGAUAGUUCCACAU
GGACCGUGGAUCACCAGUUGCUGUGGGAGAGGCGCUUCUGAUCACUCC
GGUACUUCAGGCGGGUAAAGCGGAAGUCACUGGGUAUUUCCCGCUUGGG
ACCUGGUACGACCUUCAGACUGUCCCAGUAGAAGCCCUCGGAAGCCUGC
CACCUCCCCUGCUGCACCCCGCGAGCCUGCAAUCCAUAGCGAGGGCCA
GUGGGUAACGUUGCCAGCCCCACUGGAUACCAUCAAUGUCCACCUCAGG
GCGGGUUACAUUAUCCCUCUCCAAGGCCCUGGGUUGACCACCACAGAGU
CGCGCCAGCAGCCAAUGGCACUUGCGGUCGCAUUGACGAAAGGGGUGA
AGCCCGAGGGGAACUGUUUGGAUGACGGGGAAAGCCUUGAGGUGCUG
GAACGGGGAGCGUACACACAAGUCAUUUUCUUGGCCAGGAACAACACUA
UUGUCAACGAGUUGGUGCGCGUGACCUCGAGGGUGCCGGACUGCAACU
GCAGAAGGUCACGGUCCUCGGAGUGGCGACAGCACCCCAACAGGUCCUU
```

-continued

```
AGUAACGGAGUACCUGUCUCGAACUUUACAUACUCCCCGGACACGAAGG
UGCUCGACAUCUGUGUGUCGCUGCUUAUGGGGGAACAGUUUCUCGUGAG
CUGGUGCUAGCGGGUGGCAUCCCUGUGACCCCUCCCCAGUGCCUCUCCU
GGCCCUGGAAGUUGCCACUCCAGUGCCCACCAGCCUUGUCCUAAUAAAA
UUAAGUUGCAUCAAGCU.
```

In another example, a full length codon-optimized human acid alpha-glucosidase (GAA) messenger RNA sequence is shown below:

[SEQ ID NO: 12]
```
GGACAGAUCGCCUGGAGACGCCAUCCACGCUGUUUUGACCUCCAUAGAA
GACACCGGGACCGAUCCAGCCUCCGCGGCCGGGAACGGUGCAUUGGAAC
GCGGAUUCCCCGUGCCAAGAGUGACUCACCGUCCUUGACACGAUGGGAG
UCAGACACCCGCCGUGCUCGCACAGGCUUCUGGCCGUGUGCGCACUCGU
GAGUCUGGCGACUGCUGCGUUGCUGGGGCACAUUCUUCUCCACGACUUU
CUCUUGGUGCCCCGAGAAUUGUCGGGCUCGUCGCCGGUACUGGAAGAAA
CCCACCCCGCACAUCAGCAGGGCGCGUCGCGGCCUGGUCCGAGGGAUGC
CCAGGCACAUCCCGGAAGGCCACGAGCCGUCCCGACUCAAUGUGACGUA
CCUCCCAAUUCCCGGUUCGACUGUGCGCCAGACAAGGCAAUCACGCAAG
AGCAGUGCGAAGCCCGUGGAUGCUGCUAUAUUCCGGCGAAGCAGGGACU
UCAGGGAGCCCAGAUGGGGCAGCCCUGGUGUUUCUUCCCGCCUUCCUAU
CCCUCAUAUAAGCUGGAGAAUUUGUCGUCCUCGAAAUGGGGUAUACCG
CUACUCUUACGAGAACCACCCCCACAUUCUUUCCGAAGGACAUCCUUAC
UCUGCGGCUCGACGUGAUGAUGGAGACAGAAAAUAGGCUGCAUUUCACG
AUCAAAGACCCGGCGAACCGGAGAUAUGAGGUUCCGCUUGAGACUCCCC
ACGUUCACUCUCGUGCGCCUUCACCCUUGUACUCCGUGGAGUUCUCGGA
AGAACCGUUCGGGGUGAUCGUCAGACGUCAACUUGAUGGUAGGGUAUUG
CUGAACACAACGGUCGCCCCCUUGUUUUUCGCCGACCAGUUUCUGCAGC
UUUCGACAUCGCUGCCGUCCCAGUAUAUCACAGGGCUCGCGGAGCAUCU
UUCACCCCUCAUGCUGAGCACGAGCUGGACACGGAUUACGCUCUGGAAC
AGGGAUCUCGCGCCGACGCCCGGAGCGAAUUUGUAUGGGUCGCAUCCCU
UCUACCUCGCAUUGGAAGACGGGGGUUCCGCGCACGGAGUAUUCCUGCU
UAAUUCUAAUGCGAUGGACGUUGUCUUGCAGCCCUCCCCUGCUUUGUCG
UGGCGUUCCACGGGGGGCAUUUUGGACGUUUACAUCUUUUUGGGACCCG
AGCCAAAGAGCGUAGUGCAGCAGUAUUUGGAUGUAGUGGGCUACCCCUU
CAUGCCGCCUUAUUGGGGACUGGGGUUCCAUCUCUGCCGCUGGGGGUAC
UCUUCGACCGCGAUCACCCGCCAGGUGGUCGAGAACAUGACCAGAGCAC
AUUUCCCUUUGGACGUGCAGUGGAAUGAUUUGGAUUACAUGGAUAGCCG
AAGAGACUUCACGUUCAAUAAGGACGGGUUUAGAGAUUUUCCCGCGAUG
GUGCAAGAAUUGCACCAGGGUGGGCGCAGAUACAUGAUGAUCGUCGAUC
CCGCCAUCAGCAGCUCGGGACCAGCGGGGAGUUACCGGCCUUACGAUGA
GGGACUUAGGAGAGGCGUCUUUAUCACGAACGAAACAGGUCAGCCGCUC
```

-continued

```
AUUGGUAAAGUGUGGCCUGGAUCAACGGCCUUUCCCGACUUCACGAAUC

CCACAGCCCUCGCCUGGUGGGAAGACAUGGUGGCGGAGUUUCACGACCA

AGUACCGUUUGAUGGGAUGUGGAUUGAUAUGAACGAACCCUCAAACUUU

AUUCGCGGCUCGGAAGAUGGAUGCCCGAAUAAUGAGCUUGAGAAUCCCC

CGUAUGUGCCAGGGGUGGUAGGUGGGACGCUCCAGGCCGCUACGAUCUG

UGCGUCAUCACAUCAGUUCUUGUCAACGCACUACAACUUGCACAAUCUU

UACGGUUUGACUGAAGCCAUCGCUUCGCAUCGCGCGCUGGUCAAAGCGC

GUGGUACGCGACCCUUCGUUAUUUCUCGGUCCACAUUUGCCGGGCACGG

UCGGUAUGCCGGACACUGGACGGGAGAUGUCUGGUCUAGCUGGGAGCAG

CUCGCGUCGAGCGUACCGGAGAUCCUCCAGUUCAAUCUUUUGGGAGUUC

CGCUCGUCGGCGCUGACGUGUGCGGUUUUCUCGGAAACACAUCAGAAGA

GCUUUGCGUACGCUGGACACAGCUCGGUGCGUUUUACCCCUUUAUGAGA

AACCAUAACUCGUUGCUCUCACUCCCUCAAGAGCCGUACAGUUUUUCGG

AGCCUGCGCAACAGGCGAUGCGGAAGGCAUUGACACUUCGCUAUGCACU

GCUCCCGCAUCUCUAUACUCUGUUCCAUCAGGCCCAUGUGGCUGGAGAA

ACGGUGGCGAGGCCCCUGUUCUUGGAGUUCCCCAAAGAUAGUUCCACAU

GGACCGUGGAUCACCAGUUGCUGUGGGGAGAGGCGCUUCUGAUCACUCC

GGUACUUCAGGCGGGUAAAGCGGAAGUCACUGGGUAUUUCCCGCUUGGG

ACCUGGUACGACCUUCAGACUGUCCCAGUAGAAGCCCUCGGAAGCCUGC

CACCUCCCCUGCUGCACCCCGCGAGCCUGCAAUCCAUAGCGAGGGCCA

GUGGGUAACGUUGCCAGCCCCACUGGAUACCAUCAAUGUCCACCUCAGG

GCGGGUUACAUUAUCCCUCUCCAAGGCCCUGGGUUGACCACCACAGAGU

CGCGCCAGCAGCCAAUGGCACUUGCGGUCGCAUUGACGAAAGGGGGUGA

AGCCCGAGGGGAACUGUUUUGGGAUGACGGGGAAAGCCUUGAGGUGCUG

GAACGGGGAGCGUACACACAAGUCAUUUCUUGGCCAGGAACAACACUA

UUGUCAACGAGUUGGUGCGCGUGACCUCUGAGGGUGCCGGACUGCAACU

GCAGAAGGUCACGGUCCUCGGAGUGGCGACAGCACCCCAACAGGUCCUU

AGUAACGGAGUACCUGUCUCGAACUUUACAUACUCCCCGGACACGAAGG

UGCUCGACAUCUGUGUGUCGCUGCUUAUGGGGGAACAGUUUCUCGUGAG

CUGGUGCUAGGGGUGGCAUCCCUGUGACCCCUCCCCAGUGCCUCUCCUG

GCCCUGGAAGUUGCCACUCCAGUGCCCACCAGCCUUGUCCUAAUAAAAU

UAAGUUGCAUCAAAGCU.
```

Exemplary Formulation Protocols

A. cKK-E12

Aliquots of 50 mg/mL ethanolic solutions of cKK-E12, DOPE, cholesterol and DMG-PEG2K were mixed and diluted with ethanol to 3 mL final volume. Separately, an aqueous buffered solution (10 mM citrate/150 mM NaCl, pH 4.5) of GAA mRNA was prepared from a 1 mg/mL stock. The lipid solution was injected rapidly into the aqueous mRNA solution and shaken to yield a final suspension in 20% ethanol. The resulting nanoparticle suspension was filtered, diafiltrated with 1×PBS (pH 7.4), concentrated and stored at 2-8° C. Final concentration=0.64 mg/mL GAA mRNA (encapsulated). $Z_{ave}$=80 nm; PDI=0.17. % Encapsulation=85%; Yield=89%.

B. C12-200

Aliquots of 50 mg/mL ethanolic solutions of C12-200, DOPE, cholesterol and DMG-PEG2K are mixed and diluted with ethanol to 3 mL final volume. Separately, an aqueous buffered solution (10 mM citrate/150 mM NaCl, pH 4.5) of GAA mRNA is prepared from a 1 mg/mL stock. The lipid solution is injected rapidly into the aqueous mRNA solution and shaken to yield a final suspension in 20% ethanol. The resulting nanoparticle suspension is filtered, diafiltrated with 1×PBS (pH 7.4), concentrated and stored at 2-8° C. The final concentration, $Z_{ave}$, $Dv_{(50)}$ and $Dv_{(90)}$ of the GAA encapsulated mRNA are determined.

C. HGT4003

Aliquots of 50 mg/mL ethanolic solutions of HGT4003, DOPE, cholesterol and DMG-PEG2K are mixed and diluted with ethanol to 3 mL final volume. Separately, an aqueous buffered solution (10 mM citrate/150 mM NaCl, pH 4.5) of GAA mRNA is prepared from a 1 mg/mL stock. The lipid solution is injected rapidly into the aqueous mRNA solution and shaken to yield a final suspension in 20% ethanol. The resulting nanoparticle suspension is filtered, diafiltrated with 1×PBS (pH 7.4), concentrated and stored at 2-8° C. The final concentration, $Z_{ave}$, $Dv_{(50)}$ and $Dv_{(90)}$ of the GAA encapsulated mRNA are determined.

D. ICE

Aliquots of 50 mg/mL ethanolic solutions of ICE, DOPE, cholesterol and DMG-PEG2K are mixed and diluted with ethanol to 3 mL final volume. Separately, an aqueous buffered solution (10 mM citrate/150 mM NaCl, pH 4.5) of GAA mRNA is prepared from a 1 mg/mL stock. The lipid solution is injected rapidly into the aqueous mRNA solution and shaken to yield a final suspension in 20% ethanol. The resulting nanoparticle suspension is filtered, diafiltrated with 1×PBS (pH 7.4), concentrated and stored at 2-8° C. The final concentration, $Z_{ave}$, $Dv_{(50)}$ and $Dv_{(90)}$ of the GAA encapsulated mRNA are determined.

E. HGT5001

Aliquots of 50 mg/mL ethanolic solutions of HGT5001, DOPE, cholesterol and DMG-PEG2K are mixed and diluted with ethanol to 3 mL final volume. Separately, an aqueous buffered solution (10 mM citrate/150 mM NaCl, pH 4.5) of GAA mRNA is prepared from a 1 mg/mL stock. The lipid solution is injected rapidly into the aqueous mRNA solution and shaken to yield a final suspension in 20% ethanol. The resulting nanoparticle suspension is filtered, diafiltrated with 1×PBS (pH 7.4), concentrated and stored at 2-8° C. The final concentration, $Z_{ave}$, $Dv_{(50)}$ and $Dv_{(90)}$ of the GAA encapsulated mRNA are determined.

F. HGT5000

Aliquots of 50 mg/mL ethanolic solutions of HGT5000, DOPE, cholesterol and DMG-PEG2K are mixed and diluted with ethanol to 3 mL final volume. Separately, an aqueous buffered solution (10 mM citrate/150 mM NaCl, pH 4.5) of GAA mRNA is prepared from a 1 mg/mL stock. The lipid solution is injected rapidly into the aqueous mRNA solution and shaken to yield a final suspension in 20% ethanol. The resulting nanoparticle suspension is filtered, diafiltrated with 1×PBS (pH 7.4), concentrated and stored at 2-8° C. The final concentration, $Z_{ave}$, $Dv_{(50)}$ and $Dv_{(90)}$ of the GAA encapsulated mRNA are determined.

G. DLinKC2DMA

Aliquots of 50 mg/mL ethanolic solutions of DLinKC2DMA, DOPE, cholesterol and DMG-PEG2K are mixed and diluted with ethanol to 3 mL final volume. Separately, an aqueous buffered solution (10 mM citrate/150 mM NaCl, pH 4.5) of GAA mRNA is prepared from a 1 mg/mL stock. The lipid solution is injected rapidly into the aqueous mRNA solution and shaken to yield a final suspension in 20% ethanol. The resulting nanoparticle suspension is filtered, diafiltrated with 1×PBS (pH 7.4), concentrated and stored at 2-8° C. The final concentration, $Z_{ave}$, $Dv_{(50)}$ and $Dv_{(90)}$ of the GAA encapsulated mRNA are determined.

H. DODAP

Aliquots of 50 mg/mL ethanolic solutions of DODAP, DOPE, cholesterol and DMG-PEG2K are mixed and diluted with ethanol to 3 mL final volume. Separately, an aqueous buffered solution (10 mM citrate/150 mM NaCl, pH 4.5) of GAA mRNA is prepared from a 1 mg/mL stock. The lipid solution is injected rapidly into the aqueous mRNA solution and shaken to yield a final suspension in 20% ethanol. The resulting nanoparticle suspension is filtered, diafiltrated with 1×PBS (pH 7.4), concentrated and stored at 2-8° C. The final concentration, $Z_{ave}$, $Dv_{(50)}$ and $Dv_{(90)}$ of the GAA encapsulated mRNA are determined.

I. DODMA

Aliquots of 50 mg/mL ethanolic solutions of DODMA, DOPE, cholesterol and DMG-PEG2K are mixed and diluted with ethanol to 3 mL final volume. Separately, an aqueous buffered solution (10 mM citrate/150 mM NaCl, pH 4.5) of GAA mRNA is prepared from a 1 mg/mL stock. The lipid solution is injected rapidly into the aqueous mRNA solution and shaken to yield a final suspension in 20% ethanol. The resulting nanoparticle suspension is filtered, diafiltrated with 1×PBS (pH 7.4), concentrated and stored at 2-8° C. The final concentration, $Z_{ave}$, $Dv_{(50)}$ and $Dv_{(90)}$ of the GAA encapsulated mRNA are determined.

Example 2. Intravenous Administration of GAA mRNA-Loaded Liposome Nanoparticles

This example illustrates exemplary methods of administering GAA mRNA-loaded liposome nanoparticles and methods for analyzing GAA mRNA and glycogen in various target tissues in vivo.

All studies were performed using GAA knock out mice. Mice were treated with human GAA mRNA-loaded cKK-E12-based lipid nanoparticles by a single bolus tail-vein injection of a 1.0 mg/kg dose. Mice were sacrificed and perfused with saline at 30 minutes, 3 hours, 6 hours, 12 hours, 24 hours, 48 hours, 72 hours and 7 days.

Tissues, such as liver and muscle, of each mouse were harvested, apportioned into separate parts, and stored in either 10% neutral buffered formalin or snap-frozen and stored at −80° C. for analysis.

Figure 1B:
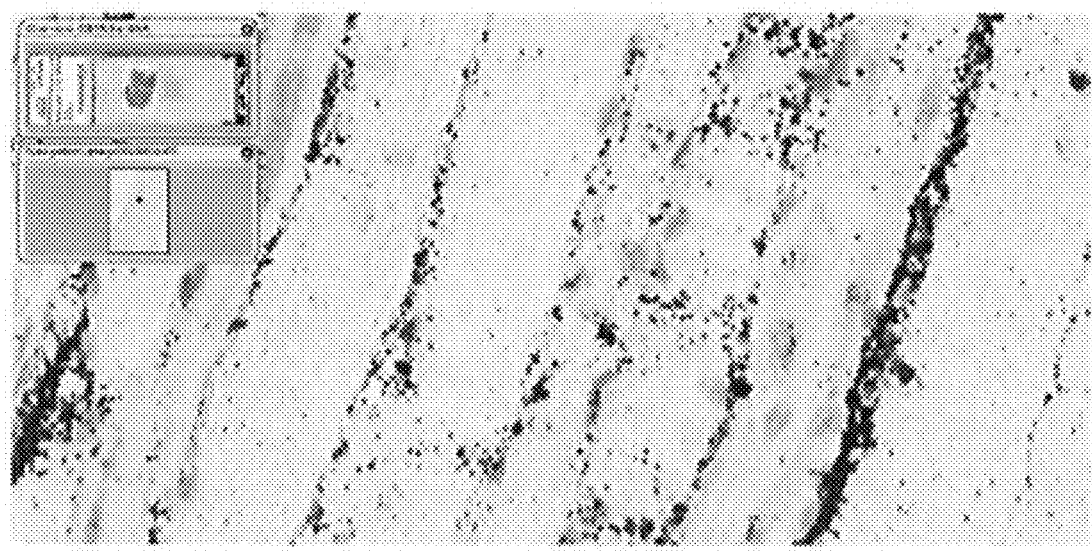

Direct detection of the active pharmaceutical ingredient (GAA mRNA) in the muscle of the treated mice was achieved using in situ hybridization (ISH) based methods. As demonstrated in FIGS. 1A and 1B, the exogenous human GAA messenger RNA was detected at 6 hours and 12 hours.

Figure 2A:
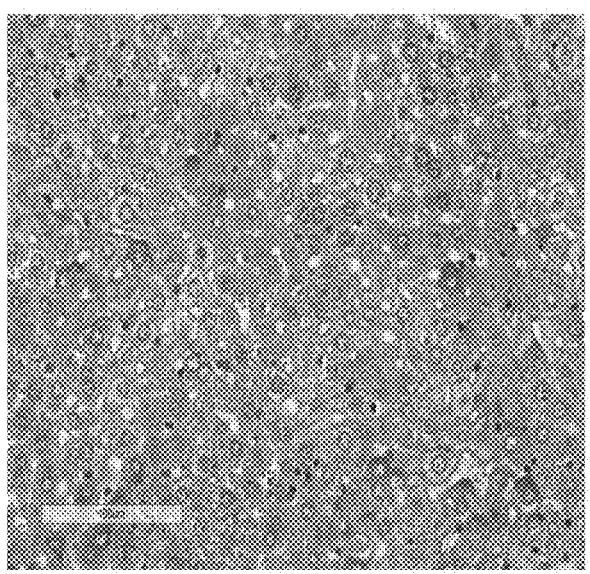
FIG. 2A depicts exemplary glycogen reduction in livers of GAA knock-out mice 24 hours after treatment with a single 1.0 mg/kg intravenous dose of GAA mRNA encapsulated lipid nanoparticles.
Figure 2B:
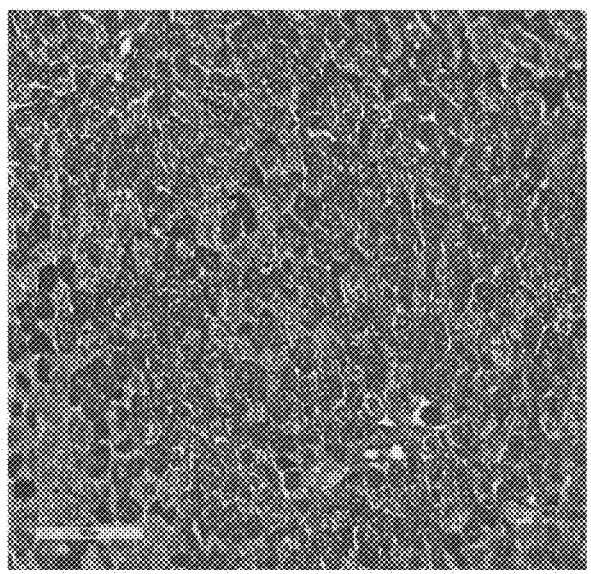
FIG. 2B depicts exemplary glycogen accumulation in livers of GAA knock-out mice that were not treated with GAA mRNA encapsulated lipid nanoparticles.

Liver glycogen levels were reduced following administration of the GAA mRNA lipid nanoparticle (FIG. 2A) as compared to liver glycogen levels in untreated GAA knock out mice (FIG. 2B).

Example 3. Intramuscular Administration of GAA mRNA-Loaded Liposome Nanoparticles This example illustrates exemplary methods of administering GAA mRNA-loaded liposome nanoparticles and methods for analyzing GAA mRNA and glycogen in various target tissues in vivo.

All studies were performed using GAA knock out mice. Mice were treated with human GAA mRNA-loaded cKK-E12-based lipid nanoparticles by a single intramuscular injection of a 1.0 mg/kg dose. Mice were sacrificed and perfused with saline at 24 hours.

Tissues, such as liver and muscle, of each mouse were harvested, apportioned into separate parts, and stored in either 10% neutral buffered formalin or snap-frozen and stored at −80° C. for analysis.

Figure 3:
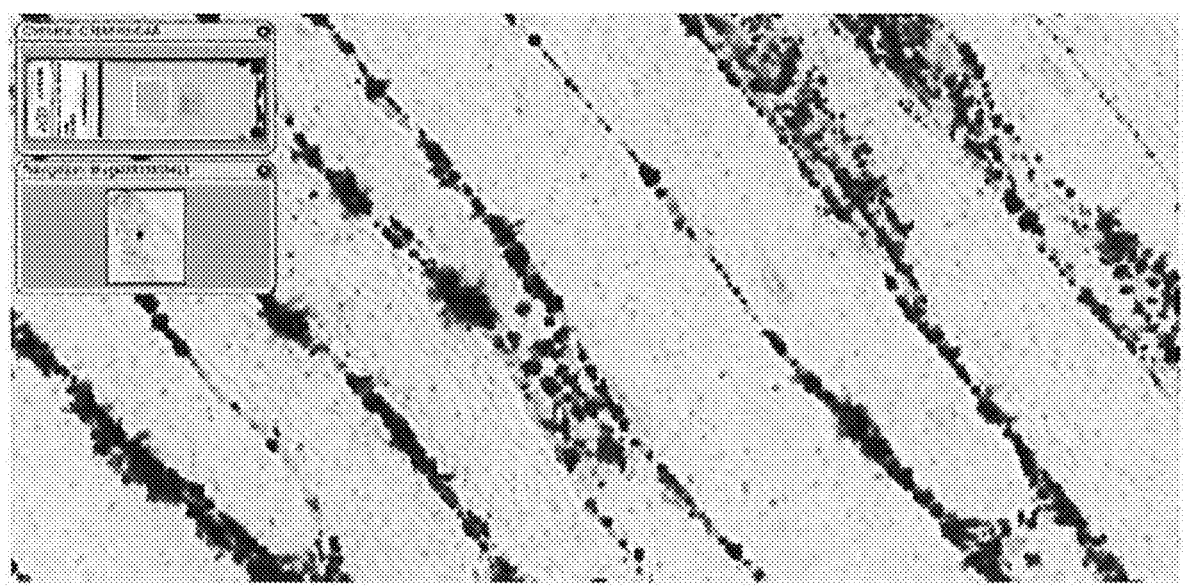
FIG. 3 depicts exemplary GAA mRNA detection by in situ hybridization in muscle tissue from mice 24 hours after treatment with a single 1.0 mg/kg intramuscular dose of GAA mRNA encapsulated lipid nanoparticles.

Direct detection of the active pharmaceutical ingredient (GAA mRNA) in the muscle of the treated mice was achieved using in situ hybridization (ISH) based methods. As demonstrated in FIG. 3, the exogenous human GAA messenger RNA was detected at high levels at 24 hours.

Figure 4A:
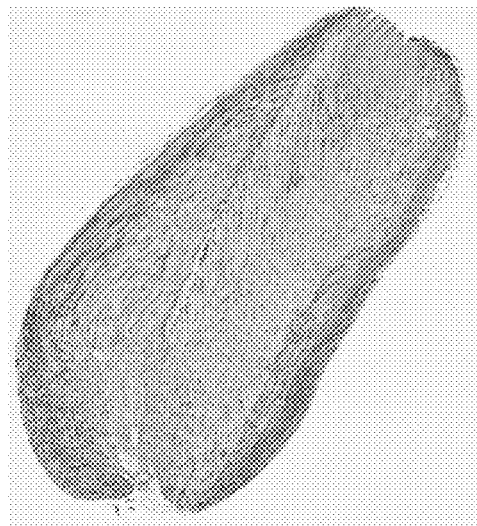
FIGS. 4A-4B depict exemplary glycogen reduction in quadriceps muscle of GAA knock-out mice 24 hours after treatment with a single 1.0 mg/kg intramuscular dose of GAA mRNA encapsulated lipid nanoparticles.
Figure 4B:
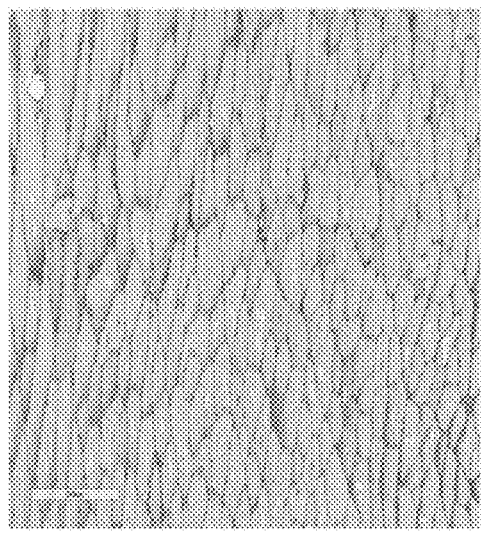
Figure 4C:
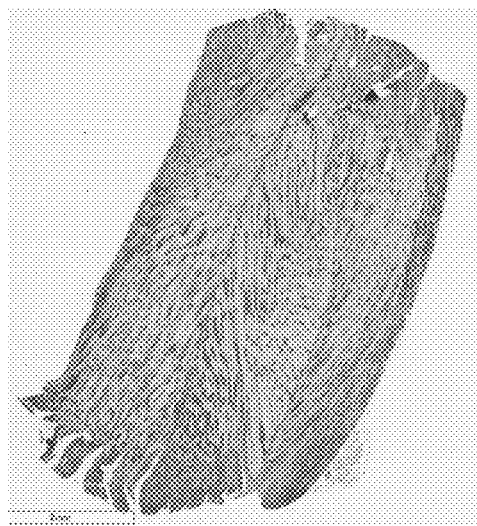
FIGS. 4C-4D depict exemplary glycogen levels in quadriceps muscle of GAA knock-out mice that were not treated with GAA mRNA encapsulated lipid nanoparticles.
Figure 4D:
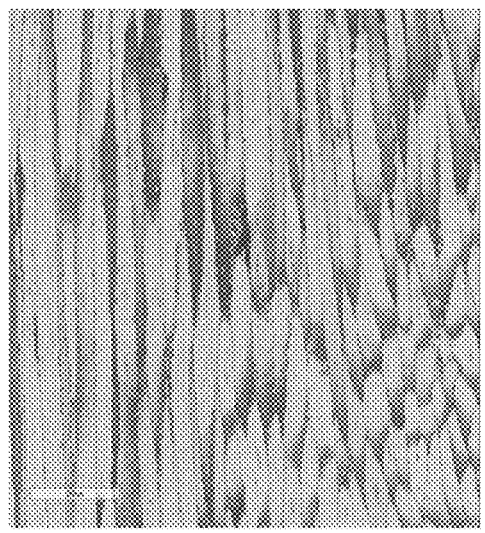

Quadriceps muscle glycogen levels were reduced following administration of the GAA mRNA lipid nanoparticle (FIGS. 4A and 4B) as compared to quadriceps muscle glycogen levels in untreated GAA knock out mice (FIGS. 4C and 4D).

EQUIVALENTS

Those skilled in the art will recognize, or be able to ascertain using no more than routine experimentation, many equivalents to the specific embodiments of the invention described herein. The scope of the present invention is not intended to be limited to the above Description, but rather is as set forth in the following claims.

We claim:

1. A method of treating Pompe disease, comprising administering to a subject in need of treatment a composition comprising an mRNA encoding acid alpha-glucosidase (GAA) at an effective dose and an administration interval such that at least one symptom or feature of Pompe disease is reduced in intensity, severity, or frequency or has delayed onset, wherein the mRNA is at least 90% identical to SEQ ID NO: 3.

2. The method of claim 1, wherein administering the composition results in treatment of hypertrophic cardiomyopathy in the subject.

3. The method of claim 1, wherein the mRNA is encapsulated within a liposome.

4. The method of claim 3, wherein the liposome comprises one or more cationic lipids, one or more non-cationic lipids, one or more cholesterol-based lipids and one or more PEG-modified lipids.

5. The method of claim 4, wherein the one or more PEG-modified lipids comprise a poly(ethylene) glycol chain of up to 5 kDa in length covalently attached to a lipid with alkyl chain(s) of $C_6$-$C_{20}$ length.

6. The method of claim 4, wherein the cationic lipid constitutes about 30-50% of the liposome by weight.

7. The method of claim 1, wherein the mRNA is administered at the effective dose ranging from about 0.1-5.0 mg/kg body weight.

8. The method of claim 1, wherein the composition is administered intravenously.

9. The method of claim 1, wherein the composition is administered intramuscularly.

10. The method of claim 1 wherein the administering of the composition results in GAA protein expression in liver.

11. The method of claim 1, wherein the administering of the composition results in GAA protein expression in serum.

12. The method of claim 1, wherein the mRNA is codon optimized.

13. The method of claim 1, wherein the mRNA comprises one or more modified nucleotides.

14. The method of claim 1, wherein the mRNA is unmodified.

15. A composition for treating Pompe disease, comprising an mRNA encoding acid alpha-glucosidase (GAA) at an effective dose amount encapsulated within a liposome, wherein the mRNA is at least 90% identical to SEQ ID NO: 3, and wherein the liposome comprises a cationic lipid cKK-E12:

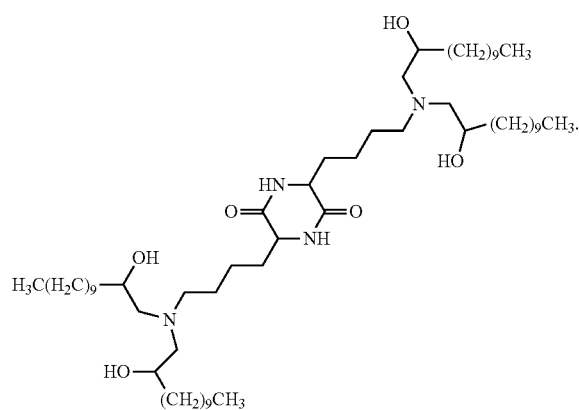

16. The composition of claim 15, wherein the liposome further comprises one or more non-cationic lipids, one or more cholesterol-based lipids, and one or more PEG-modified lipids.

17. The composition of claim 15, wherein the cationic lipid constitutes about 30-50% of the liposome by molar ratio.

18. The composition of claim 15, wherein the composition is formulated for intravenous administration.

19. A composition for treating Pompe disease, comprising an mRNA encoding acid alpha-glucosidase (GAA) at an effective dose amount encapsulated within a liposome, wherein the mRNA is at least 90% identical to SEQ ID NO: 3, and further wherein the liposome comprises cationic or non-cationic lipid, cholesterol-based lipid and PEG-modified lipid.

20. The composition of claim 19, wherein the mRNA further comprises SEQ ID NO: 8 and SEQ ID NO: 9, or SEQ ID NO: 10.

* * * * *

SEQUENCE LISTING

```
<160> NUMBER OF SEQ ID NOS: 12

<210> SEQ ID NO 1
<211> LENGTH: 2859
<212> TYPE: RNA
<213> ORGANISM: Homo sapiens

<400> SEQUENCE: 1
augggaguga ggcacccgcc cugcucccac cggcuccugg ccgucugcgc ccucguguc     60 uuggcaaccg cugcacuccu ggggcacauc cuacuccaug auuuccugcu gguucccga    120 gagcugagug gcuccucccc aguccuggag gagacucacc cagcucacca gcagggagcc   180
agcagaccag ggcccccggga ugcccaggca caccccggcc guccagagc agugcccaca    240 cagugcgacg uccccccaa cagccgcuuc gauugcgccc cugacaaggc caucacccag    300
gaacagugcg aggcccgcgg cuguugcuac aucccugcaa agcaggggcu gcagggagcc    360
```

```
cagaugggc  agcccuggug  cuucuuccca  cccagcuacc  ccagcuacaa  gcuggagaac    420
cugagcuccu  cugaaauggg  cuacacggcc  acccugaccc  guaccacccc  caccuucuuc    480
cccaaggaca  uccugacccu  gcggcuggac  gugaugaugg  agacugagaa  ccgccuccac    540
uucacgauca  aagauccagc  uaacaggcgc  uacgaggugc  ccuuggagac  cccgcauguc    600
cacagccggg  caccgucccc  acucuacagc  guggaguucu  ccgaggagcc  cuucggggug    660
aucgugcgcc  ggcagcugga  cggccgcgug  cugcugaaca  cgacgguggc  gcccuguuc    720 uuugcggacc  aguccuuca  gcugccacc  ucgcugcccu  cgcaguauau  cacaggccuc    780
gccgagcacc  ucagucccu  gaugcucagc  accagcugga  ccaggaucac  ccuguggaac    840
cgggaccuug  cgcccacgcc  cggugcgaac  ucuacgggu  cuacccuuu  cuaccuggcg    900 cuggaggacg  gcgggucggc  acacgggug  uccugcuaa  acagcaaugc  cauggaugug    960
guccugcagc  cgagcccugc  ccuuagcugg  aggucgacag  gugggauccu  ggaugcuac    1020 aucuuccugg  gccagagcc  caagagcgug  gugcagcagu  accugacgu  ugugggauac    1080 ccguucaugc  cgccauacug  gggccugggc  uuccaccugu  gccgcugggg  cuacuccucc    1140
accgcuauca  cccgccaggu  ggugagaaac  augaccaggg  cccacuuccc  ccuggacguc    1200 cagguggaacg  accuggacua  cauggacucc  cggagggacu  ucacguucaa  caaggauggc    1260
uuccgggacu  uccggccau  ggugcaggag  cugcaccagg  gcggccggcg  cuacaugaug    1320
aucguggauc  cugccaucag  cagcucgggc  ccugccggga  gcuacaggcc  cuacgacgag    1380
ggucugcgga  gggggguuuu  caucaccaac  gagaccggcc  agccgcugau  ugggaaggua    1440
uggcccgggu  ccacugccuu  cccccgacuuc  accaacccca  cagcccuggc  cugguggag    1500 gacaugugg  cugaguucca  ugaccaggug  cccuucgacg  gcaugugau  ugacaugaac    1560 gagccuucca  acuucaucag  gggcucgag  gacggcugcc  ccaacaauga  gcuggagaac    1620
ccacccuacg  ugccugggu  gguugggggg  acccuccagg  cggccaccau  cugugccucc    1680
agccaccagu  uucucuccac  acacuacaac  cugcacaacc  ucuacggccu  gaccgaagcc    1740 aucgccucc  acagggcgcu  ggugaaggcu  cgggggacac  gcccauuugu  gaucucccgc    1800
ucgaccuuug  cuggccacgg  ccgauacgcc  ggccacugga  cggggacgu  guggagcucc    1860 ugggagcagc  ucgccuccuc  cgugccagaa  auccugcagu  uuaaccugcu  ggggugccu    1920 cuggucgggg  ccgacgucug  cggcuuccug  ggcaacaccu  cagaggagcu  gugugugcgc    1980
uggacccagc  uggggccuu  cuacccuucc  augcggaacc  acaacagccu  gcucagucug    2040
ccccaggagc  cguacagcuu  cagcgagccg  gccagcagg  ccaugaggaa  ggcccucacc    2100
cugcgcuacg  cacuccuccc  ccaccucuac  acacuguucc  accaggccca  cgucgcgggg    2160
gagaccgugg  cccggccccu  cuuccuggag  uccccaagg  acucuagcac  cuggacugug    2220
gaccaccagc  uccuguggg  ggaggcccug  cucaucaccc  cagugcucca  ggccgggaag    2280
gccgaaguga  cuggcuacuu  cccccuuggc  acauggaugg  accugcagac  ggugccagua    2340
gaggcccuug  gcagccuccc  accccaccu  gcagcuccccc  gugagccagc  cauccacagc    2400 gagggggcagu  gggugacgcu  gccggccccc  cuggacacca  ucaacgucca  ccucggggcu    2460
ggguacauca  uccccugca  gggccccuggc  cucacaacca  cagagucccg  ccagcagccc    2520
auggcccugg  cuguggcccu  gaccaagggu  ggggaggccc  gagggagcu  guucugggac    2580 gauggagaga  gccuggaagu  gcuggagcga  ggggccuaca  cacaggucau  cuuccuggcc    2640
aggaauaaca  cgaucgugaa  ugagcuggua  cgugugacca  gugagggagc  uggccugcag    2700
```

```
cugcagaagg ugacuguccu gggcguggcc acggcgcccc agcagguccu cuccaacggu    2760
gucccugucu ccaacuucac cuacagcccc gacaccaagg uccuggacau cugugucucg    2820
cuguugaugg gagagcaguu ucucgucagc ugguguuag                           2859
```

<210> SEQ ID NO 2
<211> LENGTH: 952
<212> TYPE: PRT
<213> ORGANISM: Homo sapiens

<400> SEQUENCE: 2

```
Met Gly Val Arg His Pro Pro Cys Ser His Arg Leu Leu Ala Val Cys
1               5                   10                  15

Ala Leu Val Ser Leu Ala Thr Ala Ala Leu Leu Gly His Ile Leu Leu
            20                  25                  30

His Asp Phe Leu Leu Val Pro Arg Glu Leu Ser Gly Ser Ser Pro Val
        35                  40                  45

Leu Glu Glu Thr His Pro Ala His Gln Gln Gly Ala Ser Arg Pro Gly
    50                  55                  60

Pro Arg Asp Ala Gln Ala His Pro Gly Arg Pro Arg Ala Val Pro Thr
65                  70                  75                  80

Gln Cys Asp Val Pro Pro Asn Ser Arg Phe Asp Cys Ala Pro Asp Lys
                85                  90                  95

Ala Ile Thr Gln Glu Gln Cys Glu Ala Arg Gly Cys Cys Tyr Ile Pro
            100                 105                 110

Ala Lys Gln Gly Leu Gln Gly Ala Gln Met Gly Gln Pro Trp Cys Phe
        115                 120                 125

Phe Pro Pro Ser Tyr Pro Ser Tyr Lys Leu Glu Asn Leu Ser Ser Ser
    130                 135                 140

Glu Met Gly Tyr Thr Ala Thr Leu Thr Arg Thr Thr Pro Thr Phe Phe
145                 150                 155                 160

Pro Lys Asp Ile Leu Thr Leu Arg Leu Asp Val Met Met Glu Thr Glu
                165                 170                 175

Asn Arg Leu His Phe Thr Ile Lys Asp Pro Ala Asn Arg Arg Tyr Glu
            180                 185                 190

Val Pro Leu Glu Thr Pro His Val His Ser Arg Ala Pro Ser Pro Leu
        195                 200                 205

Tyr Ser Val Glu Phe Ser Glu Glu Pro Phe Gly Val Ile Val Arg Arg
    210                 215                 220

Gln Leu Asp Gly Arg Val Leu Leu Asn Thr Thr Val Ala Pro Leu Phe
225                 230                 235                 240

Phe Ala Asp Gln Phe Leu Gln Leu Ser Thr Ser Leu Pro Ser Gln Tyr
                245                 250                 255

Ile Thr Gly Leu Ala Glu His Leu Ser Pro Leu Met Leu Ser Thr Ser
            260                 265                 270

Trp Thr Arg Ile Thr Leu Trp Asn Arg Asp Leu Ala Pro Thr Pro Gly
        275                 280                 285

Ala Asn Leu Tyr Gly Ser His Pro Phe Tyr Leu Ala Leu Glu Asp Gly
    290                 295                 300

Gly Ser Ala His Gly Val Phe Leu Leu Asn Ser Asn Ala Met Asp Val
305                 310                 315                 320

Val Leu Gln Pro Ser Pro Ala Leu Ser Trp Arg Ser Thr Gly Gly Ile
                325                 330                 335

Leu Asp Val Tyr Ile Phe Leu Gly Pro Glu Pro Lys Ser Val Val Gln
            340                 345                 350
```

-continued

```
Gln Tyr Leu Asp Val Val Gly Tyr Pro Phe Met Pro Pro Tyr Trp Gly
        355                 360                 365

Leu Gly Phe His Leu Cys Arg Trp Gly Tyr Ser Ser Thr Ala Ile Thr
        370                 375                 380

Arg Gln Val Val Glu Asn Met Thr Arg Ala His Phe Pro Leu Asp Val
385                 390                 395                 400

Gln Trp Asn Asp Leu Asp Tyr Met Asp Ser Arg Arg Asp Phe Thr Phe
                405                 410                 415

Asn Lys Asp Gly Phe Arg Asp Phe Pro Ala Met Val Gln Glu Leu His
                420                 425                 430

Gln Gly Gly Arg Arg Tyr Met Met Ile Val Asp Pro Ala Ile Ser Ser
        435                 440                 445

Ser Gly Pro Ala Gly Ser Tyr Arg Pro Tyr Asp Glu Gly Leu Arg Arg
        450                 455                 460

Gly Val Phe Ile Thr Asn Glu Thr Gly Gln Pro Leu Ile Gly Lys Val
465                 470                 475                 480

Trp Pro Gly Ser Thr Ala Phe Pro Asp Phe Thr Asn Pro Thr Ala Leu
                485                 490                 495

Ala Trp Trp Glu Asp Met Val Ala Glu Phe His Asp Gln Val Pro Phe
        500                 505                 510

Asp Gly Met Trp Ile Asp Met Asn Glu Pro Ser Asn Phe Ile Arg Gly
        515                 520                 525

Ser Glu Asp Gly Cys Pro Asn Asn Glu Leu Glu Asn Pro Pro Tyr Val
530                 535                 540

Pro Gly Val Val Gly Gly Thr Leu Gln Ala Ala Thr Ile Cys Ala Ser
545                 550                 555                 560

Ser His Gln Phe Leu Ser Thr His Tyr Asn Leu His Asn Leu Tyr Gly
                565                 570                 575

Leu Thr Glu Ala Ile Ala Ser His Arg Ala Leu Val Lys Ala Arg Gly
        580                 585                 590

Thr Arg Pro Phe Val Ile Ser Arg Ser Thr Phe Ala Gly His Gly Arg
        595                 600                 605

Tyr Ala Gly His Trp Thr Gly Asp Val Trp Ser Ser Trp Glu Gln Leu
        610                 615                 620

Ala Ser Ser Val Pro Glu Ile Leu Gln Phe Asn Leu Leu Gly Val Pro
625                 630                 635                 640

Leu Val Gly Ala Asp Val Cys Gly Phe Leu Gly Asn Thr Ser Glu Glu
                645                 650                 655

Leu Cys Val Arg Trp Thr Gln Leu Gly Ala Phe Tyr Pro Phe Met Arg
                660                 665                 670

Asn His Asn Ser Leu Leu Ser Leu Pro Gln Glu Pro Tyr Ser Phe Ser
                675                 680                 685

Glu Pro Ala Gln Gln Ala Met Arg Lys Ala Leu Thr Leu Arg Tyr Ala
        690                 695                 700

Leu Leu Pro His Leu Tyr Thr Leu Phe His Gln Ala His Val Ala Gly
705                 710                 715                 720

Glu Thr Val Ala Arg Pro Leu Phe Leu Glu Phe Pro Lys Asp Ser Ser
                725                 730                 735

Thr Trp Thr Val Asp His Gln Leu Leu Trp Gly Glu Ala Leu Leu Ile
                740                 745                 750

Thr Pro Val Leu Gln Ala Gly Lys Ala Glu Val Thr Gly Tyr Phe Pro
        755                 760                 765
```

```
Leu Gly Thr Trp Tyr Asp Leu Gln Thr Val Pro Val Glu Ala Leu Gly
770                 775                 780

Ser Leu Pro Pro Pro Ala Ala Pro Arg Glu Pro Ala Ile His Ser
785                 790                 795                 800

Glu Gly Gln Trp Val Thr Leu Pro Ala Pro Leu Asp Thr Ile Asn Val
                805                 810                 815

His Leu Arg Ala Gly Tyr Ile Ile Pro Leu Gln Gly Pro Gly Leu Thr
            820                 825                 830

Thr Thr Glu Ser Arg Gln Gln Pro Met Ala Leu Ala Val Ala Leu Thr
        835                 840                 845

Lys Gly Gly Glu Ala Arg Gly Glu Leu Phe Trp Asp Asp Gly Glu Ser
850                 855                 860

Leu Glu Val Leu Glu Arg Gly Ala Tyr Thr Gln Val Ile Phe Leu Ala
865                 870                 875                 880

Arg Asn Asn Thr Ile Val Asn Glu Leu Val Arg Val Thr Ser Glu Gly
                885                 890                 895

Ala Gly Leu Gln Leu Gln Lys Val Thr Val Leu Gly Val Ala Thr Ala
            900                 905                 910

Pro Gln Gln Val Leu Ser Asn Gly Val Pro Val Ser Asn Phe Thr Tyr
        915                 920                 925

Ser Pro Asp Thr Lys Val Leu Asp Ile Cys Val Ser Leu Leu Met Gly
    930                 935                 940

Glu Gln Phe Leu Val Ser Trp Cys
945                 950

<210> SEQ ID NO 3
<211> LENGTH: 2859
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 3
augggaguca gacacccgcc gugcucgcac aggcuucugg ccgugugcgc acucgugagu    60
cuggcgacug cugcguugcu ggggcacauu cuucuccacg acuuucucuu ggugccccga   120
gaauugucgg gcucgucgcc gguacuggaa gaaacccacc ccgcacauca gcagggcgcg   180
ucgcggccug gucgaggga ugcccaggca caucccggaa ggccacgagc cgucccgacu   240
caaugugacg uaccucccaa uucccgguuc gacugugcgc cagacaaggc aaucacgcaa   300
gagcagugcg aagcccgugg augcugcuau auuccggcga agcagggacu ucagggagcc   360
cagauggggc agcccuggug uucuuucccg ccuuccuauc ccucauauaa gcuggagaau   420
uugucguccu cggaaauggg guauaccgcu acucuuacga gaaccacccc cacauucuuu   480
ccgaaggaca uccuuacucu gcggcucgac gugaugaugg agacagaaaa uaggcugcau   540
uucacgauca aagacccggc gaaccggaga uaugagguuc gcuugagac ucccacguu    600 cacucucgug cgccuucacc cuuguacucc guggaguucu cggaagaacc guucggggug   660
aucgucagac ucaacuuga ugguagggua uugcugaaca caacggucgc ccccuuguuu   720
uucgccgacc aguuucugca gcuuucgaca ucgcugccgu cccaguauau cacagggcuc   780
gcggagcauc uuucaccccu caugcugagc acgagcugga cacggauuac gcucuggaac   840
agggaucucg cgccgacgcc cggagcgaau uguauggggu cgcaucccuu cuaccucgca   900
uuggaagacg ggguuccgc gcacggagua uuccugcuua auucuaaagc gauggacguu   960
```

| | |
|---|---|
| gucuugcagc ccuccccugc uuugucgugg cguccacgg ggggcauuuu ggacguuuac | 1020 |
| aucuuuugg gacccgagcc aaagagcgua gugcagcagu auuuggaugu aguggggcuac | 1080 |
| cccuucaugc cgccuuauug gggacugggg uuccaucucu gccgcugggg guacucuucg | 1140 |
| accgcgauca cccgccaggu ggucgagaac augaccagag cacauuuccc uuuggacgug | 1200 |
| caguggaaug auuuggauua cauggauagc cgaagagacu ucacguucaa uaaggacggg | 1260 |
| uuuagagauu uucccgcgau ggugcaagaa uugcaccagg gugggcgcag auacaugaug | 1320 |
| aucgucgauc ccgccaucag cagcucggga ccagcgggga guuaccggcc uuacgaugag | 1380 |
| ggacuuagga gaggcgucuu uaucacgaac gaaacagguc agccgcucau ugguaaagug | 1440 |
| uggccuggau caacggccuu ucccgacuuc acgaauccca cagcccucgc cuggugggaa | 1500 |
| gacauggugg cggaguuuca cgaccaagua ccguuugaug ggauguggau ugauaugaac | 1560 |
| gaacccucaa acuuuauucg cggcucggaa gauggaugcc cgaauaauga gcuugagaau | 1620 |
| cccccguaug ugccaggggu gguaggugggg acgcuccagg ccgcuacgau cugugcguca | 1680 |
| ucaucagu ucuugucaac gcacuacaac uugcacaauc uuuacgguuu gacugaagcc | 1740 |
| aucgcuucgc aucgcgcgcu ggucaaagcg cguggacgc gacccuucgu uauuucucgg | 1800 |
| uccacauuug ccgggcacgg ucggauugcc ggacacugga cggagagugu cuggucuagc | 1860 |
| ugggagcagc ucgcgucgag cguaccggag auccuccagu ucaaucuuuu gggaguuccg | 1920 |
| cucgucggcg cugacgugug cgguuuucuc ggaaacacau cagaagagcu ugcguacgc | 1980 |
| uggacacagc ucggugcguu uuaccccuuu augagaaacc auaacucguu gcucucacuc | 2040 |
| ccucaagagc cguacaguuu uucggagccu gcgcaacagg cgaugcggaa ggcauugaca | 2100 |
| cuucgcuaug cacugcuccc gcaucucuau acucuguucc aucaggccca uguggcugga | 2160 |
| gaaacggugg cgaggccccu guucuuggag uccccaaag auaguccac auggaccgug | 2220 |
| gaucaccagu ugcuguggggg agaggcgcuu cugaucacuc cgguacuuca ggcggguaaa | 2280 |
| gcggaaguca cugggguauuu cccgcuuggg accgguacg accuucagac ugucccagua | 2340 |
| gaagcccucg gaagccugcc accucccccu gcugcacccc gcgagccugc aauccauagc | 2400 |
| gagggccagu ggguaacguu gccagcccca cuggauacca ucaaugucca ccucagggcg | 2460 |
| gguuacauua ucccucucca aggcccuggg uugaccacca cagagucgcg ccagcagcca | 2520 |
| auggcacuug cggucgcauu gacgaaaggg ggugaagccc gaggggaacu guuugggau | 2580 |
| gacggggaaa gccuugaggu gcuggaacgg ggagcguaca cacaagucau uuucuuggcc | 2640 |
| aggaacaaca cuauugucaa cgaguuggug cgcgugaccu cugagggugc cggacugcaa | 2700 |
| cugcagaagg ucacggnuccu cggaguggcg acagcacccc aacagguccu uaguaacgga | 2760 |
| guaccugucu cgaacuuuac auacuccccg gacacgaagg ugcucgacau cugugugucg | 2820 |
| cugcuuaugg gggaacaguu ucucgugagc uggugcuag | 2859 |

<210> SEQ ID NO 4
<211> LENGTH: 300
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(300)
<223> OTHER INFORMATION: This sequence may encompass 10-300 nucleotides

<400> SEQUENCE: 4
aaaaaaaaaa aaaaaaaaaa aaaaaaaaaa aaaaaaaaaa aaaaaaaaaa aaaaaaaaaa        60
aaaaaaaaaa aaaaaaaaaa aaaaaaaaaa aaaaaaaaaa aaaaaaaaaa aaaaaaaaaa       120
aaaaaaaaaa aaaaaaaaaa aaaaaaaaaa aaaaaaaaaa aaaaaaaaaa aaaaaaaaaa       180
aaaaaaaaaa aaaaaaaaaa aaaaaaaaaa aaaaaaaaaa aaaaaaaaaa aaaaaaaaaa       240
aaaaaaaaaa aaaaaaaaaa aaaaaaaaaa aaaaaaaaaa aaaaaaaaaa aaaaaaaaaa       300

<210> SEQ ID NO 5
<211> LENGTH: 200
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(200)
<223> OTHER INFORMATION: This sequence may encompass 10-200 nucleotides

<400> SEQUENCE: 5
cccccccccc cccccccccc cccccccccc cccccccccc cccccccccc cccccccccc        60
cccccccccc cccccccccc cccccccccc cccccccccc cccccccccc cccccccccc       120
cccccccccc cccccccccc cccccccccc cccccccccc cccccccccc cccccccccc       180
cccccccccc cccccccccc                                                   200

<210> SEQ ID NO 6
<211> LENGTH: 500
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(500)
<223> OTHER INFORMATION: This sequence may encompass 10-500 nucleotides

<400> SEQUENCE: 6
aaaaaaaaaa aaaaaaaaaa aaaaaaaaaa aaaaaaaaaa aaaaaaaaaa aaaaaaaaaa        60
aaaaaaaaaa aaaaaaaaaa aaaaaaaaaa aaaaaaaaaa aaaaaaaaaa aaaaaaaaaa       120
aaaaaaaaaa aaaaaaaaaa aaaaaaaaaa aaaaaaaaaa aaaaaaaaaa aaaaaaaaaa       180
aaaaaaaaaa aaaaaaaaaa aaaaaaaaaa aaaaaaaaaa aaaaaaaaaa aaaaaaaaaa       240
aaaaaaaaaa aaaaaaaaaa aaaaaaaaaa aaaaaaaaaa aaaaaaaaaa aaaaaaaaaa       300
aaaaaaaaaa aaaaaaaaaa aaaaaaaaaa aaaaaaaaaa aaaaaaaaaa aaaaaaaaaa       360
aaaaaaaaaa aaaaaaaaaa aaaaaaaaaa aaaaaaaaaa aaaaaaaaaa aaaaaaaaaa       420
aaaaaaaaaa aaaaaaaaaa aaaaaaaaaa aaaaaaaaaa aaaaaaaaaa aaaaaaaaaa       480
aaaaaaaaaa aaaaaaaaaa                                                   500

<210> SEQ ID NO 7
<211> LENGTH: 250
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 7
aaaaaaaaaa aaaaaaaaaa aaaaaaaaaa aaaaaaaaaa aaaaaaaaaa aaaaaaaaaa        60

```
aaaaaaaaaa aaaaaaaaaa aaaaaaaaaa aaaaaaaaaa aaaaaaaaaa aaaaaaaaaa        120
aaaaaaaaaa aaaaaaaaaa aaaaaaaaaa aaaaaaaaaa aaaaaaaaaa aaaaaaaaaa        180
aaaaaaaaaa aaaaaaaaaa aaaaaaaaaa aaaaaaaaaa aaaaaaaaaa aaaaaaaaaa        240
aaaaaaaaaa                                                               250

<210> SEQ ID NO 8
<211> LENGTH: 140
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 8
ggacagaucg ccuggagacg ccauccacgc uguuugacc uccauagaag acaccgggac          60
cgauccagcc uccgcggccg ggaacggugc auuggaacgc ggauucccg ugccaagagu        120 gacucaccgu ccuugacacg                                                   140

<210> SEQ ID NO 9
<211> LENGTH: 105
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 9
cggguggcau cccugugacc ccuccccagu gccucuccug gcccuggaag uugccacucc         60
agugcccacc agccuuguuc uaauaaaauu aaguugcauc aagcu                       105

<210> SEQ ID NO 10
<211> LENGTH: 105
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 10
ggguggcauc ccugugaccc cuccccagug ccucuccugg cccuggaagu ugccacucca         60
gugcccacca gccuuguccu aauaaaauua aguugcauca aagcu                       105

<210> SEQ ID NO 11
<211> LENGTH: 3104
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 11
ggacagaucg ccuggagacg ccauccacgc uguuugacc uccauagaag acaccgggac          60
cgauccagcc uccgcggccg ggaacggugc auuggaacgc ggauucccg ugccaagagu        120 gacucaccgu ccuugacacg augggaguca gacaccgcc gugcucgcac aggcuucugg        180
ccgugugcgc acucgugagu cuggcgacug cugcguugcu ggggcacauu cuucuccacg       240
acuuucucuu ggugccccga gaauugucgg gcucgucgcc gguacuggaa gaaacccacc       300
ccgcacauca gcagggcgcg ucgcggccug gucgaggga ugcccaggca cauccccgaa        360
ggccacgagc cgucccgacu caaugugacg uaccuccaa uucccgguuc gacugugcgc       420
```

```
cagacaaggc aaucacgcaa gagcagugcg aagcccgugg augcugcuau auuccggcga      480
agcagggacu ucagggagcc cagaugggc agcccuggug uuucuucccg ccuuccuauc       540
ccucauauaa gcuggagaau uugucguccu cggaaauggg guauaccgcu acucuuacga      600
gaaccacccc cacauucuuu ccgaaggaca uccuuacucu gcggcucgac gugaugaugg      660
agacagaaaa uaggcugcau uucacgauca aagacccggc gaaccggaga uaugagguuc      720
cgcuugagac uccccacguu cacucucgug cgccuucacc cuuguacucc guggaguucu      780
cggaagaacc guucggggug aucgucagac gucaacuuga ugguagggua uugcugaaca      840
caacggucgc ccccuuguuu uucgccgacc aguuucugca gcuuucgaca ucgcugccgu      900
cccaguauau cacagggcuc gcggagcauc uuucacccu caugcugagc acgagcugga      960
cacggauuac gcucuggaac agggaucucg cgccgacgcc cggagcgaau uuguauggu      1020 cgcaucccuu cuaccucgca uuggaagacg ggguuccgc gcacggagua uuccugcuua      1080
auucuaaugc gauggacguu gucuugcagc ccuccccugc uuugucgugg cguccacgg      1140 ggggcauuuu ggacguuuac aucuuuuugg acccgagcc aaagagcgua gugcagcagu      1200
auuuggaugu agugggcuac cccuucaugc cgccuuauug gggacugggg uuccaucucu      1260
gccgcugggg guacucuucg accgcgauca cccgccaggu ggucgagaac augaccagag      1320
cacauuuccc uuuggacgug caguggaaug auuuggauua cauggauagc cgaagagacu      1380
ucacguucaa uaaggacggg uuuagagauu uucccgcgau ggugcaagaa uugcaccagg      1440
gugggcgcag auacaugaug aucgucgauc ccgccaucag cagcucggga ccagcgggga      1500
guuaccggcc uuacgaugag ggacuuagga gaggcgucuu uaucacgaac gaaacaagguc      1560 agccgcucau ugguaaagug uggccuggau caacggccuu ucccgacuuc acgaauccca      1620
cagcccucgc cugguggaa gacauggugg cggaguuuca cgaccaagua ccguuugaug      1680
ggauguggau ugauaugaac gaaccccaa acuuuauucg cggcucgaaa gauggaugcc      1740
cgaauaauga gcuugagaau cccccguaug ugccaggggu gguaggguggg acgcuccagg      1800 ccgcuacgau cugugcguca ucaucagu ucuugcaac gcacuacaac uugcacaauc      1860
uuuacgguuu gacugaagcc aucgcuucgc aucgcgcgcu ggucaaagcg cguggguacgc      1920 gacccuucgu uauuucucgg uccacauuug ccgggcacgg ucggauugcc ggacacugga      1980
cgggagaugu cuggucuagc ugggagcagc ucgcgucgag cguaccggag auccuccagu      2040
ucaaucuuuu gggaguuccg cucgucggcg cugacgugug cgguuuucuc ggaaacacau      2100
cagaagagcu uugcguacgc uggacacagc ucggugcguu uuaccccuuu augagaaacc      2160
auaacucguu gcucucacuc ccucaagagc cguacaguuu ucggagccu gcgcaacagg      2220 cgaugcggaa ggcauugaca cuucgcuaug cacugcuccc gcaucucuau acucuguucc      2280
aucaggccca uguggcugga aaacggugg cgaggcccu guucuuggag uuccccaaag      2340
auaguuccac auggaccgug gaucaccagu ugcugggggg agaggcgcuu cugaucacuc      2400
cgguacuuca ggcggguaaa gcggaaguca cuggguauuu cccgcuuggg accgguacg      2460 accuucagac uguccagua gaagcccucg gaagccugcc accuccccu gcugcacccc      2520 gcgagccugc aauccauagc gagggccagu ggguaacguu gccagcccca cuggauacca      2580
ucaaugucca ccucagggcg gguuacauua ucccucucca aggcccuggg uugaccacca      2640
cagagucgcg ccagcagcca auggcacuug cggucgcauu gacgaaaggg ggugaagccc      2700 gagggaacu guuuugggau gacggggaaa gccuugaggu gcuggaacgg ggagcguaca      2760
```

| | |
|---|---|
| cacaagucau uuucuuggcc aggaacaaca cuauugucaa cgaguuggug cgcgugaccu | 2820 |
| cugagggugc cggacugcaa cugcagaagg ucacggaccu cggaguggcg acagcacccc | 2880 |
| aacagguccu aguaacgga guaccugucu cgaacuuuac auacucccccg gacacgaagg | 2940 |
| ugcucgacau cugugugucg cugcuuaugg gggaacaguu ucucgugagc ugguugcuagc | 3000 |
| ggguggcauc ccugugaccc cuccccagug ccucuccugg cccuggaagu ugccacucca | 3060 |
| gugcccacca gccuugaccu aauaaaauua aguugcauca agcu | 3104 |

<210> SEQ ID NO 12
<211> LENGTH: 3104
<212> TYPE: RNA
<213> ORGANISM: Artificial Sequence
<220> FEATURE:
<223> OTHER INFORMATION: Description of Artificial Sequence: Synthetic
 polynucleotide

<400> SEQUENCE: 12

| | |
|---|---|
| ggacagaucg ccuggagacg ccauccacgc uguuuugacc uccauagaag acaccgggac | 60 |
| cgauccagcc uccgcggccg ggaacggugc auuggaacgc ggauccccg ugccaagagu | 120 |
| gacucaccgu ccuugacacg auggagguca gacacccgcc gugcucgcac aggcuucugg | 180 |
| ccgugugcgc acucgugagu cuggcgacug cugcguugcu ggggcacauu cuucuccacg | 240 |
| acuuucucuu ggugcccgga gaauugucgg gcucgcgcc gguacuggaa gaaacccacc | 300 |
| ccgcacauca gcagggcgcg ucgcggccug guccgaggga ugcccaggca caucccggaa | 360 |
| ggccacgagc cgucccgacu caaugugacg uaccucccaa uccccgguuc gacugugcgc | 420 |
| cagacaaggc aaucacgcaa gagcagugcg aagcccgugg augcugcuau auuccggcga | 480 |
| agcagggacu ucagggagcc cagauggggc agcccuggug uuucuucccg ccuuccuauc | 540 |
| ccucauauaa gcuggagaau uugucguccu cggaaauggg guauaccgcu acucuuacga | 600 |
| gaaccacccc cacauucuuu ccgaaggaca uccuuacucu gcggcucgac gugaugaugg | 660 |
| agacagaaaa uaggcugcau uucacgauca aagacccggc gaaccggaga uaugagguuc | 720 |
| cgcuugagac uccccacguu cacucucgug cgccuucacc cuuguacucc gggaguucu | 780 |
| cggaagaacc guucggggug aucgucagac gucaacuuga ugguagggua uugcugaaca | 840 |
| caacggucgc ccccuuguuu uucgccgacc aguuucugca gcuucgacau cgcugccgu | 900 |
| cccaguauau cacagggcuc gcggagcauc uuucacccu caugcugagc acgagcugga | 960 |
| cacggauuac gcucuggaac agggaucucg cgccgacgcc cggagcgaau uguauggggu | 1020 |
| cgcaucccuu cuaccucgca uuggaagacg ggggguuccgc gcacgaguaa uuccugcuua | 1080 |
| auucuaaugc gauggacguu gucuugcagc ccuccccugc uuugucgugg cguuccacgg | 1140 |
| ggggcauuuu ggacguuuac aucuuuuugg gacccgagcc aaagagcgua gugcagcagu | 1200 |
| auuuggaugu aguggggcuac cccuucaugc cgccuuauug gggacugggg uuccaucucu | 1260 |
| gccgcugggg guacucuucg accgcgauca cccgccaggu ggucgagaac augaccagag | 1320 |
| cacauuuccc uuuggacgug cagugggaaug auuuggauua caugggauagc cgaagagacu | 1380 |
| ucacguucaa uaaggacggg uuuagagauu uuccgcgcau ggucaagaa uugcaccagg | 1440 |
| gugggcgcag auacaugaug aucgucgauc ccgccaucag cagcucggga ccagcgggaa | 1500 |
| guuaccggcc uuacgaugag ggacuuagga gaggcgucuu uaucacgaac gaaacagguc | 1560 |
| agccgcucau ugguaaagug uggcuggau caacggccuu uccgacuuc acgaauccca | 1620 |
| cagcccucgc cugguggaa gacaugguugg cggaguuuca cgaccaagua ccguuugaug | 1680 |

-continued

```
ggauguggau ugauaugaac gaacccucaa acuuuauucg cggcucggaa gauggaugcc   1740
cgaauaauga gcuugagaau cccccguaug ugccaggggu gguaggguggg acgcuccagg   1800 ccgcuacgau cugugcguca ucacaucagu ucuugucaac gcacuacaac uugcacaauc   1860
uuuacgguuu gacugaagcc aucgcuucgc aucgcgcgcu ggucaaagcg cgugguacgc   1920
gacccuucgu uauuucucgg uccacauuug ccgggcacgg ucgguaugcc ggacacugga   1980
cgggagaugu cuggucuagc ugggagcagc ucgcgucgag cguaccggag auccuccagu   2040
ucaaucuuuu gggaguuccg cucgucggcg cugacgugug cgguuuucuc ggaaacacau   2100
cagaagagcu uugcguacgc uggacacagc ucggugcguu uuaccccuuu augagaaacc   2160
auaacucguu gcucucacuc ccucaagagc cguacaguuu uucggagccu gcgcaacagg   2220
cgaugcggaa ggcauugaca cuucgcuaug cacugcuccc gcaucucuau acucuguucc   2280
aucaggccca uguggcugga gaaacggugg cgaggccccu guucuuggag uuccccaaag   2340
auaguuccac auggaccgug gaucaccagu ugcugugggg agaggcgcuu cugaucacuc   2400
cgguacuuca ggcggguaaa gcggaaguca cuggguauuu cccgcuuggg accugguacg   2460
accuucagac ugucccagua gaagcccucg gaagccugcc accuccccccu gcugcacccc   2520 gcgagccugc aauccauagc gagggccagu ggguaacguu gccagcccca cuggauacca   2580
ucaaugucca ccucagggcg gguuacauua ucccucucca aggcccuggg uugaccacca   2640
cagagucgcg ccagcagcca auggcacuug cggucgcauu gacgaaaggg ggugaagccc   2700
gaggggaacu guuuugggau gacggggaaa gccuugaggu gcuggaacgg ggagcguaca   2760
cacaagucau uuucuuggcc aggaacaaca cuauugucaa cgaguuggug cgcgugaccu   2820
cugagggugc cggacugcaa cugcagaagg ucacgguccu cggaguggcg acagcacccc   2880
aacaggnccu uaguaacgga guaccugucu cgaacuuuac auacuccccg gacacgaagg   2940
ugcucgacau cugugugucg cugcuuaugg gggaacaguu ucucgugagc uggugcuagg   3000
gguggcaucc cugugacccc uccccagugc cucuccuggc ccuggaaguu gccacuccag   3060
ugcccaccag ccuuguccua auaaaauuaa guugcaucaa agcu                     3104
```